(12) United States Patent
Shavit et al.

(10) Patent No.: US 10,866,173 B2
(45) Date of Patent: Dec. 15, 2020

(54) THAWING BIOLOGICAL SUBSTANCES

(71) Applicant: FreMon Scientific, Inc., La Jolla, CA (US)

(72) Inventors: Menachem Shavit, Forest Hills, NY (US); Frederick J. Thacher, La Jolla, CA (US)

(73) Assignee: FreMon Scientific, Inc., La Jolla, CA (US)

( * ) Notice: Subject to any disclaimer, the term of this patent is extended or adjusted under 35 U.S.C. 154(b) by 0 days.

(21) Appl. No.: 16/405,960

(22) Filed: May 7, 2019

(65) Prior Publication Data

US 2019/0336660 A1 Nov. 7, 2019

Related U.S. Application Data

(60) Provisional application No. 62/668,034, filed on May 7, 2018.

(51) Int. Cl.
| | |
|---|---|
| *A61M 1/02* | (2006.01) |
| *G01N 1/44* | (2006.01) |
| *H05B 1/02* | (2006.01) |
| *H05B 3/06* | (2006.01) |
| *A61J 1/10* | (2006.01) |

(Continued)

(52) U.S. Cl.
CPC ............ *G01N 1/44* (2013.01); *A01N 1/0263* (2013.01); *A61J 1/10* (2013.01); *A61J 1/16* (2013.01); *A61J 1/18* (2013.01); *A61M 1/0281* (2013.01); *A61M 5/445* (2013.01); *B01F 11/0017* (2013.01); *B01F 15/065* (2013.01); *H05B 1/025* (2013.01); *H05B 3/06* (2013.01); *A61J 2200/42* (2013.01); *A61J 2200/70* (2013.01); *A61J 2200/72* (2013.01); *A61J 2200/74* (2013.01); *A61J 2205/60* (2013.01); *A61M 1/025* (2013.01); *A61M 2205/3368* (2013.01); *A61M 2205/3393* (2013.01); *A61M 2205/36* (2013.01); *A61M 2205/3653* (2013.01); *A61M 2205/50* (2013.01); *B01F 2015/062* (2013.01); *B01F 2215/0034* (2013.01)

(58) Field of Classification Search
CPC ........ A61M 1/0281; A61M 2205/3653; H05B 1/025; A61J 2200/42
USPC ........... 219/413, 385, 509; 435/286.7, 287.4, 435/291.5; 62/62, 66, 237, 356, 378
See application file for complete search history.

(56) References Cited

U.S. PATENT DOCUMENTS

| | | |
|---|---|---|
| 2,640,906 A | 6/1953 | Haynes |
| 3,475,590 A | 10/1969 | Pins |

(Continued)

FOREIGN PATENT DOCUMENTS

| | | |
|---|---|---|
| CN | 102802693 A | 11/2012 |
| CN | 105999444 A | 10/2016 |

(Continued)

OTHER PUBLICATIONS

International Search Report and Written Opinion for PCT/US2015/044513 Jan. 5, 2016 (17 pages).

(Continued)

*Primary Examiner* — Jimmy Chou
(74) *Attorney, Agent, or Firm* — Cooley LLP

(57) ABSTRACT

Dry thawing systems and devices for thawing biological substances are provided herein. Methods for thawing biological substances are also provided.

24 Claims, 40 Drawing Sheets

(51) Int. Cl.
  *A61J 1/16*    (2006.01)
  *A01N 1/02*    (2006.01)
  *A61J 1/18*    (2006.01)
  *A61M 5/44*    (2006.01)
  *B01F 11/00*   (2006.01)
  *B01F 15/06*   (2006.01)

(56)          References Cited

U.S. PATENT DOCUMENTS

| | | | |
|---|---|---|---|
| 3,485,245 | A | 12/1969 | Lahr et al. |
| 3,518,393 | A | 6/1970 | Besseling et al. |
| 3,590,215 | A | 6/1971 | Anderson et al. |
| 3,798,418 | A | 3/1974 | Reik et al. |
| 3,898,023 | A | 8/1975 | Faust |
| 4,309,592 | A | 1/1982 | Le Boeuf |
| 4,486,389 | A | 12/1984 | Darnell et al. |
| 4,680,445 | A | 7/1987 | Ogawa |
| 4,731,072 | A | 3/1988 | Aid |
| 4,847,470 | A | 7/1989 | Bakke |
| 4,852,641 | A | 8/1989 | Noble |
| 4,967,061 | A | 10/1990 | Weber, Jr. et al. |
| 5,013,889 | A | 5/1991 | Bakke |
| 5,081,697 | A | 1/1992 | Manella |
| 5,114,681 | A * | 5/1992 | Bertoncini ....... G01N 35/00584 422/111 |
| 5,206,479 | A * | 4/1993 | Zakaria .................. B01J 19/126 219/726 |
| 5,245,693 | A | 9/1993 | Ford et al. |
| 5,261,255 | A | 11/1993 | Coelho et al. |
| 5,297,234 | A | 3/1994 | Harms et al. |
| 5,364,385 | A | 11/1994 | Harms et al. |
| 5,368,569 | A | 11/1994 | Sanese |
| H1623 | H | 1/1997 | Reed et al. |
| 5,603,220 | A | 2/1997 | Seaman |
| 5,616,268 | A | 4/1997 | Carr |
| 5,691,452 | A | 11/1997 | Gawryl et al. |
| 5,779,974 | A * | 7/1998 | Kuzyk .................. A61M 5/445 165/104.31 |
| 6,007,773 | A | 12/1999 | Kuzyk |
| 6,142,974 | A | 11/2000 | Kistner et al. |
| 6,159,368 | A * | 12/2000 | Moring .................. B01D 61/18 210/258 |
| 6,259,067 | B1 | 7/2001 | Faries, Jr. et al. |
| 6,371,121 | B1 | 4/2002 | Faries, Jr. et al. |
| 6,381,981 | B1 | 5/2002 | Yaddgo et al. |
| 6,384,380 | B1 | 5/2002 | Faries, Jr. et al. |
| 6,419,827 | B1 * | 7/2002 | Sandell .................. B01D 61/18 210/321.75 |
| 6,432,320 | B1 | 8/2002 | Bonsignore et al. |
| 6,452,138 | B1 | 9/2002 | Kochman et al. |
| 6,503,457 | B1 * | 1/2003 | Neeper ................ B01J 19/0046 422/527 |
| 6,596,531 | B2 | 7/2003 | Campbell et al. |
| 6,638,761 | B2 * | 10/2003 | Shin ...................... B01L 3/5085 219/385 |
| 6,684,646 | B2 * | 2/2004 | Voute ...................... A01N 1/00 62/66 |
| 6,698,213 | B2 | 3/2004 | Voute et al. |
| 6,727,480 | B2 | 4/2004 | Fernando et al. |
| 6,730,883 | B2 * | 5/2004 | Brown ................ B01L 3/50851 219/385 |
| 6,748,164 | B1 | 6/2004 | Kuzyk |
| 6,786,054 | B2 | 9/2004 | Voute et al. |
| 6,824,528 | B1 | 11/2004 | Faries, Jr. et al. |
| 6,861,624 | B1 | 3/2005 | Pelster |
| 6,931,864 | B2 | 8/2005 | Fuhr et al. |
| 6,945,056 | B2 | 9/2005 | Brown et al. |
| 6,996,995 | B2 | 2/2006 | Voute et al. |
| 7,011,797 | B2 | 3/2006 | Bakke |
| 7,019,267 | B2 * | 3/2006 | Weinfield ................ B01D 61/18 219/385 |
| 7,041,941 | B2 | 5/2006 | Faries, Jr. et al. |
| 7,077,559 | B2 | 7/2006 | Hlavinka et al. |
| 7,104,074 | B2 * | 9/2006 | Voute ...................... A01N 1/00 280/79.3 |
| 7,137,261 | B2 | 11/2006 | Brown et al. |
| 7,228,688 | B2 | 6/2007 | Voute et al. |
| 7,276,675 | B2 | 10/2007 | Faries, Jr. |
| 7,278,278 | B2 | 10/2007 | Wowk et al. |
| 7,307,245 | B2 * | 12/2007 | Faries, Jr. ............. A61M 5/445 219/413 |
| 7,353,658 | B2 | 4/2008 | Voute et al. |
| 7,433,030 | B2 * | 10/2008 | Waldo .................. A61L 2/0011 356/218 |
| 7,452,510 | B2 * | 11/2008 | Weinfield ............... B01D 61/18 141/130 |
| 7,603,921 | B2 | 10/2009 | Baumfalk et al. |
| 7,618,808 | B1 | 11/2009 | Papp |
| 7,638,100 | B2 | 12/2009 | Dawes |
| 7,711,251 | B2 | 5/2010 | Barkey |
| 7,722,839 | B2 * | 5/2010 | Kuzyk .................. A01N 1/0242 100/269.04 |
| 7,920,802 | B2 | 4/2011 | Minagawa |
| 7,924,169 | B2 | 4/2011 | Baumfalk et al. |
| 7,955,840 | B2 | 6/2011 | Belgrader |
| 7,958,791 | B2 | 6/2011 | Zimmermann et al. |
| 8,012,416 | B2 | 9/2011 | Kuzyk |
| 8,028,532 | B2 | 10/2011 | Voute et al. |
| 8,037,696 | B2 | 10/2011 | Shaham et al. |
| 8,070,354 | B2 | 12/2011 | Bungay, III et al. |
| 8,329,433 | B2 | 12/2012 | Belgrader |
| 8,371,132 | B2 | 2/2013 | Cutting et al. |
| 8,377,030 | B2 | 2/2013 | Hyde et al. |
| 8,448,457 | B2 | 5/2013 | Cutting et al. |
| 8,451,138 | B2 | 5/2013 | Zimmermann et al. |
| 8,539,790 | B1 | 9/2013 | Budd |
| 8,550,703 | B2 | 10/2013 | Cutting |
| 8,852,536 | B2 | 10/2014 | Davidowitz et al. |
| 8,863,532 | B2 | 10/2014 | Voute et al. |
| 8,906,652 | B2 | 12/2014 | Belgrader |
| 8,968,232 | B2 | 3/2015 | Kamen et al. |
| 9,000,332 | B2 * | 4/2015 | Brown ...................... A61C 5/55 219/385 |
| 9,034,635 | B2 | 5/2015 | Termaat et al. |
| 9,046,292 | B2 | 6/2015 | Burke et al. |
| 9,103,703 | B2 | 8/2015 | Baumfalk et al. |
| 9,121,403 | B2 | 9/2015 | Lanigan et al. |
| 9,140,487 | B2 | 9/2015 | Chaffey et al. |
| 9,173,248 | B2 | 10/2015 | Baker |
| RE45,789 | E | 11/2015 | Shei et al. |
| 9,357,763 | B2 | 6/2016 | Cullis et al. |
| 9,441,893 | B2 | 9/2016 | Velayudhan et al. |
| 9,648,970 | B2 | 5/2017 | Lee |
| 9,707,528 | B2 | 7/2017 | Suchocki et al. |
| 9,764,075 | B2 | 9/2017 | Blickhan et al. |
| 9,833,580 | B2 | 12/2017 | Cho |
| 9,920,970 | B2 | 3/2018 | Arnitz et al. |
| 9,932,632 | B2 | 4/2018 | Kreifels et al. |
| 10,023,833 | B2 | 7/2018 | Akerstrom et al. |
| 10,057,699 | B2 | 8/2018 | Maggiore et al. |
| 10,196,598 | B2 * | 2/2019 | Baust ........................ B01L 7/00 |
| 10,202,572 | B2 | 2/2019 | Tanaka et al. |
| 10,208,280 | B2 | 2/2019 | Joaquim Rodrigues et al. |
| 10,221,384 | B2 | 3/2019 | Akerstrom et al. |
| 10,232,331 | B2 | 3/2019 | Boettcher et al. |
| 10,251,389 | B2 | 4/2019 | Kamieli et al. |
| 10,499,458 | B2 | 12/2019 | Shavit et al. |
| 10,576,190 | B2 | 3/2020 | Shavit |
| 2001/0042743 | A1 * | 11/2001 | Faries, Jr. ............. A61F 7/0241 219/400 |
| 2003/0082069 | A1 | 5/2003 | Kuzyk |
| 2004/0006999 | A1 * | 1/2004 | Brown ...................... A01N 1/02 62/62 |
| 2004/0045954 | A1 * | 3/2004 | Lehman .................... A61L 2/26 219/521 |
| 2004/0241835 | A1 * | 12/2004 | Hutmacher ............ C12M 25/14 435/298.2 |
| 2004/0265168 | A1 | 12/2004 | Bakke |
| 2005/0126929 | A1 | 6/2005 | Mansouri et al. |
| 2005/0230376 | A1 * | 10/2005 | Gomez .................. A61F 7/0085 219/385 |

(56) References Cited

U.S. PATENT DOCUMENTS

| | | |
|---|---|---|
| 2006/0153549 A1 | 7/2006 | Cazzini et al. |
| 2007/0029311 A1 | 2/2007 | Akashi et al. |
| 2007/0127901 A1* | 6/2007 | Kuzyk ............... A61M 1/0281 392/446 |
| 2007/0217810 A1 | 9/2007 | Minagawa |
| 2007/0240432 A1* | 10/2007 | Voute .................. A61J 1/165 62/66 |
| 2008/0310768 A1 | 12/2008 | Hobson et al. |
| 2009/0009290 A1 | 1/2009 | Kneip et al. |
| 2009/0026907 A1* | 1/2009 | Davidowitz ...... G01N 35/00722 312/407 |
| 2010/0075405 A1 | 3/2010 | Broadley et al. |
| 2010/0078422 A1* | 4/2010 | Staab .................. H05B 1/025 219/413 |
| 2010/0206862 A1* | 8/2010 | Defranco ............ A47K 10/06 219/201 |
| 2010/0291536 A1* | 11/2010 | Viljoen ............ A61B 10/0051 435/4 |
| 2011/0082437 A1* | 4/2011 | Stacey .................. F25D 15/00 604/404 |
| 2011/0127273 A1* | 6/2011 | Deane .................. A61J 1/00 220/592.2 |
| 2011/0151482 A1* | 6/2011 | Emery .................. G01N 1/30 435/7.9 |
| 2011/0186517 A1* | 8/2011 | Hedmann ............ A61M 1/282 210/645 |
| 2011/0198255 A1* | 8/2011 | Baumfalk ........ G01N 35/00732 206/459.1 |
| 2012/0234817 A1 | 9/2012 | Baker |
| 2012/0330234 A1 | 12/2012 | Balluff et al. |
| 2013/0091890 A1 | 4/2013 | Schryver et al. |
| 2013/0304006 A1 | 11/2013 | Toth |
| 2014/0071216 A1 | 3/2014 | Hu et al. |
| 2014/0231406 A1* | 8/2014 | Tsang .................. A61M 5/44 219/394 |
| 2015/0334774 A1* | 11/2015 | Schryver ............ H05B 1/025 219/439 |
| 2016/0010871 A1* | 1/2016 | Baker .................. H05B 1/025 219/411 |
| 2016/0097583 A1* | 4/2016 | Baust .................. B01L 7/00 62/129 |
| 2016/0106624 A1 | 4/2016 | Camisani et al. |
| 2016/0220748 A1 | 8/2016 | Pouchoulin |
| 2016/0243000 A1 | 8/2016 | Gray |
| 2017/0036181 A1* | 2/2017 | Boettcher ............ A61M 5/44 |
| 2017/0135902 A1 | 5/2017 | Scully, Jr. |
| 2017/0239404 A1* | 8/2017 | Shavit .................. A61J 1/18 |
| 2017/0257908 A1 | 9/2017 | Schryver et al. |
| 2017/0277829 A1 | 9/2017 | Weggler et al. |
| 2018/0050856 A1 | 2/2018 | Baud et al. |
| 2018/0125754 A1 | 5/2018 | Sanchez et al. |
| 2018/0126345 A1 | 5/2018 | Topp-Manske |
| 2018/0127703 A1 | 5/2018 | Jarvius et al. |
| 2018/0147306 A1* | 5/2018 | Crawley ............ A61L 2/0047 |
| 2018/0163164 A1 | 6/2018 | Husemann et al. |
| 2018/0177180 A1 | 6/2018 | Chapman et al. |
| 2018/0245031 A1 | 8/2018 | Sato et al. |
| 2018/0250666 A1 | 9/2018 | Paul et al. |
| 2018/0251715 A1 | 9/2018 | Paul et al. |
| 2018/0255766 A1 | 9/2018 | Dick et al. |
| 2018/0320126 A1 | 11/2018 | Doody |
| 2018/0324900 A1* | 11/2018 | Shavit ................ H05B 1/025 |
| 2018/0360023 A1 | 12/2018 | McPherson et al. |
| 2019/0003939 A1 | 1/2019 | Milne et al. |
| 2019/0041308 A1 | 2/2019 | Schryver et al. |
| 2019/0048303 A1 | 2/2019 | Maggiore |
| 2019/0075786 A1 | 3/2019 | Milne et al. |
| 2019/0144811 A1 | 5/2019 | Heese et al. |
| 2019/0151519 A1 | 5/2019 | Shavit |
| 2019/0152676 A1 | 5/2019 | Murphy |
| 2019/0194593 A1 | 6/2019 | Ozaki et al. |
| 2019/0336706 A1 | 11/2019 | Shavit et al. |
| 2019/0339176 A1 | 11/2019 | Shavit |

FOREIGN PATENT DOCUMENTS

| | | |
|---|---|---|
| DE | 3121280 A1 | 1/1983 |
| DE | 3225695 A1 | 1/1984 |
| DE | 3311591 A1 | 10/1984 |
| DE | 3321603 A1 | 12/1984 |
| DE | 3500614 A1 | 7/1986 |
| DE | 3640114 A1 | 6/1988 |
| DE | 3705596 A1 | 9/1988 |
| DE | 3723861 A1 | 1/1989 |
| DE | 3741051 C1 | 6/1989 |
| DE | 3800283 A1 | 7/1989 |
| DE | 3900101 A1 | 7/1990 |
| DE | 4316163 C2 | 4/1995 |
| DE | 4328321 C2 | 6/1995 |
| DE | 19503350 C1 | 7/1996 |
| DE | 4444180 C2 | 4/1997 |
| DE | 19841556 C1 | 3/2000 |
| DE | 19940715 C2 | 12/2001 |
| DE | 10035297 A1 | 2/2002 |
| DE | 10112465 C1 | 7/2002 |
| DE | 10238492 A1 | 4/2004 |
| DE | 20-2004-017612 U1 | 1/2005 |
| DE | 10324116 A1 | 1/2005 |
| DE | 10332781 A1 | 2/2005 |
| DE | 10-2005-036369 A1 | 2/2007 |
| DE | 20-2005-021496 U1 | 5/2008 |
| DE | 10-2007-056169 A1 | 5/2009 |
| DE | 10-2009-011707 A1 | 6/2010 |
| DE | 10-2010-002895 A1 | 9/2011 |
| DE | 20-2013-101214 U1 | 4/2013 |
| DE | 20-2013-102927 U1 | 8/2013 |
| DE | 11-2015-000765 A5 | 11/2016 |
| DE | 10-2015-113325 A1 | 2/2017 |
| EP | 0 432 591 A1 | 6/1991 |
| EP | 0 318 924 B1 | 3/1992 |
| EP | 0 396 729 B1 | 8/1994 |
| EP | 0 653 215 A1 | 5/1995 |
| EP | 0 527 944 B1 | 4/1996 |
| EP | 0 786 981 B1 | 9/1998 |
| EP | 1 138 304 A2 | 10/2001 |
| EP | 1 174 703 A2 | 1/2002 |
| EP | 0 880 663 B1 | 4/2003 |
| EP | 1 426 672 A1 | 6/2004 |
| EP | 1 299 138 B1 | 10/2005 |
| EP | 1 441 585 B1 | 5/2006 |
| EP | 1 441 586 B1 | 6/2006 |
| EP | 1 747 790 B1 | 9/2007 |
| EP | 1 476 013 B1 | 5/2011 |
| EP | 2 389 063 B1 | 10/2012 |
| EP | 2 547 386 A2 | 1/2013 |
| EP | 2 839 822 A1 | 2/2015 |
| EP | 2 914 104 A2 | 9/2015 |
| EP | 2 976 637 A1 | 1/2016 |
| EP | 2 442 857 B1 | 8/2016 |
| EP | 3 104 917 A1 | 12/2016 |
| EP | 3 016 558 B1 | 10/2017 |
| GB | 952521 A | 3/1964 |
| JP | 5-261625 B1 | 8/2013 |
| RU | 2552822 C1 | 6/2015 |
| WO | WO-88/07384 A1 | 10/1988 |
| WO | WO-92/21254 A1 | 12/1992 |
| WO | WO-95/09597 A1 | 4/1995 |
| WO | WO-00/14463 A1 | 3/2000 |
| WO | 2010031237 A1 | 3/2010 |
| WO | 2010132627 A2 | 11/2010 |
| WO | WO-2011/113421 A2 | 9/2011 |
| WO | WO-2011/113421 A3 | 9/2011 |
| WO | WO-2014/146641 A1 | 9/2014 |
| WO | WO-2015/000464 A1 | 1/2015 |
| WO | WO-2015/120843 A1 | 8/2015 |
| WO | WO-2017/025789 A4 | 2/2017 |
| WO | WO-2018/000051 A1 | 1/2018 |
| WO | WO-2018/010999 A1 | 1/2018 |
| WO | WO-2018/025053 A1 | 2/2018 |

(56) References Cited

FOREIGN PATENT DOCUMENTS

| WO | WO-2018/195107 A1 | 10/2018 |
| WO | WO-2018/211437 A1 | 11/2018 |

OTHER PUBLICATIONS

Extended European Search Report issued in corresponding European Application No. 15829831.5 dated Aug. 13, 2018 (8 pages).
International Search Report and Written Opinion issued in International Application No. PCT/US18/25650 dated Jul. 2, 2018 (9 pages).
Corrected Notice of Allowability dated Oct. 23, 2019, for U.S. Appl. No. 16/405,974, filed May 7, 2019, 2 pages.
Final Office Action dated Sep. 19, 2019, for U.S. Appl. No. 16/260,100, filed Jan. 28, 2019, 18 pages.
Non-Final Office Action dated May 30, 2019, for U.S. Appl. No. 15/502,642, filed Mar. 7, 2017, 23 pages.
Non-Final Office Action dated May 31, 2019, for U.S. Appl. No. 16/260,100, filed Jan. 28, 2019, 24 pages.
Non-Final Office Action dated Jul. 19, 2019, for U.S. Appl. No. 16/405,974, filed May 7, 2019, 9 pages.
Non-Final Office Action dated Nov. 12, 2019, for U.S. Appl. No. 16/405,966, filed May 7, 2019, 7 pages.
Non-Final Office Action dated Dec. 10, 2019, for U.S. Appl. No. 15/901,231, filed Feb. 21, 2018, 21 pages.
Non-Final Office Action dated Dec. 11, 2019, for U.S. Appl. No. 16/405,987, filed May 7, 2019, 10 pages.
Non-Final Office Action dated Dec. 12, 2019, for U.S. Appl. No. 16/405,994, filed May 7, 2019, 7 pages.
Notice of Allowance dated Sep. 3, 2019, for U.S. Appl. No. 16/405,974, filed May 7, 2019, 8 pages.
Notice of Allowance dated Sep. 20, 2019, for U.S. Appl. No. 15/502,642, filed Mar. 7, 2017, 10 pages.
Corrected Notice of Allowability dated Jan. 14, 2020, for U.S. Appl. No. 15/502,642, filed Mar. 7, 2017, 2 pages.
Final Office Action dated Jun. 24, 2020, for U.S. Appl. No. 15/901,231, filed Feb. 21, 2018, 16 pages.
International Search Report dated Oct. 9, 2019, for PCT Application No. PCT/US2019/031215, filed on May 7, 2019, 9 pages.
Non-Final Office Action dated Mar. 25, 2020, for U.S. Appl. No. 16/405,966, filed May 7, 2019, 6 pages.
Notice of Allowance dated Mar. 17, 2020, for U.S. Appl. No. 16/260,100, filed Jan. 28, 2019, 8 pages.
Notice of Allowance dated Mar. 23, 2020, for U.S. Appl. No. 16/405,994, filed May 7, 2019, 8 pages.
Notice of Allowance dated Jun. 5, 2020, for U.S. Appl. No. 16/405,987, filed May 7, 2019, 9 pages.
Notice of Allowance dated Jul. 6, 2020, for U.S. Appl. No. 16/405,966, filed May 7, 2019, 6 pages.
Written Opinion of the International Searching Authority dated Oct. 9, 2019, for PCT Application No. PCT/US2019/031215, filed on May 7, 2019, 13 pages.

\* cited by examiner

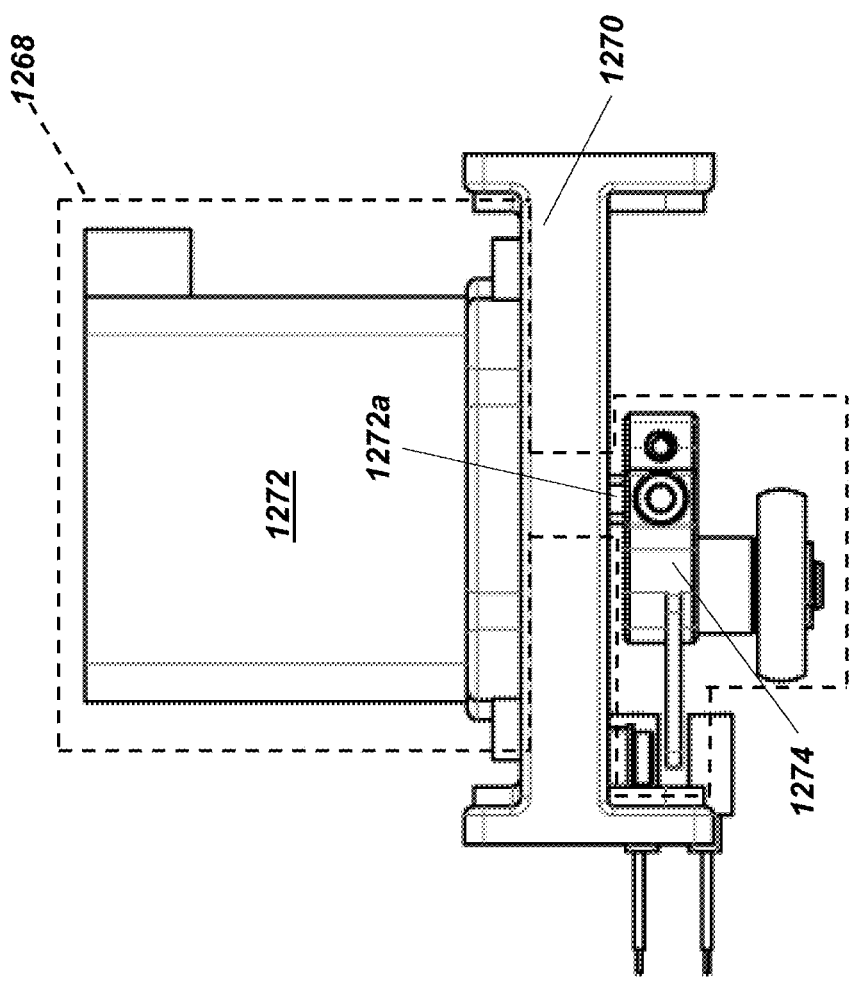

THAWING BIOLOGICAL SUBSTANCES

CROSS-REFERENCE TO RELATED APPLICATIONS

The present application claims priority to U.S. Provisional Application No. 62/668,034, filed on May 7, 2018, and entitled "Device for Thawing of Biological Substances," which is hereby incorporated by reference in its entirety.

FIELD

The present application relates to methods and devices for thawing biological substances.

BACKGROUND

Bags containing biological substances such as plasma, blood, blood products, and medication can be supplied to medical facilities for transfusion in large volume on a daily basis. These bags can be frozen, stored in inventory upon arrival, and thawed to a designated temperature just prior to transfusion.

The quality of thawed biological substances can depend upon the process by which they are thawed. Underheating a biological substance can cause patients to experience hypothermia. Conversely, overheating a biological substance can cause severe damage (e.g., denaturation) to proteins and other components that can reduce the quality of the transfused fluid, endangering patients.

Accordingly, improved methods and devices are needed to thawing biological substances.

SUMMARY

In general, methods and devices for thawing biological substances are provided.

In one embodiment, a dry thawing device is provided and includes a chamber frame configured to receive an enclosed biological substance, and a first heating assembly coupled to the chamber frame. The first heating assembly has a heater configured to be in thermal communication with an enclosed biological substance that is received within the chamber frame. The device further includes an agitation device mounted within the chamber frame and configured to cause the first heating assembly to pivot about a pivot axis relative to the chamber frame such that the first heating assembly can agitate an enclosed biological substance received within the chamber frame.

The device can have a variety of configurations. In one embodiment, first heating assembly can be linearly slidably movable relative to the chamber frame. The device can include at least one biasing element that biases the first heating assembly into contact with an enclosed biological substance that is received within the chamber frame.

In other aspects, the device can include a chamber door that is pivotally coupled to the chamber frame and that is moveable between open and closed positions. A second heating assembly can be mounted on the chamber door. The second heating assembly can have a heater that, when the chamber door is in a closed position, is configured to be in thermal communication with an enclosed biological substance that is received within the chamber frame. The first heating assembly can be configured to be positioned adjacent to a first side of an enclosed biological substance that is received within the chamber frame and the second heating assembly can be configured to be positioned adjacent to a second side of the enclosed biological substance that is opposite the first side.

In other aspects, the device can include at least one temperature sensor configured to measure a temperature of at least one of the first heating assembly and an enclosed biological substance received within the chamber frame. In another embodiment, the device can include a weight sensor configured to measure a weight of an enclosed biological substance that is received within the chamber frame. In another aspect, an overwrap bag can be disposed within the chamber frame, and the overwrap bag can contain an enclosed biological substance.

In another embodiment, a dry thawing device is provided and includes a chamber frame having a top portion, a bottom portion, and first and second opposed sidewalls coupled to the top and bottom portions. A support frame can be mounted to the bottom portion of the chamber frame and it can extend between the top and bottom portions of the chamber frame. An agitator plate can be pivotally coupled to the support frame, and the agitator plate can be configured to contact an enclosed biological substance disposed within the chamber frame. An agitation device can be mounted to the support frame and it can be configured to cause pivotal motion of the agitator plate to thereby agitate an enclosed biological substance disposed within the chamber frame.

In one aspect, the agitation device can include a cam mechanism configured to cam the agitator plate to cause pivotal motion of the agitator plate. The agitator plate can extend between the top and bottom portions of the chamber frame and can be pivotally mounted at a mid-portion thereof to the support frame.

In other aspects, the support frame can be slidably mounted to the bottom portion of the chamber frame. The support frame can be biased toward an enclosed biological substance disposed within the chamber frame to thereby bias the agitator plate toward an enclosed biological substance disposed within the chamber frame. The agitator plate can include a first heating assembly mounted thereon and configured to selectively generate thermal energy to heat an enclosed biological substance disposed within the chamber frame. In certain aspects, the agitator plate includes a top end and a bottom end, and pivotal motion of the agitator plate causes the top and bottom ends to move in opposite directions.

The device can also include a chamber door mounted to the first end of the chamber frame. The chamber door can be moveable between open and closed positions. When the chamber door is in the closed position, the chamber door and the agitator plate can define a cavity there between that is configured to receive an enclosed biological substance. A second heating assembly can be mounted on the chamber door, and the second heating assembly can have a heater that is configured to selectively generate heat to thaw an enclosed biological substance disposed within the cavity.

In another embodiment, a method for thawing a biological substance is provided and includes positioning an enclosed biological substance in a frozen state within a cavity in a housing such that the enclosed biological substance is in thermal communication with a first heating assembly located within the housing, activating the heating assembly to heat and thereby thaw the enclosed biological substance, and activating an agitation device to cause an agitator plate disposed within the housing to pivot about a pivot axis and thereby agitate the enclosed biological substance.

In certain aspects, the heating assembly can be mounted on the agitator plate such that the heating assembly pivots within pivotal motion of the agitator plate. The agitation device can be activated while the heating assembly is activated.

In one embodiment, a dry thawing device is provided and includes a housing, a chamber frame disposed within the housing and having a base extending from a first end to a second end, and a chamber door pivotally mounted to the first end of the base and disposed at a first end of the housing. The chamber door can be movable between an open position, in which an enclosed biological substance can be inserted into a cavity within the housing, and a closed position, in which the chamber door encloses the enclosed biological substance within the cavity. A first heating assembly can be mounted on an inner surface of the chamber door such that a heater of the first heating assembly is configured to deliver thermal energy to heat an enclosed biological substance disposed within the cavity.

The device can also include a second heating assembly disposed within the housing and having a heater that is configured to selectively generate thermal energy to heat an enclosed biological substance that is received within the cavity. The first and second heating assemblies can define the cavity for receiving the enclosed biological substance there between. The second heating assembly can be mounted on an agitator plate disposed within the housing and configured to pivot about a pivot axis to agitate an enclosed biological substance disposed within the cavity. The agitator plate can be pivotally mounted to a support plate that is linearly slidably mounted on the base of the chamber frame.

The device can also include at least one temperature sensor that is configured to measure a temperature of at least one of the first heating assembly and an enclosed biological substance received within the cavity. The device can include a weight sensor that is configured to measure a weight of an enclosed biological substance that is received within the cavity. An overwrap bag can be disposed within the cavity and it can contain an enclosed biological substance.

In other aspects, the device can include a second chamber frame disposed within the housing and having a base extending from a first end to a second end, and a second chamber door pivotally mounted to the first end of the base of the second chamber frame and disposed at a second end of the housing opposite to the first end. The second chamber door can be movable between an open position, in which a second enclosed biological substance can be inserted into a second cavity within the housing, and a closed position, in which the second chamber door encloses the second enclosed biological substance within the cavity In another embodiment, a dry thawing device is provided and includes a housing having opposed top and bottom sides, opposed front and back sides extending between the top and bottom sides, and opposed left and right sides extending between the top and bottom sides and between the front and back sides. A first chamber door is positioned on the left side of the housing and is pivotally movable between open and closed positions. The first chamber door has a first heating assembly mounted thereon and having a first heater that is configured to selectively generate thermal energy to heat a first enclosed biological substance disposed within the housing adjacent to the first chamber door. A second chamber door is positioned on the right side of the housing and is pivotally movable between open and closed positions. The second chamber door has a second heating assembly mounted thereon and having a second heater that is configured to selectively generate thermal energy to heat a second enclosed biological substance disposed within the housing adjacent to the second chamber door.

In one aspect, a first agitator plate can be disposed within the housing to define a first cavity there between with the first chamber door such. The first cavity can be configured to receive a first enclosed biological substance, and the first agitator plate can be configured to pivot to agitate the first enclosed biological substance. A second agitator plate can be disposed within the housing to define a second cavity there between with the second chamber door. The second cavity can be configured to receive a second enclosed biological substance, and the second agitator plate can be configured to pivot to agitate the second enclosed biological substance.

In other aspects, a third heating assembly can be mounted on the first agitator plate and a fourth heating assembly mounted on the second agitator plate. The third and fourth heating assemblies can each having a heater configured to selectively generate thermal energy to respectively heat first and second enclosed biological substances disposed within the housing. The first and second agitator plates with the third and fourth heating assemblies mounted thereon can be linearly slidable along the bottom side of the housing. The first and second chambers doors can be mounted adjacent to the bottom side of the housing such that an upper portion of each of the first and second chambers doors moves away from the top side of the housing to move to the open position.

In another embodiment, a method for thawing a biological substance is provided and includes pivoting a first chamber door on a first side of a housing from a closed position to an open position to provide access to a first cavity within the housing, positioning a first enclosed biological substance in a frozen state into the first cavity in the housing, pivoting the first chamber door to the closed position to cause a first heating assembly mounted on the first chamber door to contact the first enclosed biological substance, and activating the first heating assembly to cause a first heater of the first heating assembly to generate thermal energy to heat the first enclosed biological substance from the frozen state to a fluid state.

In one aspect, when the first chamber door is moved to the closed position, the first enclosed biological substance can be engaged between the first heating assembly on the first chamber door and a second heating assembly disposed within the housing. The method can further include activating the second heating assembly to cause a second heater of the second heating assembly to generate thermal energy to heat the first enclosed biological substance from the frozen state to a fluid state. The second heating assembly can be mounted on a first pivoting agitator plate, and the method can further include activating a first agitation device to cause the first pivoting agitator plate to pivot and thereby agitate the first enclosed biological substance.

In other aspects, the method can include monitoring a temperature of at least one of the first heating assembly and the first enclosed biological substance. In yet another aspect, the method can include pivoting a second chamber door on a second side of a housing from a closed position to an open position to provide access to a second cavity within the housing, and positioning a second enclosed biological substance in a frozen state into the second cavity in the housing. A third heating assembly mounted on the second chamber door can be activated to cause a third heater of the third heating assembly to generate thermal energy to heat the second enclosed biological substance from the frozen state to a fluid state.

In one embodiment, a dry thawing system is provided and includes a housing having a cavity configured to receive an enclosed biological substance, and a first heating assembly disposed within the housing and configured to be in thermal communication with an enclosed biological substance that is received within the cavity. The first heating assembly can have a heater that is configured to selectively generate thermal energy, and a heating cushion in thermal communication with the heater. The heating cushion can be configured to conduct thermal energy generated by the heater. At least one temperature sensor can be disposed within the housing and configured to measure a temperature of at least one of the heater and the heating cushion. The at least one temperature sensor can be in communication with a power supply configured to supply electrical power to the heater, and the at least one temperature sensor can be further configured to regulate power to the heater based upon the measured temperature.

In one aspect, the at least one temperature sensor is configured to measure the temperature of the heater. When the measured temperature exceeds a predetermined threshold temperature, the at least one temperature sensor is further configured to transmit a failsafe signal to the power supply that is operative to cause the power supply to terminate delivery of power to the heater In another aspect, the at least one temperature sensor is configured to measure the temperature of the heating cushion. When the measured temperature exceeds a predetermined threshold temperature, the at least one temperature sensor is further configured to transmit a failsafe signal to the power supply that is operative to cause the power supply to terminate delivery of power to the heater.

In one embodiment, the at least one temperature sensor can be a first temperature sensor that is configured to measure a temperature of the heater and a second temperature sensor that is configured to measure a temperature of the heating cushion. The first temperature sensor can be configured to transmit a first failsafe signal to the power supply when the measured temperature of the heater exceeds a predetermined first threshold temperature. The second temperature sensor can be configured to transmit a second failsafe signal to the power supply when the measured temperature of the heating cushion exceeds a predetermined second threshold temperature. Receipt of either of the first and second failsafe signal by the power supply is operative to cause the power supply to terminate delivery of power to the heater.

In other embodiments, the system can include the power supply. The power supply can be configured to wirelessly communicate with the at least one temperature sensor.

In another embodiment, a dry thawing system is provided and includes a housing having a cavity configured to receive an enclosed biological substance, and a first heating assembly disposed within the housing and configured to be in thermal communication with an enclosed biological substance that is received within the cavity. The first heating assembly can have a heater that is configured to selectively generate thermal energy to heat an enclosed biological substance disposed within the cavity from a frozen state to a fluid state. At least one sensor can be disposed within the housing and configured to detect at least one parameter of an enclosed biological substance that is received within the cavity. A controller can be in communication with the at least one sensor, and the controller can be configured to communicate the at least one parameter to a processor.

In one aspect, the processor can be one of a processor remote from the housing and a processor disposed within the housing. In other aspects, the at least one parameter can be at least one of a date, a geographic location, and a time. In another aspect, the at least one parameter can be data associated with a donor of a biological substance.

The at least one sensor can be configured to detect an authentication tag that is coupled to an enclosed biological substance that is received within the cavity.

In other embodiments, at least one sensor can be disposed on a chamber door pivotally mounted to the housing, and the at least one sensor can be configured to detect an authentication tag that is coupled to an enclosed biological substance that is received within the cavity.

In one embodiment, a dry thawing device is provided and includes a housing having a cavity configured to receive an enclosed biological substance, and a first heating assembly disposed within the housing and configured to be in thermal communication with an enclosed biological substance received within the cavity. The first heating assembly can have a heater that is configured to selectively generate thermal energy, and a fluid-filled cushion in thermal communication with the heater. The fluid-filled cushion can be deformable and configured to selectively transfer the thermal energy generated by the heater to an enclosed biological substance received within the cavity and in contact with the fluid-filled cushion.

In one aspect, the fluid-filled cushion includes a cushion body defining a compartment having at least one of a gel and water disposed therein.

In one embodiment, the cushion body includes an inner layer having a first surface and a second surface, with the first surface defining the compartment. The cushion body further includes a first barrier layer having a first surface and a second surface, with the first surface of the first barrier layer being disposed about at least a portion of the second surface of the inner layer, and the first barrier layer being configured to substantially prevent egress of at least one of fluid disposed in the compartment and vapor generated within the compartment. The cushion body can further include a second barrier layer that is disposed about at least a portion of the second surface of the first barrier layer such that a first portion of the second barrier layer contacts the heater and a second portion of the barrier layer contacts an enclosed biological substance received within the cavity, with the second barrier layer being configured to inhibit the inner and first barrier layers from melting.

The device can also include an agitation device disposed within the housing. The agitation device can be configured to cause the first heating assembly to pivot about a pivot axis so as to agitate an enclosed biological substance received within the cavity. At least one biasing element can bias the first heating assembly towards the cavity to cause the first heating assembly to be in thermal communication with an enclosed biological substance that is received within the cavity. The device can also include a chamber door on the housing and pivotally moveable between open and closed positions. A second heating assembly cam be coupled to the chamber door, and the second heating assembly can have a second heater that is configured to be in thermal communication with an enclosed biological substance that is received within the cavity when the chamber door is in a closed position. The second heating assembly can include a second fluid-filled cushion in thermal communication with the second heater, and the second fluid-filled cushion can be deformable and can be configured to selectively transfer the thermal energy generated by the second heater to an enclosed biological substance received within the cavity and in contact within the second fluid-filled cushion. The second fluid-filled cushion of the second heating assembly can include a cushion body having a compartment defined therein, with the compartment of the second heating assembly having at least one of a gel and water disposed therein.

In certain aspects, the second fluid-filled cushion of the second heating assembly can include a cushion body having a compartment defined therein that is configured to hold a fluid, with the cushion body of the second heating assembly including an inner layer having a first surface and a second surface, with the first surface defining the compartment. The cushion body of the second fluid-filled cushion can also include a first barrier layer having a first surface and a second surface, with the first surface of the first barrier layer being disposed about at least a portion of the second surface of the inner layer, and the first barrier layer being configured to substantially prevent egress of at least one of fluid disposed in the compartment and vapor generated within the compartment. The cushion body of the second fluid-filled cushion can also include a second barrier layer that is disposed about at least a portion of the second surface of the first barrier layer such that a first portion of the second barrier layer contacts the heater and a second portion of the barrier layer contacts an enclosed biological substance received within the cavity, with the second barrier layer being configured to inhibit the inner and first barrier layers from melting.

In other aspects, the device can include at least one temperature sensor that is configured to measure a temperature of at least one of the first heating assembly and an enclosed biological substance received within the cavity. In another aspect, the first heating assembly and the fluid-filled cushion can be removable and replaceable.

In another embodiment, a heating assembly for heating a biological substance is provided and includes a support member a heating assembly mounted on the support member and having a heater that is configured to selectively generate thermal energy, and a fluid-filled cushion mounted on the support member and in thermal communication with the heater, with the fluid-filled cushion being deformable and configured to conduct thermal energy generated by the heater.

The fluid-filled cushion can include a cushion body defining a compartment therein, the compartment having at least one of a gel and water disposed therein. The cushion body can have an inner layer having a first surface and a second surface, with the first surface defining the compartment, a first barrier layer having a first surface and a second surface, with the first surface of the first barrier layer being disposed about at least a portion of the second surface of the inner layer, and the first barrier layer being configured to substantially prevent egress of at least one of fluid disposed in the compartment and vapor generated within the compartment, and a second barrier layer that is disposed about at least a portion of the second surface of the first barrier layer such that a first portion of the second barrier layer contacts the heater and a second portion of the barrier layer is configured to contact a substance to be heated, with the second barrier layer being configured to inhibit the inner and first barrier layers from melting.

In an embodiment, a method is provided. The method can include receiving, within a chamber frame, an enclosed biological substance. The method can also include measuring, by a first temperature sensor, a first temperature representing a temperature of a predetermined portion of at least one heating assembly. The at least one heating assembly can be in thermal communication with the enclosed biological substance received within a chamber frame. The at least one heating assembly can also be configured to selectively generate thermal energy in response to receipt of a command signal. The method can further include measuring, by a second temperature sensor, a second temperature representing a temperature of the enclosed biological substance. The method can additionally include measuring, by a weight sensor, a weight of the enclosed biological substance. The method can further include receiving, by a controller in communication with the at least one heating assembly, the first temperature, the second temperature, and the weight. The method can also include generating, by the controller, at least one command signal based upon the first temperature, the second temperature, and the weight.

In another embodiment, the controller can be configured to generate one or more first command signals according to a first operation stage when a predetermined fraction of the enclosed biological substance is solid. The controller can also be configured to generate one or more second command signals according to a second operation stage when a predetermined fraction of the enclosed biological substance is liquid.

In another embodiment, generating the one or more first command signals by the controller can include receiving a first heating assembly set point temperature for the predetermined portion of the at least one heating assembly, determining first proportional-integral-derivative (PID) settings based upon the weight of the enclosed biological substance, and generating the one or more first command signals based upon the first PID settings and a difference between the first temperature measurement and the first heating assembly set point temperature.

In another embodiment, the first heating assembly set point can be selected from the range of about 37° C. to about 42° C.

In another embodiment, generating the one or more second command signals by the controller includes receiving a second heating assembly set point temperature, different from the first heating assembly set point temperature, receiving second PID settings, different from the first PID settings, and generating the one or more second command signals based upon the second PID settings and a difference between the first temperature measurement and the second heating assembly set point temperature.

In another embodiment, the method can further include, by the controller, receiving a transition temperature set point temperature for the enclosed biological substance, and generating the one or more second command signals after determining that the second temperature is about equal to the transition temperature.

In another embodiment, the transition temperature can be selected from about 5° C. to about 8° C.

In another embodiment, the method can further include, by the controller, receiving a final temperature for the enclosed biological substance and defining an end of the second operation stage when the second temperature measurement is about equal to the final temperature.

In another embodiment, the final temperature can be selected from about 30° C. to about 37° C.

In another embodiment, the method can further include, by the controller, defining a thawing time elapsed from commencement of the first operating stage to a time prior to the end of the second operation stage, determining that the thawing time exceeds a predetermined maximum thawing time, and transmitting a command signal operative to cause the at least one heating assembly to cease generation of heat.

In another embodiment, after the end of the second operation stage, the controller can be configured to generate one or more third command signals according to a third operation stage operative to achieve a pre-determined third heating assembly set point temperature.

In another embodiment, the method can further include, by the controller, receiving the third heating assembly set point temperature, receiving third PID settings, different from the first and second PID settings; and generating the one or more third command signals based upon the third PID settings and a difference between the first temperature measurement and the third heating assembly set point temperature In another embodiment, the method can further include, by the controller, defining a standby time elapsed from commencement of the third operating stage, determining that the standby time exceeds a predetermined maximum standby time, and annunciating an alarm.

In another embodiment, the method can further include, by the controller, receiving a fourth heating assembly set point temperature, receiving fourth PID settings, and prior to generating the first or second command signals, generating one or more fourth command signals based upon the fourth PID settings and a difference between the first temperature measurement and the fourth heating assembly set point temperature.

In another embodiment, the fourth heating assembly set point can be selected from about 35° C. to about 40° C.

In another embodiment, the method can further include receiving the enclosed biological substance within the chamber frame after determining, by the controller, that the first temperature measurement is about equal to the fourth heating assembly set point temperature. Receiving the enclosed biological substance can include opening a chamber door pivotably mounted to a first end of a base of the chamber frame prior to the first operation stage.

In another embodiment, the method can further include, prior to measuring the weight of the enclosed biological substance, determining by the controller that the chamber door is closed.

In another embodiment, the at least one heating assembly can includes a heater configured to selectively generate the thermal energy, and a heating cushion in thermal communication with the heater and the enclosed biological substance. The first temperature can be a temperature of the heating cushion.

In another embodiment, the at least one heating assembly can include a first heating assembly and a second heating assembly. The first heating assembly can be positioned adjacent to a first side of the enclosed biological substance and the second heating assembly can be positioned adjacent to a second side of the enclosed biological substance, opposite the first heating assembly.

In another embodiment, the method can further include axially translating the first heating assembly along a base of the chamber frame to place the at least one heating assembly in thermal communication with the enclosed biological substance.

BRIEF DESCRIPTION OF THE DRAWINGS

These and other features will be more readily understood from the following detailed description taken in conjunction with the accompanying drawings, in which:

FIG. 14 is a back view of an agitation device and chassis of the first dry thawing chamber of FIG. 11C;

Figure 1A:
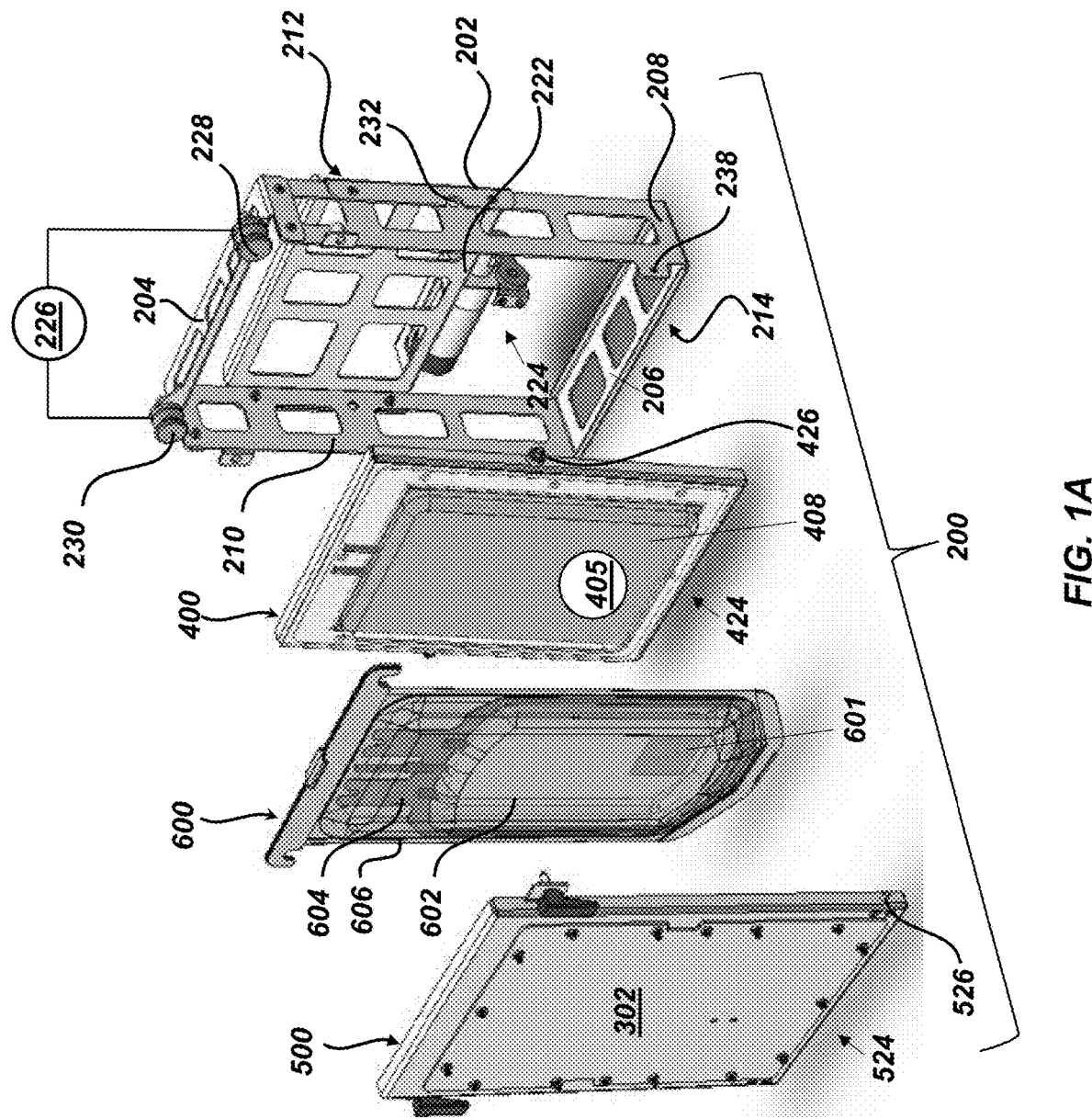
FIG. 1A is an exploded, front-view of one embodiment of a dry thawing chamber, illustrating a first heating assembly, a second heating assembly, a bag assembly, and an agitation device mounted to a frame.

It is noted that the drawings are not necessarily to scale. The drawings are intended to depict only typical aspects of the subject matter disclosed herein, and therefore should not be considered as limiting the scope of the disclosure.

DETAILED DESCRIPTION

Certain exemplary embodiments are described below to provide an overall understanding of the principles of the structure, function, manufacture, and use of the devices disclosed herein. One or more examples of these embodiments are illustrated in the accompanying drawings. Those skilled in the art will understand that the devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

Existing systems for thawing enclosures containing a frozen biological substance (e.g., medication, plasma, glycerolized blood, red blood corpuscles (RBCs), etc.) operate by placing the bag in contact with heated water (e.g., water baths or water bladders). Heat is transferred from the water to the biological substance over a selected time duration to thaw the biological substance to a desired temperature range. However, these systems do not individually monitor the temperature of each bag for quality control during the thawing process. Typically, the ambient temperature of the water bath or water bladder is monitored during the thawing process. Alternatively, at best, sampled quantities of biological substances are evaluated after thawing. Thus, it can be difficult to achieve reproducible and consistent thawing of the biological substances, creating opportunities for errors that can be harmful to patients.

Accordingly, dry thawing methods and devices are provided that can receive enclosures containing biological substances and that can supply heat to thaw the biological substance without an intermediate heat conducting fluid (e.g., water baths or water bladders). The applied heat can be dynamically controlled based upon temperature measurements acquired at or near a surface of the enclosure. Temperature measurements can also be recorded to provide a complete temperature record during the thawing process.

Embodiments are discussed herein with respect to thawing biological substances, such as medications and blood. Examples of such biological substances can include, but are not limited to, whole blood, blood products, plasma derivatives, mother's milk, ovaries, eggs, sperm, embryos, tissue, drugs, cells, such as chimeric antigen receptors t-cell (CAR-T) or other T-cells, molecular reagents, antibodies, etc.

In general, a dry thawing system can include at least one dry thawing chamber that is configured to receive an enclosed biological substance. In an exemplary embodiment, the at least one dry thawing chamber can include any one or more of a chamber frame, at least one heating assembly, an agitator device configured to agitate the enclosed biological substance, and at least one temperature sensor. The at least one heating assembly can include a heater that is configured to heat the enclosed biological substance disposed within the chamber frame. The at least one temperature sensor can be configured to monitor the temperature of the enclosed biological substance.

Dry Thawing Chamber

Figure 1B:
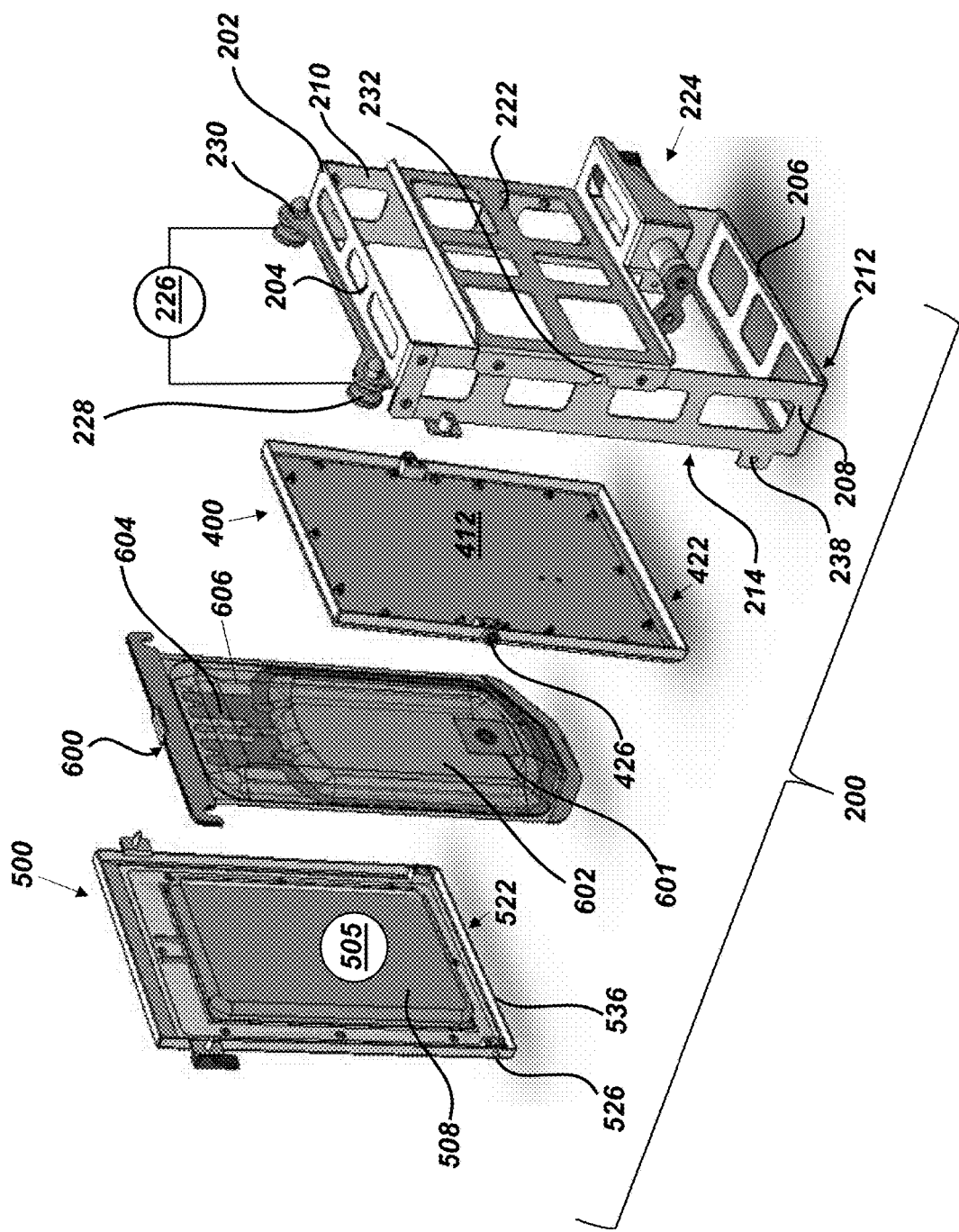
FIG. 1B is an exploded, rear-facing view of the dry thawing chamber of FIG. 1A, illustrating the first heating assembly, the second heating assembly, the bag assembly, and the agitation device mounted to the frame.

FIGS. 1A-1B illustrate one exemplary embodiment of a dry thawing chamber 200. As shown, the dry thawing chamber 200 includes a chamber frame 202 having a top portion 204, a bottom portion 206, a first sidewall 208, and a second sidewall 210 opposite the first sidewall 208. The first and second sidewalls 208, 210 extend between the top portion 204 and the bottom portion 206. A first heating assembly 400 is pivotally mounted proximate to a first end 212 (e.g., rear end) of the chamber frame 202, about a first pivot 426. A second heating assembly 500 is pivotally mounted to a second end 214 (e.g., front end) of the chamber frame 202, opposite the first end 212, about a second pivot 526. A bag assembly 600 can be removably disposed within a cavity formed between the first heating assembly 400 and the second heating assembly 500 in order to be in thermal communication with a heater 408 of the first heating assembly 400 and a heater 508 of the second heating assembly 500. As shown in FIGS. 1A and 1B, and in more detail in FIGS. 5A-5C, the bag assembly 600 includes a biological substance 602 disposed within an enclosure 604 that is further disposed within an overwrap bag 606, as will be discussed in more detail below.

The chamber frame 202 can have a variety of configurations. In the illustrated embodiment, the chamber frame 202 includes a cross-member 222 mounted to the sidewalls 208, 210 and an agitation device 224 mounted to the cross-member 222. As discussed below, so positioned, the agitation device 224 can contact a rear-facing surface 422 of the first heating assembly 400 to cause pivotal movement of the first heating assembly 400 about the first pivot 426.

Optionally, the dry thawing chamber 200 can include a mechanism for estimating the weight and/or volume of the bag assembly 600, and thus the enclosed biological substance 602. In one embodiment, as shown in FIGS. 1A and 1B, the dry thawing chamber 200 includes one or more weight measuring sensors 226 (e.g., load cell[s] [LC]) for measuring a weight of the bag assembly 600. As an example, the weight measuring sensor 226 can be provided in communication with one or more of the mounting posts 228, 230. Thus, when the bag assembly 600 is positioned within the dry thawing chamber 200 and supported by the mounting posts 228, 230, an accurate measurement of the weight of the bag assembly 600 can be obtained.

This measured weight can be transmitted to a controller for determination of the weight of the enclosed biological substance 602. In one aspect, the controller can determine the weight of the enclosed biological substance 602. In embodiments where the weight of the enclosure 604 and the overwrap bag 606 are negligible compared to the weight of the enclosed biological substance 602, the measured weight can be approximately equal to the weight of the enclosed biological substance 602. In embodiments where the weight of the enclosure 604 and the overwrap bag 606 are not negligible compared to the weight of the enclosed biological substance 602, the controller can subtract the weights of the enclosure 604 and the overwrap bag 606 from the measured weight to obtain the weight of the enclosed biological substance 602. The weights can be obtained by the controller from a data storage device or input by an operator of the dry thawing system using an user interface device.

Alternatively or additionally, the controller can be configured to estimate a volume of the enclosed biological substance 602 based upon the determined weight of the enclosed biological substance 602. In one aspect, the controller can use a density of the enclosed biological substance 602 to determine the volume of the enclosed biological substance 602. In another aspect, the controller can use a lookup table to determine the volume of the enclosed biological substance 602. The density and/or lookup table can be obtained by the controller from a data storage device or input by an operator of the dry thawing system using an user interface device.

As indicated above, the first heating assembly 400 can be pivotably mounted to the chamber frame 202. For example, as shown in FIGS. 1A-1B, the first heating assembly 400 includes a first pivot 426. While the first pivot 426 can have a variety of configurations, as shown, the first pivot 426 is in the form of two pivot pins each extending laterally outward from opposing sides of the first heating assembly 400. The chamber frame 202 includes a first pivot mount 232 that is in the form of a first pivot bore extending through a first sidewall 208 of the chamber frame 202 and a second pivot bore extending through the second sidewall 210 of the chamber frame 202. The first pivot mount 232 is configured to receive the first pivot 426. When the first heating assembly 400 is mounted to the first pivot mount 232, at least a portion of the first heating assembly 400 can be positioned between the first and second sidewalls 208, 210. So configured, the first heating assembly 400 forms a planar structure mounted proximate to the first end 212 (e.g., rear end) of the chamber frame 202.

The location of the first pivot 426 and first pivot mount 232 can be selected along the height of the first heating assembly 400 and the chamber frame 202. As shown, the first pivot 426 and the first pivot mount 232 are positioned at a location roughly centered along the height of the first heating assembly 400 and the first and second sidewalls 208, 210 of the chamber frame 202, respectively. However, alternative embodiments of the dry thawing chamber 200 can include the first pivot 426 and first pivot mount 232 at other locations, such as adjacent to the top portion 204 or bottom portion 206 of the chamber frame 202. As discussed in greater detail below, the pivoting engagement of the first heating assembly 400 and chamber frame 202 allows the agitation device 224, also mounted to the chamber frame 202, to mechanically engage the first heating assembly 400 and urge it to pivot.

The second heating assembly 500 can be part of or can form the chamber door 302 and the chamber door 302 can be pivotably mounted to the chamber frame 202. For example, the second heating assembly 500 can include a second pivot 526. While the second pivot 526 can have a variety of configurations, as shown, the second pivot 526 is in the form of two pivot pins each extending laterally outward from opposing sides of the second heating assembly 500. The chamber frame 202 includes a second pivot mount 238 that is in the form of a first pivot bore extending through a first sidewall 208 of the chamber frame 202 and a second pivot bore extending through the second sidewall 210 of the chamber frame 202. The second pivot mount 238 is configured to receive the second pivot 526.

The location of the second pivot 526 and second pivot mount 238 can be selected along the length of the second heating assembly 500 and the chamber frame 202. As shown, the second pivot 526 and the second pivot mount 238 are positioned at locations adjacent to an end 536 (e.g., a bottom end) of the second heating assembly 500 and the bottom portion 206 of the chamber frame 202, respectively. So configured, the second heating assembly 500 forms a planar structure mounted to a second end 214 (e.g., front end) of the chamber frame 202, opposite the first end 212.

Figure 2B:
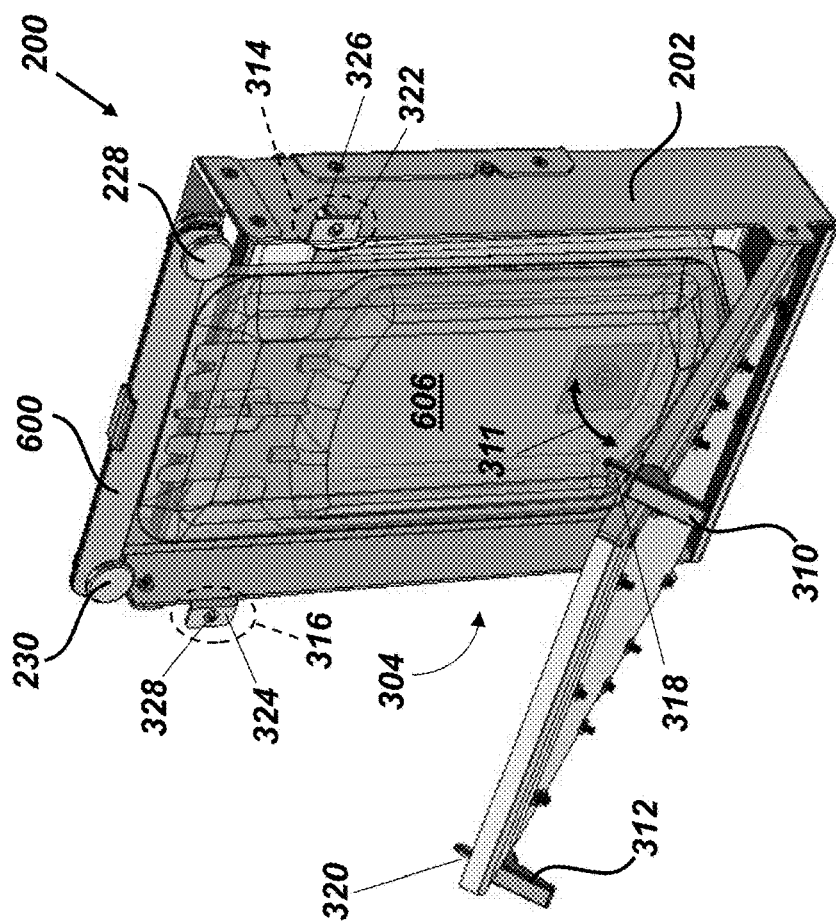
FIG. 2B is an isometric front view of the dry thawing chamber of FIGS. 1A-1B with the chamber door pivoted to an open position.
Figure 2A:
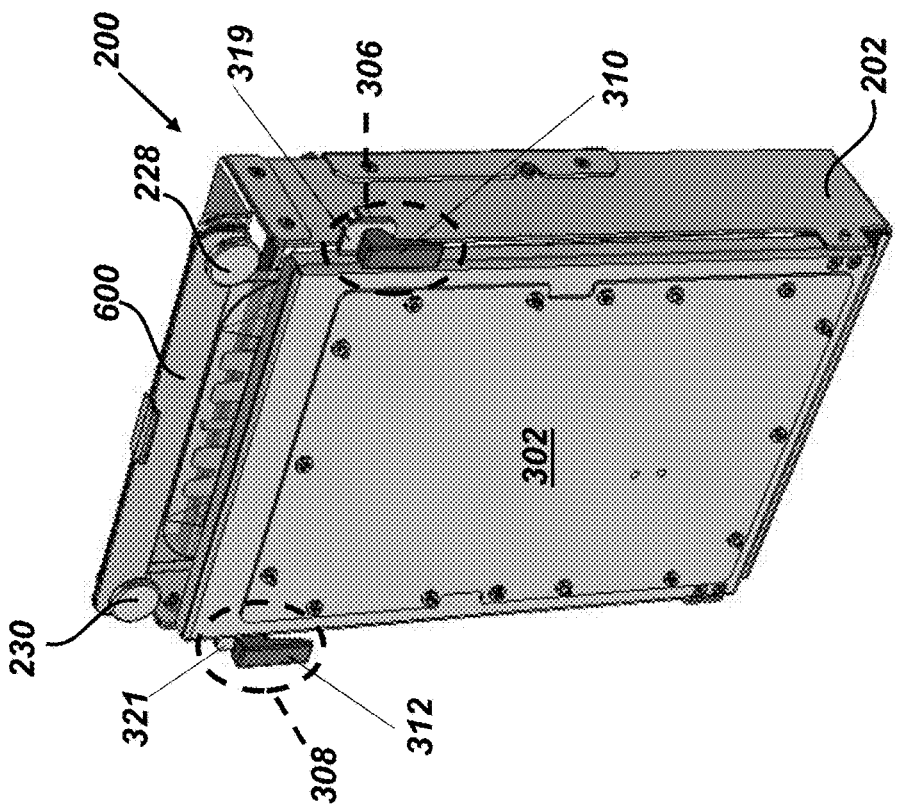
FIG. 2A is a isometric front-view of the dry thawing chamber of FIGS. 1A-1B with a chamber door in a closed position.

As shown in FIGS. 2A-2B, this configuration can allow the chamber door 302 to pivot about the second pivot 526, denoted by arrow 311, between an open position and a closed position. In the open position (FIG. 2B), the upper portion of the chamber door 302 moves away from the chamber to expose a cavity 304 defined between the chamber frame 202, the first heating assembly 400, and the second heating assembly 500. Thus, when the chamber door 302 is in the open position, the cavity 304 is accessible from outside of the dry thawing chamber 200 and an bag assembly 600 can be inserted between the first heating assembly 400 and second heating assembly 500. In the closed position (FIG. 2A), the cavity 304 becomes sealed from the exterior of the dry thawing chamber 200 (a sealed cavity). The sealed cavity can be dimensioned to accommodate the bag assembly 600 including the overwrap bag 606, the enclosure 604, and the enclosed biological substance 602 contained therein. Furthermore, in the closed position, the bag assembly 600 received within the sealed cavity is positioned in contact with heating cushions 404, 504 of the first and second heating assemblies 400, 500 and adjacent to heaters 408, 508, respectively.

The chamber door 302 and chamber frame 202 can include at least one latching mechanism to lock the chamber door 302 in the closed position during use. As shown in FIGS. 2A-2B, the chamber door 302 and the chamber frame 202 include first and second latching mechanisms 306, 308. While the first and second latching mechanisms 306, 308 can have a variety of configurations, in the illustrated embodiment the first and second latching mechanisms 306, 308 are structurally similar and each include a latching member 310, 312 and a receiving member 314, 316. As shown in FIGS. 2A-2B, each latching member 310, 312 includes a protrusion 318, 320 extending outwardly therefrom and through a flange 319, 321 extending outwardly from the chamber door 302. Each receiving member 314, 316 in the form of a flange 322, 324 extending outwardly from the chamber frame 202 and includes a bore 326, 328 extending therethrough. The bores 326, 328 are configured to receive the protrusion 318, 320 of corresponding latching members 310, 312. In other embodiments, other latching mechanisms can be used.

Figure 2D:
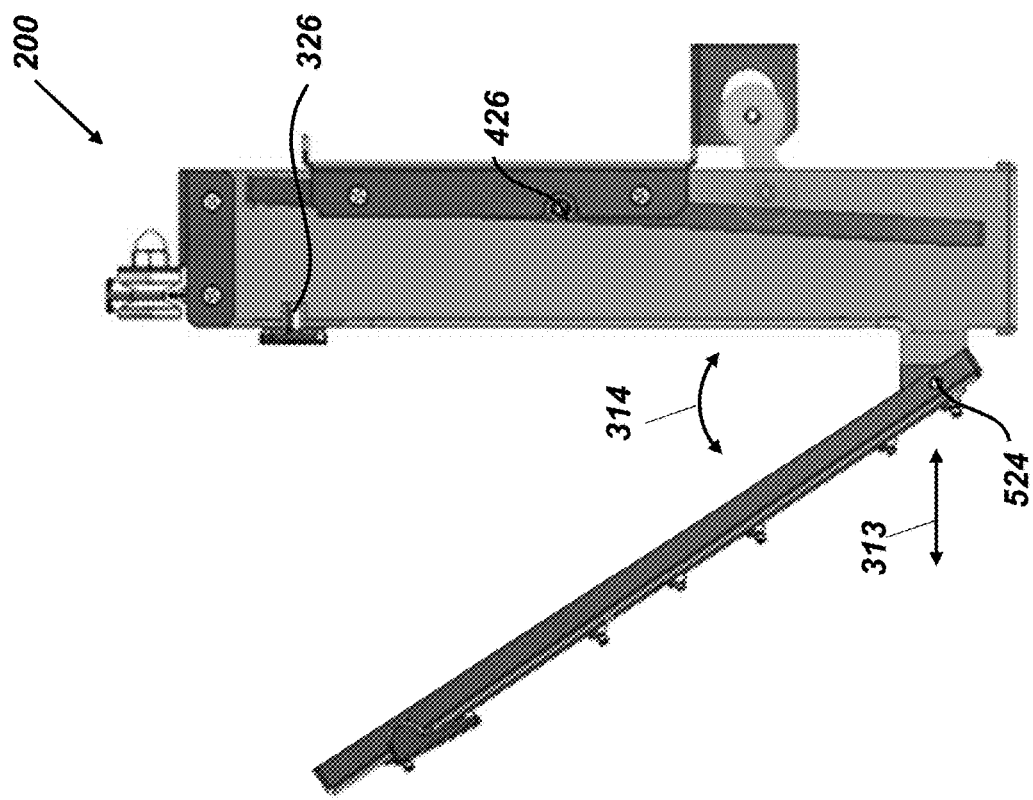
FIG. 2D is a side view of the dry thawing chamber of FIGS. 1A-1B illustrating sliding and pivoting of the chamber door in the open position.
Figure 2C:
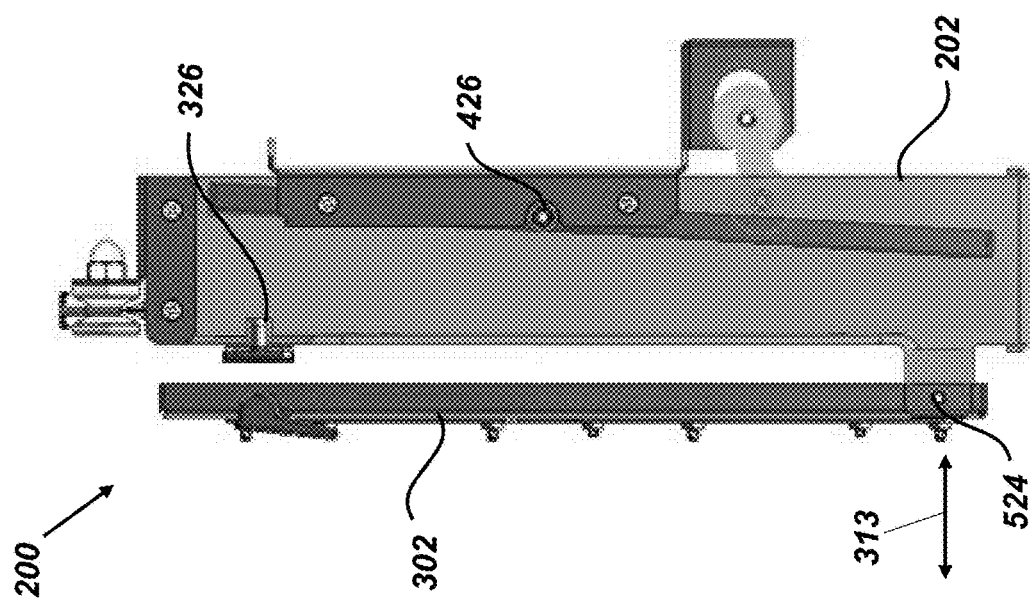
FIG. 2C is a side view of the dry thawing chamber of FIGS. 1A-1B illustrating sliding of the chamber door in the open position.

As further illustrated in FIGS. 2C-2D, the chamber door 302 can be configured to linearly slide towards and away, denoted by arrow 313, from the chamber frame 202. As an example, the portion of the chamber frame 202 including the second pivot mount 238 can include telescoping rails (not shown) or other sliding mechanisms. By sliding the chamber door 302 away from the chamber frame 202, as denoted by arrow 313, alone or in combination with pivoting, as denoted by arrow 311, additional space can be provided for inserting the bag assembly 600 within the dry thawing chamber 200.

Heating Assembly

Figure 3:
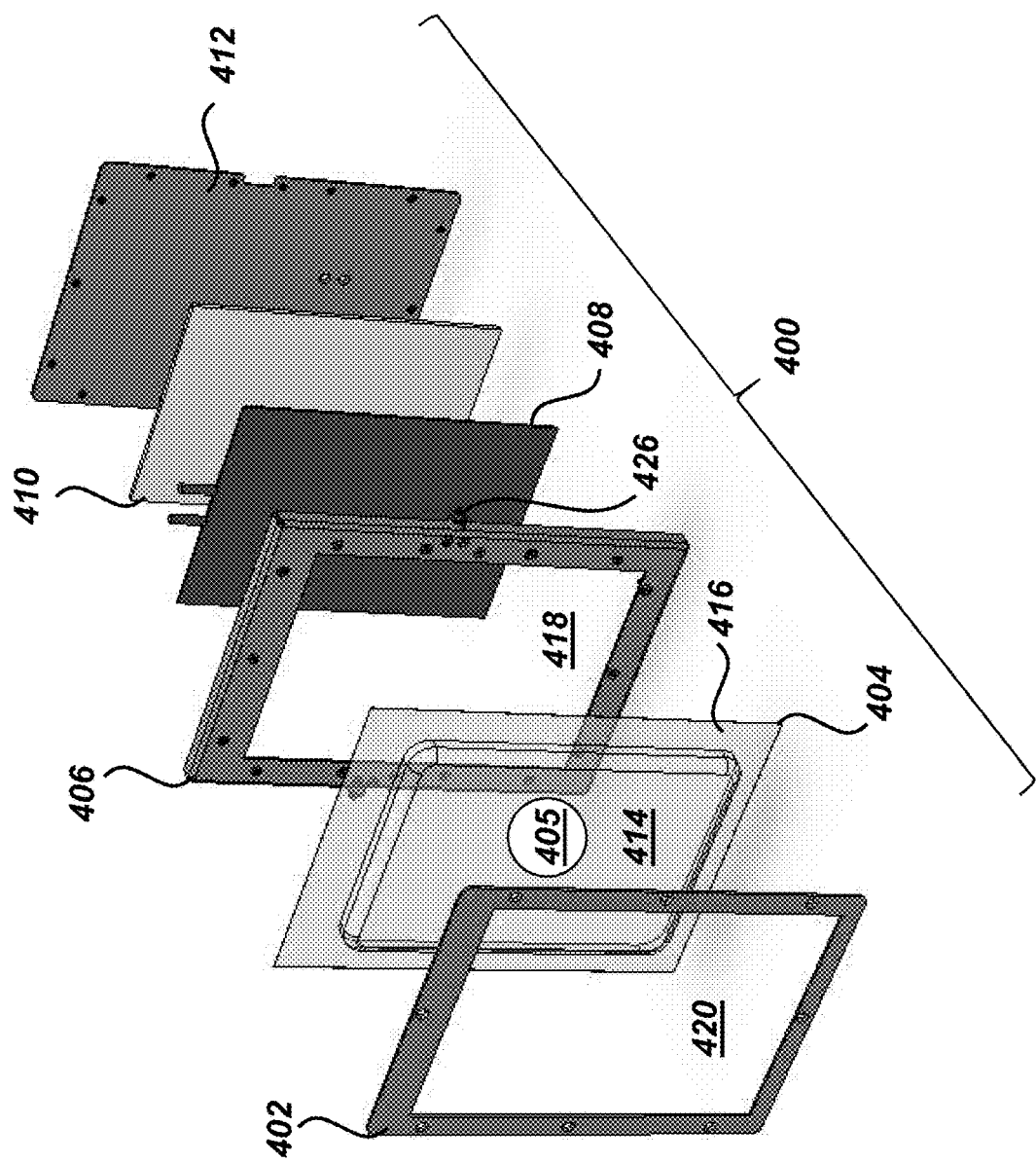
FIG. 3 is an exploded view illustrating the first heating assembly of the dry thawing chamber of FIGS. 1A-1B.

Each heating assembly can have a variety of configurations. FIG. 3 is an exploded, isometric view of the first heating assembly 400. As shown, the first heating assembly 400 includes, from front to rear, a first assembly frame 402, the heating cushion 404 with a contact temperature sensor 405 coupled thereto, a second assembly frame 406, the heater 408, an isolator 410, and a cover 412. The contact temperature sensor 405 can be similar to third contact temperature sensor 130 shown in FIGS. 19A and 19C-19E. The isolator 410 can be a generally flexible, planar structure that possesses a relatively low thermal conductivity configured to inhibit transfer of heat from the heater 408 to the cover 412. As an example, the isolator 410 can be formed from materials such as one or more of polystyrene foam, starch-based foams, cellulose, paper, rubber, and plastic. The heater 408 can be a generally flexible, planar structure that is configured to generate heat. In certain embodiments, the heater 408 can be a resistive heater that generates heat in response to receipt of electrical current. The heating cushion 404 can include a cushion body 414 and a lip 416 extending laterally outward from an outer periphery of the cushion body 414.

When the first heating assembly 400 is assembled, the cover 412 is coupled to the second assembly frame 406. The heater 408 can be positioned within or adjacent to the aperture 418 of the second assembly frame 406, with the isolator 410 interposed between the cover 412 and the heater 408. The second assembly frame 406 is further coupled to the first assembly frame 402. The heating cushion lip 416 can be positioned between the second assembly frame 406 and the first assembly frame 402 and secured thereto (e.g., by friction, one or more fasteners, adhesives, etc.). At least a portion of the heating cushion body 414 can extend through the aperture 420 of the first assembly frame 402. So assembled, the cover 412 forms a generally planar, rigid rear-facing surface 422 of the first heating assembly 402, as shown in FIG. 1A, the cushion body 414 forms a deformable front-facing surface 424 of the first heating assembly 402, as shown in FIG. 1B, and heat can be conducted from the heater 408 to the exterior surface of the cushion body 414.

Figure 4:
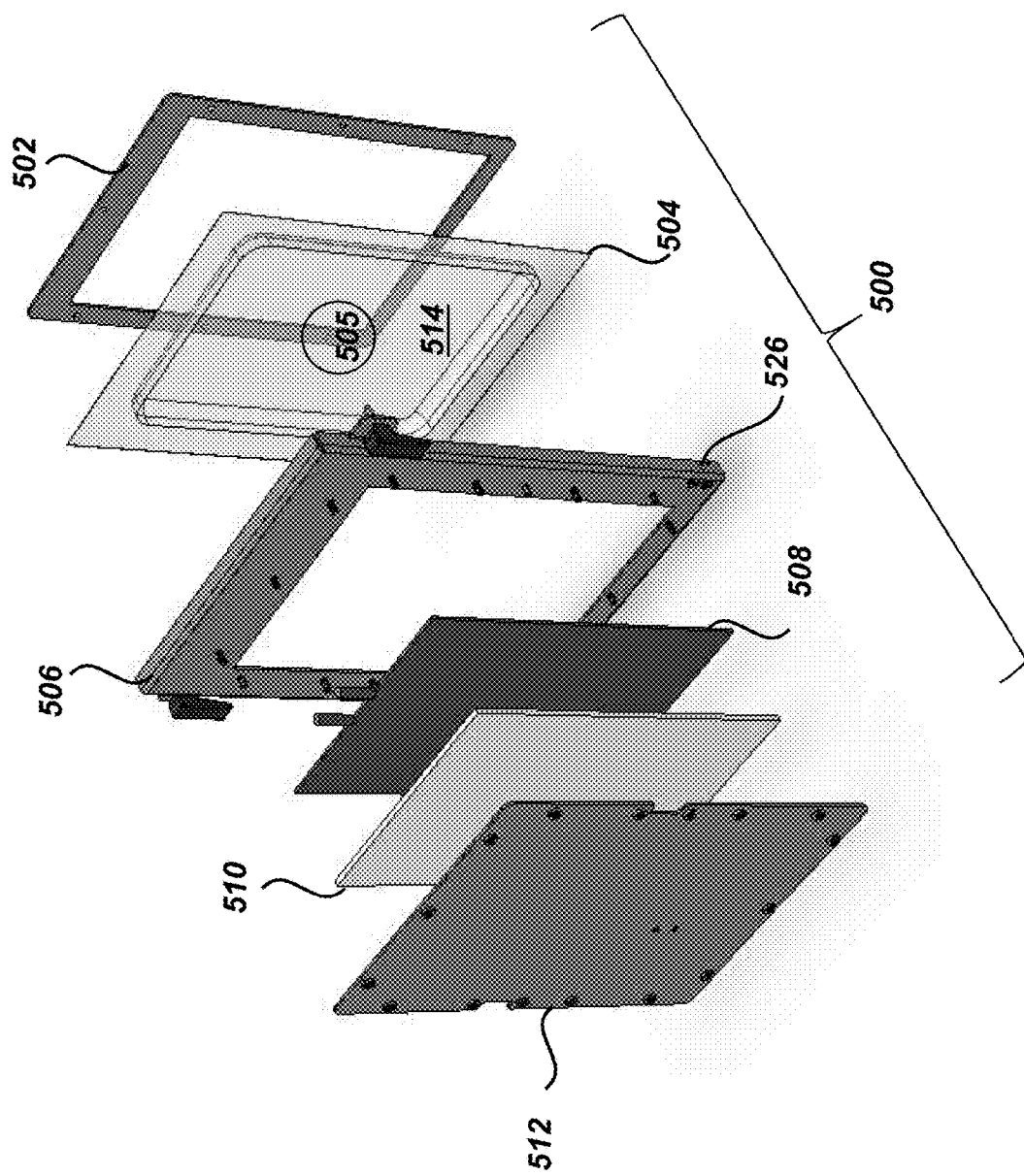
FIG. 4 is an exploded view illustrating the second heating assembly of the dry thawing chamber of FIGS. 1A-1B.

The second heating assembly 500 can be formed and assembled similarly to the first heating assembly 400. As shown in FIG. 4, the second heating assembly 500 includes, from front to rear, the cover 512, the isolator 510, the heater 508, the second assembly frame 506, the heating cushion 504 with a contact temperature sensor 505 coupled thereto, and the first assembly frame 502. So assembled, the cover 512 and second assembly frame 506 form a front-facing surface 524 of the second heating assembly 500 (e.g., the chamber door 302), as shown in FIG. 1A, while the cushion body 514 forms a deformable rear-facing surface 522 of the second heating assembly 500, as shown in FIG. 1B, and heat can be conducted from the heater 508 to the exterior surface of the cushion body 514. The contact temperature sensor 505 can be similar to fourth contact temperature sensor 132 shown in FIGS. 19A and 19C-19E.

The cushion body 414 can be formed from a material having a relatively high thermal conductivity configured to permit transfer of heat from the heater therethrough. In further embodiments, the cushion body 414 can be formed from a reversibly deformable material. As an example, the cushion body 414 can be filled with a fluid. Non-limiting examples of suitable fluids include water, gel, synthetic oils, non-synthetic oils, other heat-absorbing materials, or any combination thereof.

Figure 18A:
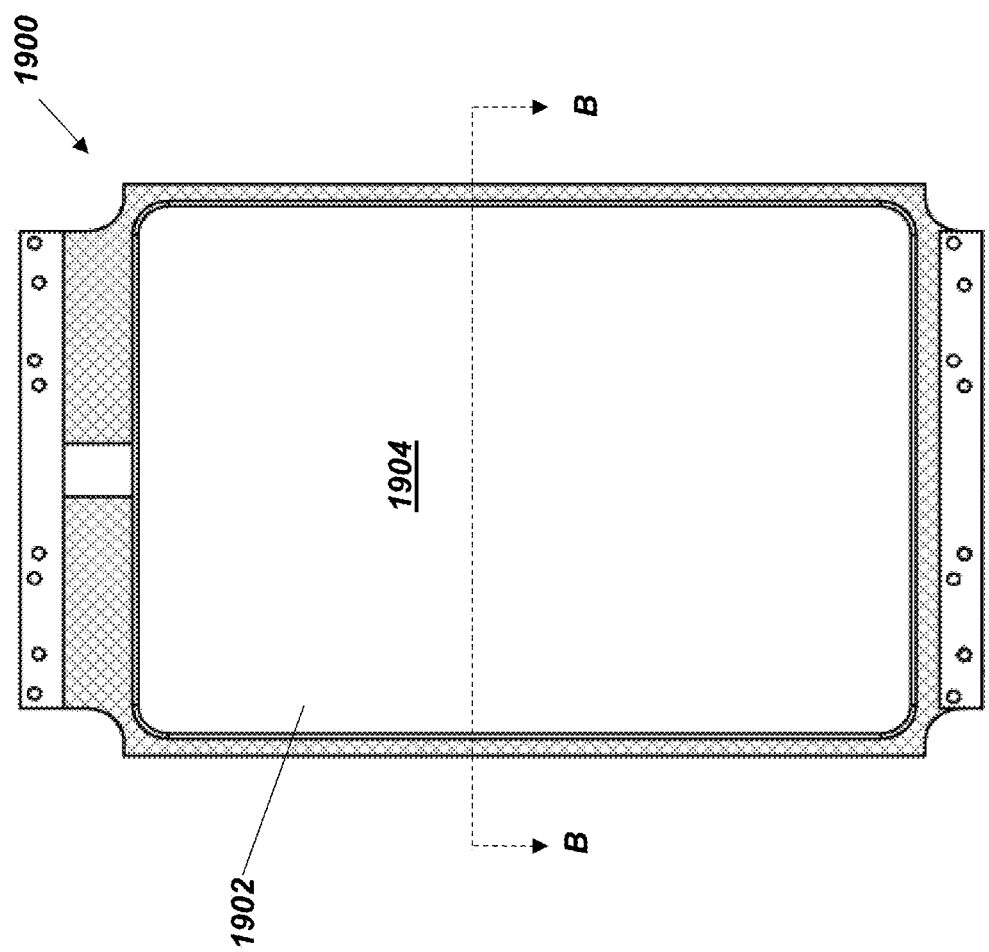
FIG. 18A is a front view of an embodiment of a heating cushion.
Figure 18B:
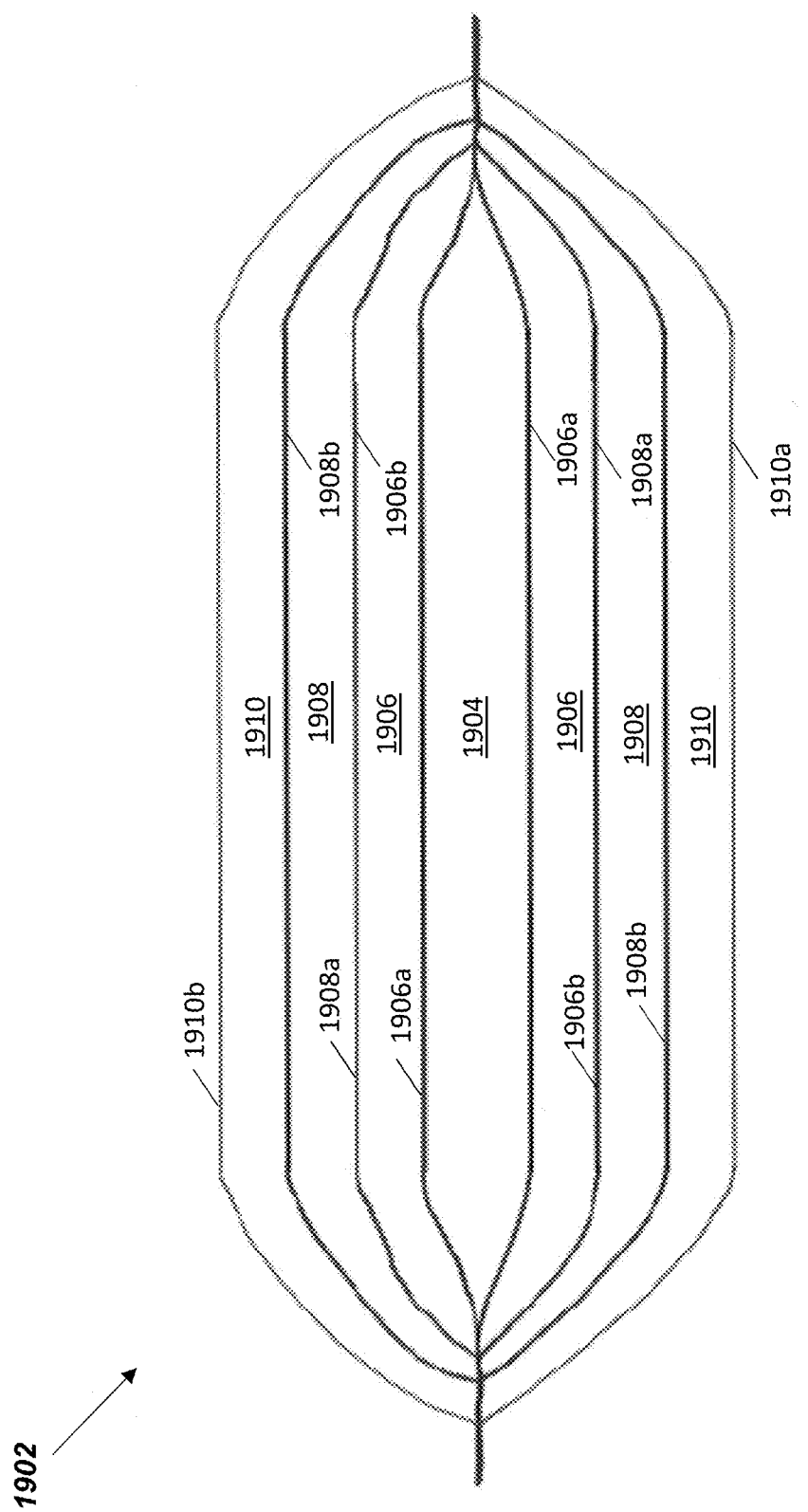
FIG. 18B is a cross-sectional view of the heating cushion of FIG. 18B taken at line B-B the facing a common side.

In other embodiments, the heating cushion can be formed of a single layer or multiple layers (e.g., two or more layers). For example, as shown in FIG. 18A-18B, a heating cushion 1900 can include a multi-layered cushion body 1902 defining a compartment 1904 therein that is configured to house a fluid. In this illustrated embodiment, the multi-layered cushion body 1902 includes an inner layer 1906, a first barrier layer 1908, and a second barrier layer 1910. Each layer can have a variety of thickness. In some embodiments, each layer can have a thickness from about 1 μm to 100 μm about 1 μm to 35 μm about 1 μm to 33 μm about 1 μm to 20 μm or about 10 μm to 15 μm.

The inner layer 1906 has a first surface 1906a and a second surface 1906b, in which the compartment 1904 is bounded by the first surface 1906a. The inner layer can formed of any suitable flexible material. Non-limiting examples of suitable flexible materials include polyethylene, other polymeric materials having multi-axis flexibility, or any combination thereof.

The first barrier layer 1908 has a first surface 1908a and a second surface 1908b. The first barrier layer 1908 is configured to substantially prevent egress of fluid disposed in the compartment 1904 and/or vapor generated within the compartment 1904 during use. In this illustrated embodiment, the first barrier layer 1908 is disposed onto the second surface 1906b of the inner layer 1906. In other embodiments, the first barrier layer 1908 can be disposed onto a portion of the second surface 1906b of the inner layer 1906. Non-limiting example of suitable materials for the first barrier layer include methyl aluminum oxide, and the like, and any combination thereof.

The second barrier layer 1910 is configured to inhibit the inner and first barrier layers 1906, 1908 from melting. For example, the second barrier layer 1910 can inhibit melting of the inner and first barrier layers 1906, 1908 in response to the generation of a hot spot or spots between the heater and the heating cushion 1900. A hot spot or spots can be generated, for example, as a result of pressure created by a frozen enclosed biological substance, which can expand the heating cushion. As a result, this expansion can further compress the heating cushion against the heater, and thus generate a hot spot or spots at their interface. Further, the second barrier layer 1910 is configured to permit transfer of a relatively high flux of heat therethrough from a fluid disposed within the compartment 1904 of the multi-layered heating cushion body 1902.

In this illustrated embodiment, the second barrier layer 1910 is disposed onto the second surface 1908b of the first barrier layer 1908 such that a first portion 1910a of the second barrier layer 1910 contacts a heater and a second portion 1910b of the second barrier layer 1910 contacts an enclosed biological substance received within a cavity formed between heating assemblies, like first and second heating assemblies 400, 500 shown in FIGS. 1A-1B and 3-4 or first and third heating assemblies 1208, 1242 shown in FIGS. 11C-13B. In other embodiments, the second barrier layer 1910 can be disposed onto a portion of the second surface 1908b of the first barrier layer 1908.

The second barrier layer 1910 can have a melting point that is greater than the melting points of the inner and first barrier layers 1906, 1908. For example, in some embodiments, the second barrier layer 1910 has a melting point from about from about 80° C. to 200° C. Non-limiting examples of suitable materials for the second barrier layer 1910 include biaxially oriented polyamide (BOPA), or the like, or any combination thereof.

In certain embodiments, a multi-layered cushion body can include two laminates partially sealed, e.g. heated sealed, together. Each laminate can have an inner layer, like inner layer 1906 as shown in FIG. 18B, a first barrier layer, like first barrier layer 1908 as shown in FIG. 18B, and a second barrier layer, like second barrier layer 1910 as shown in FIG. 18B. As such, a portion of the inner layers can form a compartment defined within the cushion body, and the second barrier layers can form opposing outer surfaces of the cushion body. Each laminate can have a variety of thickness. For example, in some embodiments, each laminate can have a thickness from about 1 μm to 50 μm, or from about 1 μm to 40 μm. In other embodiments, each laminate can have a thickness of about 40 μm or of about 50 μm.

Bag Assembly

Figure 5B:
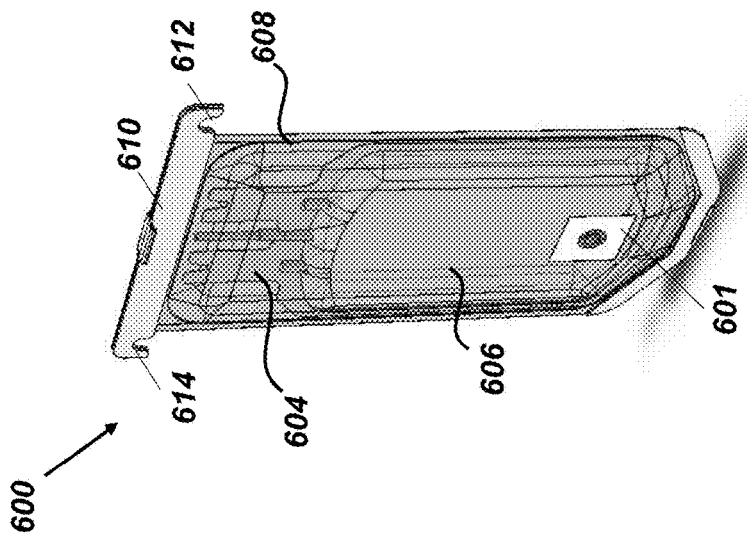
FIG. 5B is an isometric view illustrating the bag assembly of FIG. 5A.
Figure 5A:
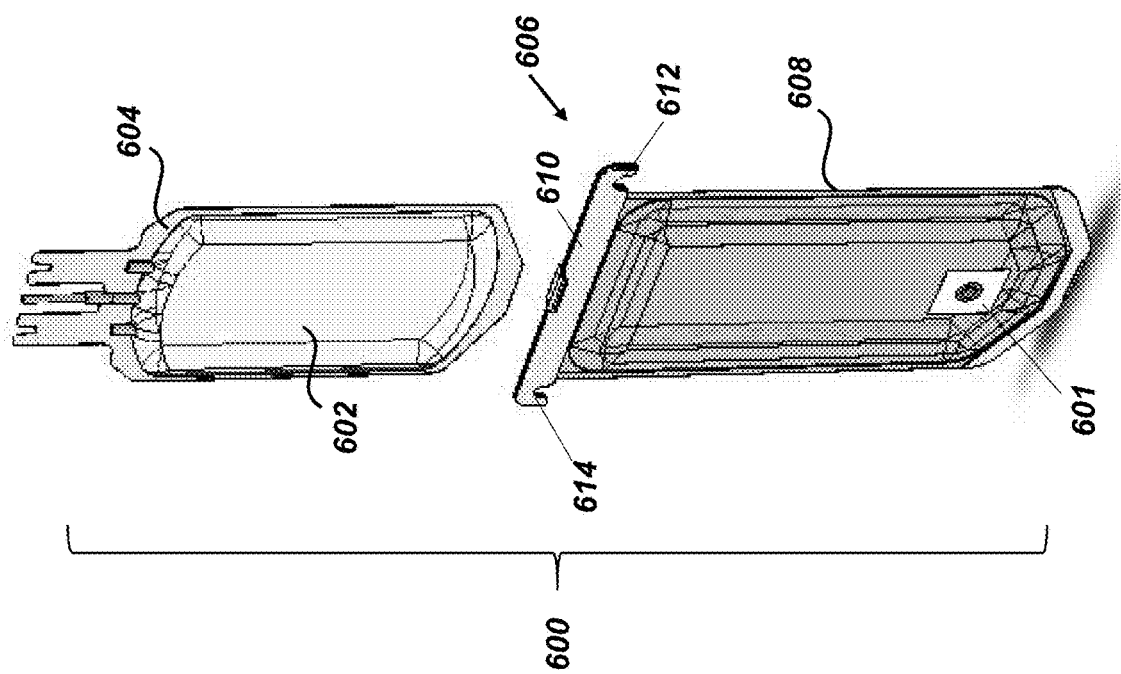
FIG. 5A is an exploded view illustrating the bag assembly of FIGS. 1A-1B.

The bag assembly can also have a variety of configurations, and various bags can be used with the systems and methods disclosed herein. FIGS. 5A-5B illustrate one exemplary embodiment of a bag assembly 600. As shown, the bag assembly includes a biological substance 602 disposed in the enclosure 604 which is disposed within the overwrap bag 606. The overwrap bag 606 can be in the form of a reversibly sealable pouch dimensioned to receive the enclosure 604. In the event that the enclosure 604 leaks or ruptures during the thawing process, the overwrap bag 606 can isolate the biological substance 602, thereby preventing contamination of the dry thawing system.

The overwrap bag 606 can be configured to satisfy one or more functional requirements. In one aspect, the overwrap bag 606 can possess a relatively high thermal conductivity to facilitate heating of the enclosure 604 and biological substance 602 contained therein. In another aspect, the overwrap bag 606 can be configured to withstand temperatures within a predetermined temperature range (e.g., about −196° C. to about 40° C.). In a further aspect, the overwrap bag 606 can be disposable after a single use or formed from materials capable of being sterilized and reused in accordance with the requirements of domestic and/or international governing organizations and regulatory bodies. In an additional aspect, the overwrap bag 606 can be configured to provide anti-microbial properties, whether intrinsically or through the use of coatings or additives. Examples of materials forming the overwrap bag 606 can include plastics, metals, and combinations thereof.

Figure 7:
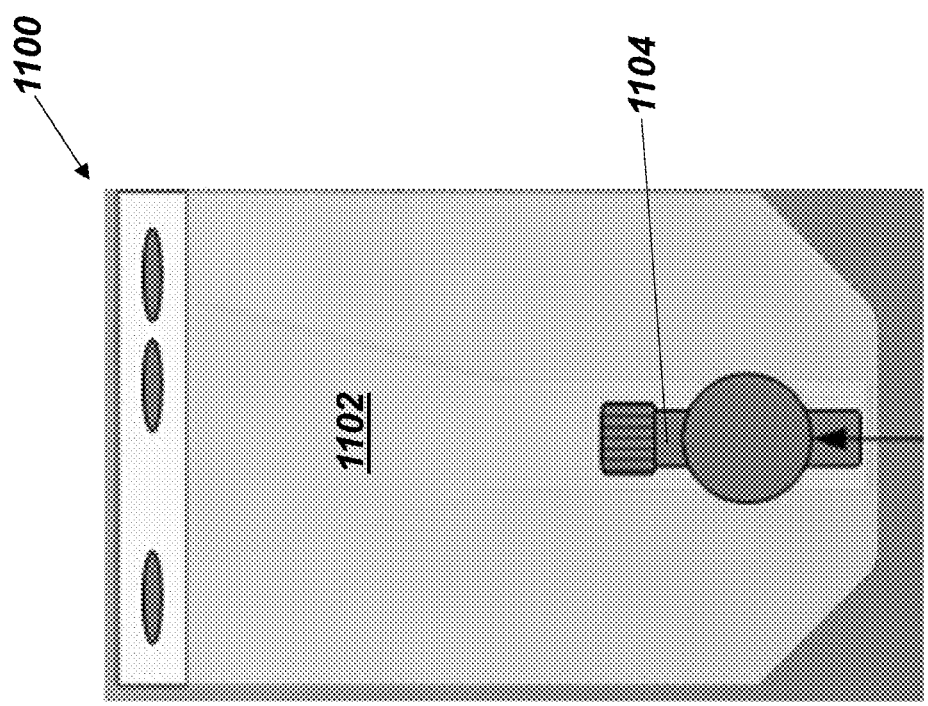
FIG. 7 is a front side view of an another embodiment of an overwrap bag having a compartment with a second funnel configuration.
Figure 6:
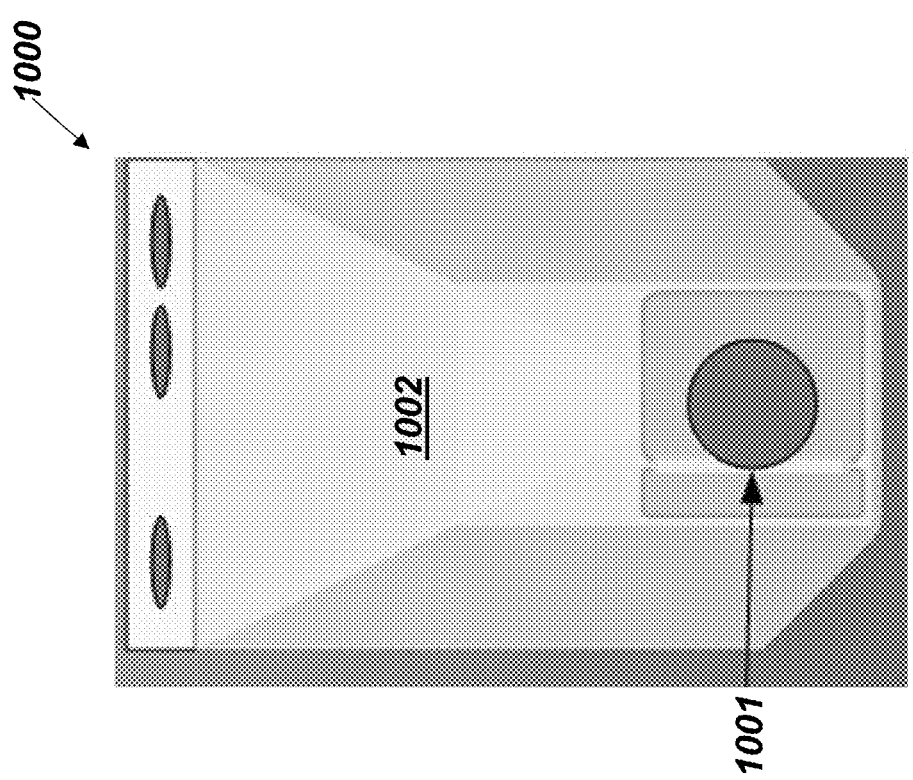
FIG. 6 is a front side view of an embodiment of an overwrap bag having a compartment with a first funnel configuration.

The overwrap bag 606 can be soft, semi-rigid, or rigid and dimensioned to receive enclosures of any size. For example, as shown in FIGS. 6 and 7, a compartment or cavity 1002, 1102 of an overwrap bag 1000, 1100 can be dimensioned so as to have a funnel-shaped configuration. Further, in some embodiments, an overwrap bag can include a RFID (e.g., mounted to an outer surface), such as RFID tag 601 mounted to overwrap bag 606 as shown in FIGS. 1A-1B and 5A-5B, RFID tag 1001 mounted to overwrap bag 1000 shown in FIG. 6, and RFID tag 1101 mounted to overwrap bag 1100 as shown in FIG. 7. Exemplary embodiments of RFID tags are described in more detail in International Patent Application No. WO 2016/023034, which is hereby incorporated by reference in its entirety.

In certain embodiments, the enclosure can be a blood bag having a volume within the range from about 100 mL to about 500 mL. In other embodiments, as shown in FIG. 7, the enclosure 1104 can be in the form of a vial, which can contain a biological substance such as blood, cells, sperm, tissue, and the like. While the volume of the vial will be dependent at least upon the dimensions of the overwrap bag, in some embodiments, the vial can have a volume in a range of about 3 mL to about 10 mL. The volume of the heating cushion (e.g., like heating cushions 404, 504) and/or the elastic properties (e.g., elastic modulus) of the heating cushion (e.g., like heating cushions 404, 504) can be configured to accommodate the shape and volume of the enclosure, regardless of size, ensuring contact between the enclosure and the heating cushions and good conduction of heat between the heating cushions and the biological substance.

The overwrap bag 606 can include an overwrap body 608 and a cover 610 attached to one end of the overwrap body 608 (e.g., a top end). The cover 610 can be configured to open and close, allowing insertion of the enclosure 604 within the overwrap body 608 when open and hermetic sealing of the overwrap body 608 when closed for protection of enclosures, like enclosure 604, placed therein. In certain embodiments, the cover 610 can be formed from a biologically inert material, such as an epoxy. The cover 610 can further include a closure mechanism to form the hermetic seal. The closure mechanism can be embedded and/or integrally formed with the cover 610. Examples of closure mechanisms can include interlocking grooves and ridges, reversible adhesives, magnetic-based closures, etc.

The cover 610 can be configured to engage the chamber frame 202 for support of the bag assembly 600. As an example, the cover 610 can be formed in the shape of hooks 612, 614 at opposed lateral ends. The hooks 612, 614 can rest on mounting posts 228, 230 positioned adjacent the top portion 204 of the chamber frame 202 to suspend the bag assembly 600 in place when inserted within the dry thawing chamber 200. In certain embodiments, the overwrap bag 606 can be in the form of an overwrap bag as discussed in previously mentioned International Patent Application No. WO 2016/023034, which is incorporated herein in its entirety.

Figure 5C:
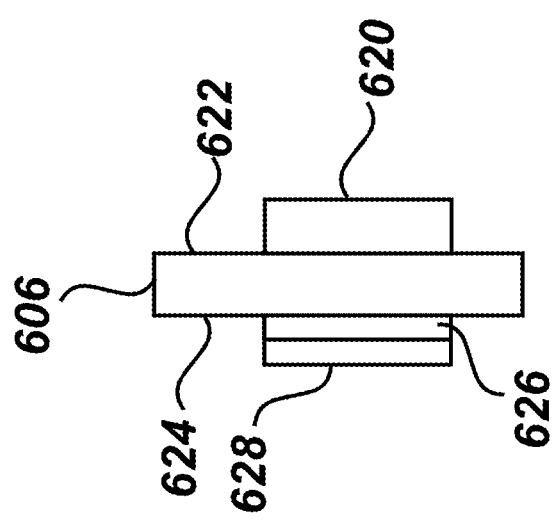
FIG. 5C is a cross-sectional view illustrating an exemplary portion of the overwrap bag of FIGS. 5A-5B configured for thermal isolation of a temperature sensor.

The overwrap bag 606 can be further configured to facilitate temperature measurements of the enclosed biological substance 602. FIG. 5C illustrates a cross-sectional view of an exemplary portion of the overwrap bag 606, where a contact temperature sensor 620 is positioned on an inward facing surface 622 of the overwrap bag 606. Opposing the temperature sensor 620 on an exterior facing surface 624 of the overwrap bag 606 is an encapsulated air pocket 626. The air pocket 626 can act as an insulator, promoting thermal isolation of the temperature sensor 620 from the environment external to the overwrap bag 606. In further embodiments, the encapsulation 628 can be formed from a material having a low thermal conductivity, further promoting thermal isolation of the temperature sensor 620.

In further embodiments (not shown), a dry thawing chamber, like dry thawing chamber 200 shown in FIGS. 1A-1B, can include a vacuum mechanism, such as a vacuum pump in fluid communication with an interior of the overwrap body (e.g., via a one-way valve). When the chamber door is placed in the closed position, the vacuum pump can be activated to remove air from the interior of the overwrap body and create a partial vacuum within the overwrap body. By reducing the pressure within the overwrap body, as compared to the ambient pressure outside the overwrap body, the overwrap body can be urged into contact with the enclosure by the ambient pressure. In this manner, the accuracy of temperature measurements acquired by temperature sensor(s) mounted to the overwrap body can be improved.

Agitator

As indicated above, an agitator can be disposed within the chamber frame for agitating an enclosed biological substance during heating. The agitator can have a variety of configurations. FIGS. 8A-8D illustrate one exemplary embodiment of an agitation device 224 configured to agitate the enclosed biological substance (not shown) contained within the bag assembly 600 placed within the dry thawing chamber 200. As shown, the agitation device 224 can be mounted to the chamber frame 202 and it can include a motor 702 and a cam 704. The cam 704 is positioned in contact with the cover 412 of the first heating assembly 400 at a predetermined distance from the first pivot 426. When the agitation device 224 is activated, the motor 702 causes the cam 704 to rotate and make sliding contact with the cover 412. This contact imparts reciprocal motion to the first heating assembly 400 and causes the first heating assembly 400 to reversibly pivot about the first pivot mount 232. That is, opposing ends (e.g., top and bottom ends) of the first heating assembly 400 can oscillate relative to the chamber frame 202.

Figure 8B:
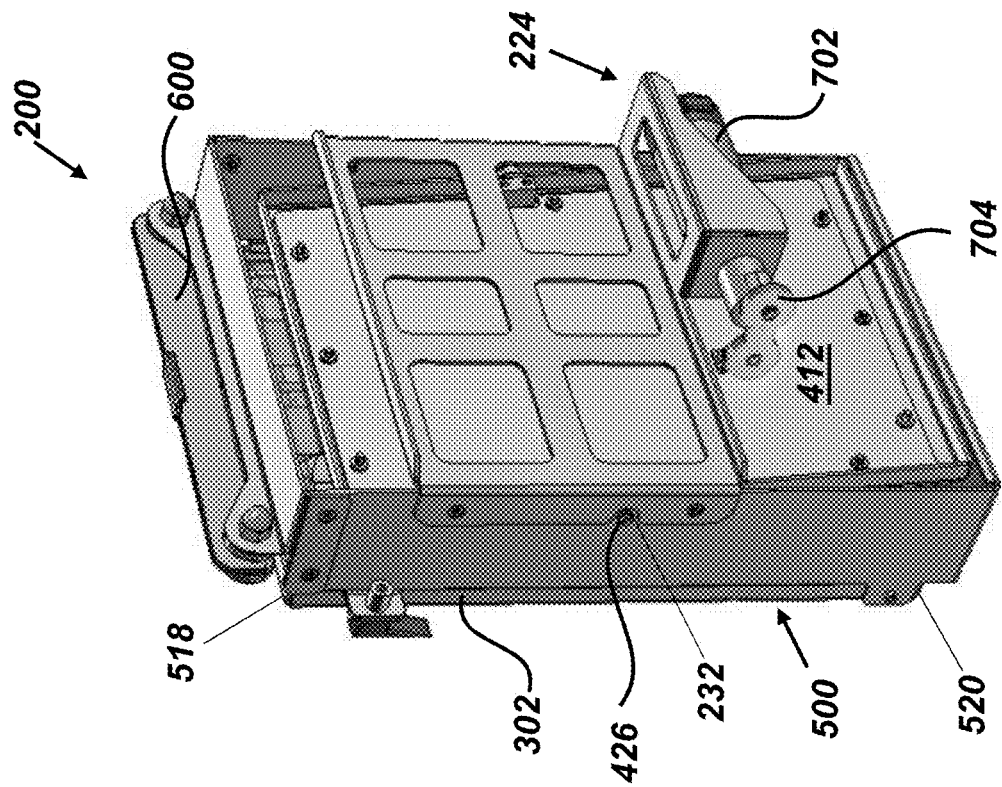
FIG. 8B is a rear-facing isometric view of the dry thawing chamber of FIGS. 1A-1B illustrating the agitation device in a second position engaging the first heating assembly.
Figure 8A:
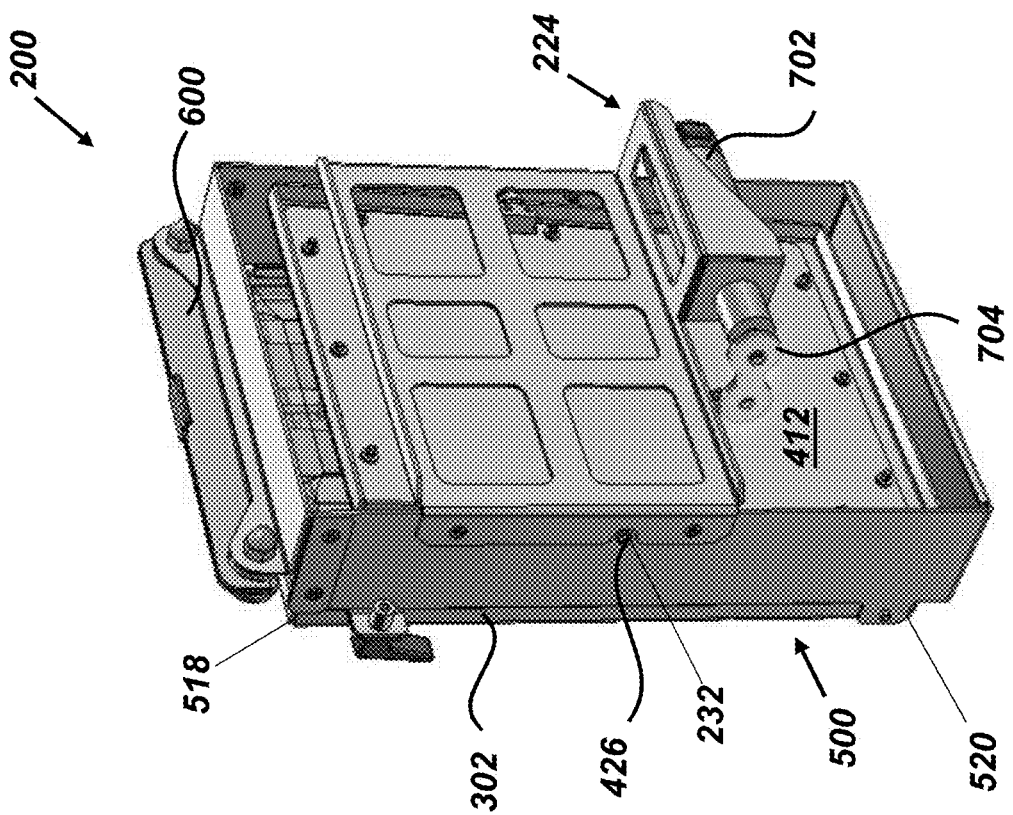
FIG. 8A is a rear-facing isometric view of the dry thawing chamber of FIGS. 1A-1B illustrating the agitation device in a first position engaging the first heating assembly.
Figure 8D:
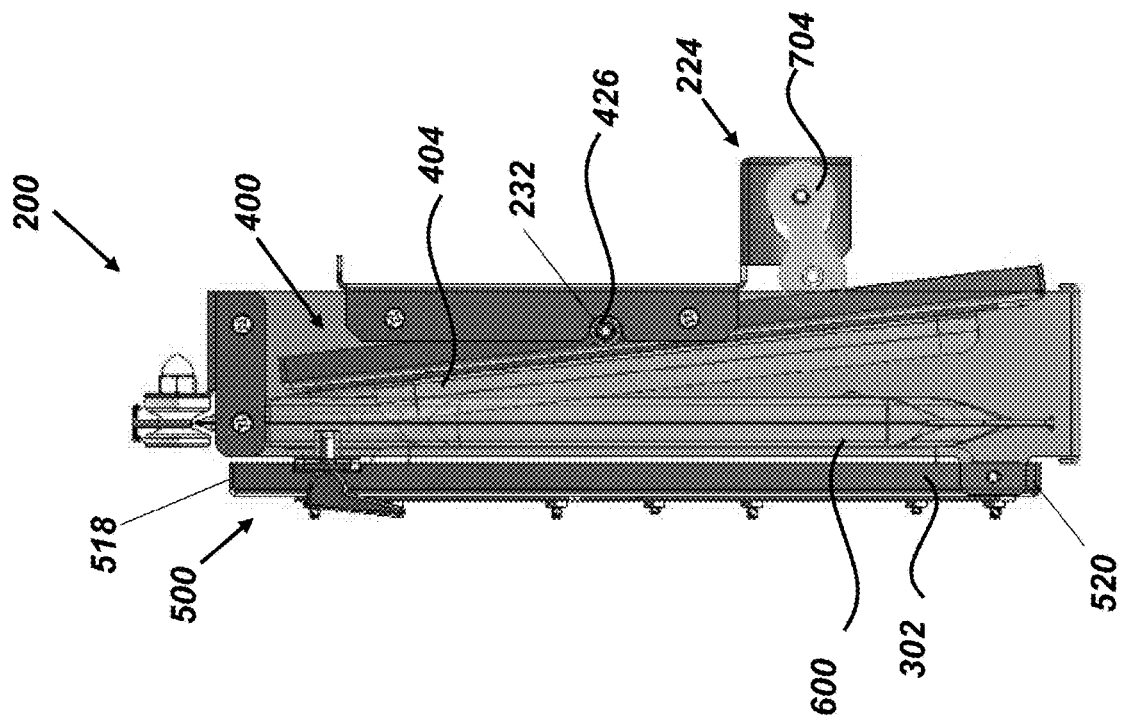
FIG. 8D is a side view of the dry thawing chamber of FIG. 8B.
Figure 8C:
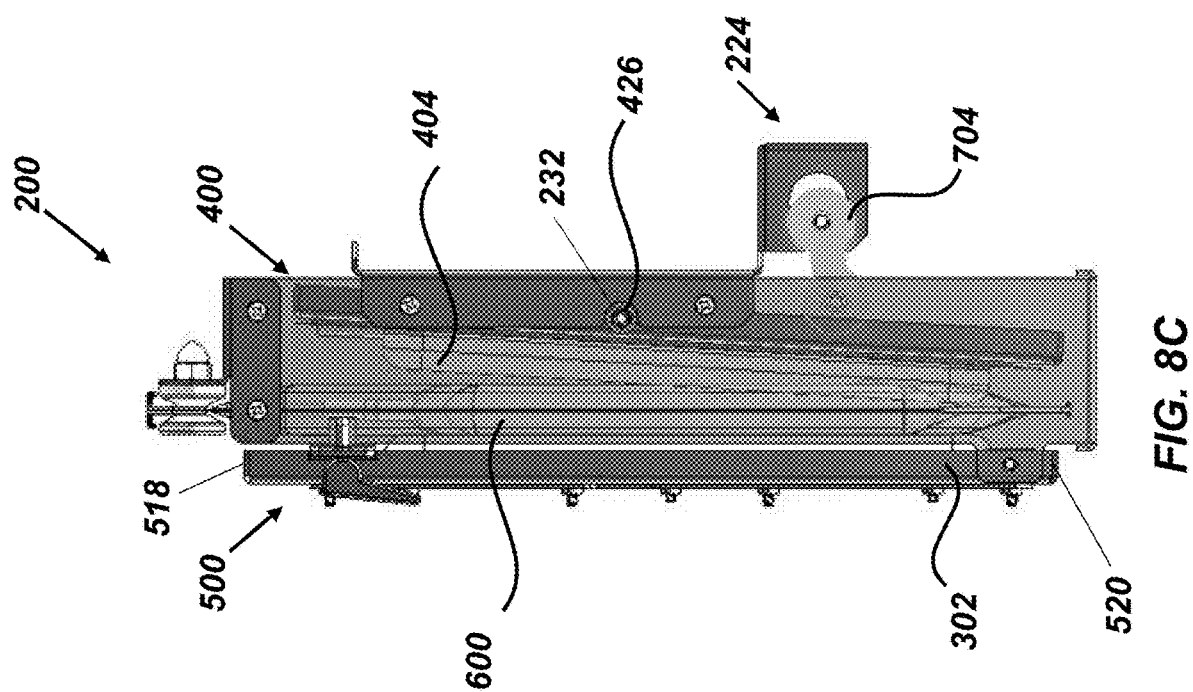
FIG. 8C is a side view of the dry thawing chamber of FIG. 8A.

Because the second heating assembly 500 is fixed in place when in the closed position, the pivoting motion of the first heating assembly 400 alternates application of a compressive force against opposed ends of the bag assembly 600 (e.g., top and bottom ends) and agitates the enclosed biological substance (not shown) as it thaws. As shown in FIGS. 8A and 8C, when the cam 704 extends towards the first heating assembly 400, it urges the first heating assembly 400 to pivot clockwise, towards a bottom end 520 of the second heating assembly 500. A bag assembly 600 positioned between the first and second heating assemblies 400, 500 thus experiences a compressive force at its bottom end that urges the enclosed biological substance (not shown) upwards. As further shown in FIGS. 8B and 8D, when the cam 704 retracts away from the first heating assembly 400, the enclosed biological substance (not shown) is no longer urged towards the top portion 204 of the chamber frame 202 and moves downwards, towards the bottom portion 206 of the chamber frame 202, under the force of gravity. In response, the first heating assembly 400 pivots counter-clockwise, towards a top end 518 of the second heating assembly 500. The bag assembly 600 positioned between the first and second heating assemblies 400, 500 thus experiences a compressive force at its top end that further urges the enclosed biological substance (not shown) downwards.

The frequency and magnitude at which the agitation device 224 drives the first heating assembly 400 to alternate application of compressive force against opposed ends of the bag assembly 600 can be controlled by the controller (e.g., controller 104). In one example, the RPM of the motor 702 of the agitation device 224 can be increased to increase the frequency of agitation and decreased to decrease the frequency of the agitation. In another example, the amplitude of the agitation can be related to the radius of the cam 704 of the agitation device 224.

Housing

Figure 9B:
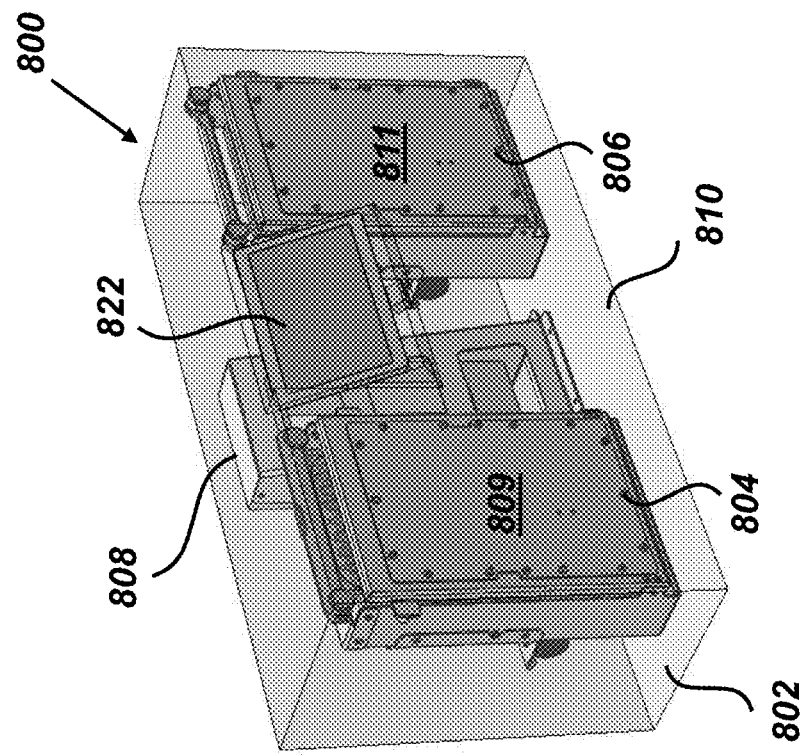
FIG. 9B is a partially transparent perspective view of the dry thawing system of FIG. 9A.
Figure 9A:
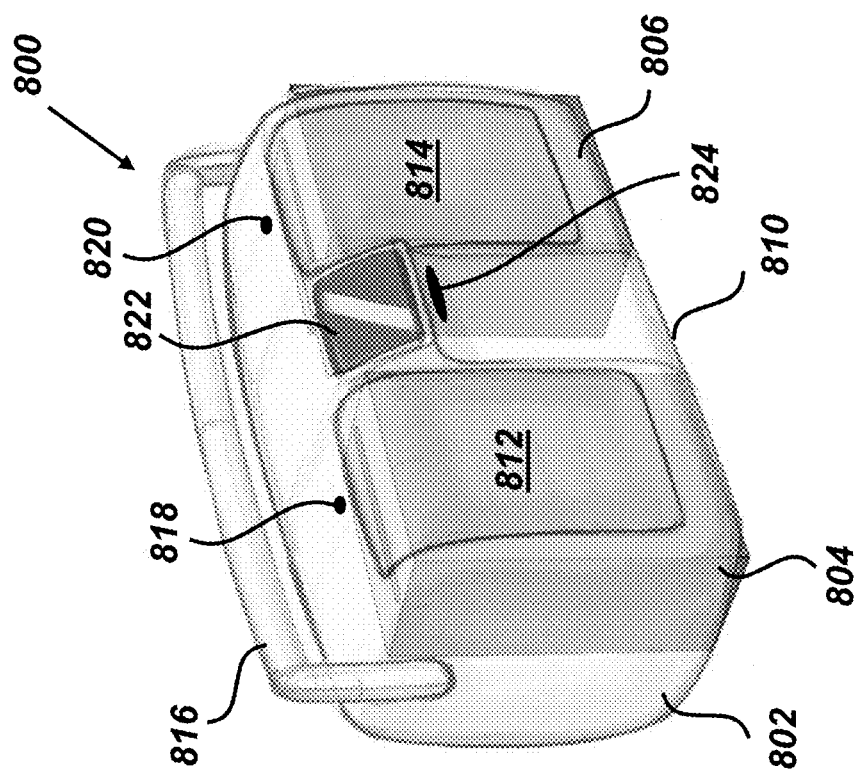
FIG. 9A is a perspective view of another embodiment of a dry thawing system including two dry thawing chambers facing a common side.

One or more of the aforementioned dry thawing chambers can be contained within a housing, such as a portable housing. FIGS. 9A-9B illustrate a first exemplary embodiment of a dry thawing system 800 including a housing or chassis 802 containing a first dry thawing chamber 804, like dry thawing chamber 200 shown in FIGS. 1A-2D and 8A-8D, and a second dry thawing chamber 806, like dry thawing chamber 200 shown in FIGS. 1A-2D and 8A-8D, in communication with a power supply 808. The power supply 808 can be configured to supply power to the first and second dry thawing chambers 804, 806. Each of the dry thawing chambers 804, 806 can be arranged with chamber doors 809, 811 facing a common side of the chassis 802 (e.g., a front side 810). A first door 812 and a second door 814 of the chassis 802 can be coupled to the chamber door 809 of the first dry thawing chamber 804 and the chamber door 811 of the second dry thawing chamber 806, respectively, allowing an operator to insert or remove a bag assembly, like bag assembly 600 shown in FIGS. 1A-1B and 5A-5B, from respective dry thawing chambers. A handle 816 is also coupled to the chassis 802, allowing the dry thawing system 800 to be easily carried. The handle 816 can be configured to fold into a recess within the chassis 802 when not being carried.

In some embodiments, an indicator light can be provided to indicate a status of a dry thawing chamber. For example, as shown in FIG. 9A, a first indicator light 818 can be provided to indicate a status of the first dry thawing chamber 804 and a second indicator light 820 can be provided to indicate a status of the second dry thawing chamber 806, as discussed below. Fewer (e.g., one) or more (e.g., three or more) indicator lights can be provided according to how many dry thawing chambers are contained within a dry thawing system.

The user interface 822 can be mounted to a common side (e.g. front side 810) of the chassis 802 and it can receive power from the power supply 808. In certain embodiments, the user interface 822 can also include a controller. In alternative embodiments, the user interface 822 can be configured to communicate with a remote controller.

The user interface 822 can, for example, be a cathode ray tube (CRT) and/or a liquid crystal display (LCD) monitor. The interaction with an operator user can, for example, be a display of information to the operator and a keyboard and a pointing device (e.g., a mouse, trackball, optical or resistive touch screen, etc.) by which the operator can provide input to the computer (e.g., interact with a user interface element). Other kinds of devices can be used to provide for interaction with an operator. Other devices can, for example, be feedback provided to the operator in any form of sensory feedback (e.g., visual feedback, auditory feedback, or tactile feedback). Input from the operator can, for example, be received in any form, including acoustic, speech, and/or tactile input.

The controller can be configured to provide commands to a heater, like heater 408 and/or heater 508 shown in FIGS. 1A-4, and an agitation device, like agitation device 224 shown in FIGS. 1A-1B and 8A-8D, in accordance with a predetermined thawing program. The predetermined thawing program can include a target temperature-time response of at least one heating cushion, like heating cushions 404, 504 shown in FIGS. 1A-4, and an enclosed biological substance, like enclosed biological substance 602 shown in FIGS. 1A-1B and 5A-5B. As an example, an operator can employ the user interface device to select the predetermined thawing program from a list of predetermined thawing programs stored by a data storage device in communication with the controller.

In other embodiments, the predetermined thawing program can be selected automatically by the controller from a list of predetermined thawing programs. As an example, the predetermined thawing program can be selected by the controller based upon a volume or weight of the enclosed biological substance.

The controller can receive the volume and/or weight of the enclosed biological substance in a variety of ways. In one aspect, the controller can receive the volume and/or weight from manual input by an operator using the user interface device. In another aspect, the user interface 822 can include an input device 824, such as a barcode reader or other automated input device (e.g., an optical character reader, a radiofrequency tag reader, etc.) and the input device can read the volume of the enclosed biological substance from markings on enclosure itself representing the volume and/or weight (e.g., a barcode, text) or a device secured to the enclosure (e.g., an RFID tag) that electronically stores data including the volume and/or weight In a further embodiment, the controller can obtain the volume and/or weight from weight measurements of the overwrap bag when positioned in the dry thawing chamber, as discussed above.

The controller can be implemented in digital electronic circuitry, in computer hardware, firmware, and/or software. The implementation can be as a computer program product. The implementation can, for example, be in a machine-readable storage device, for execution by, or to control the operation of, data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

Figure 10B:
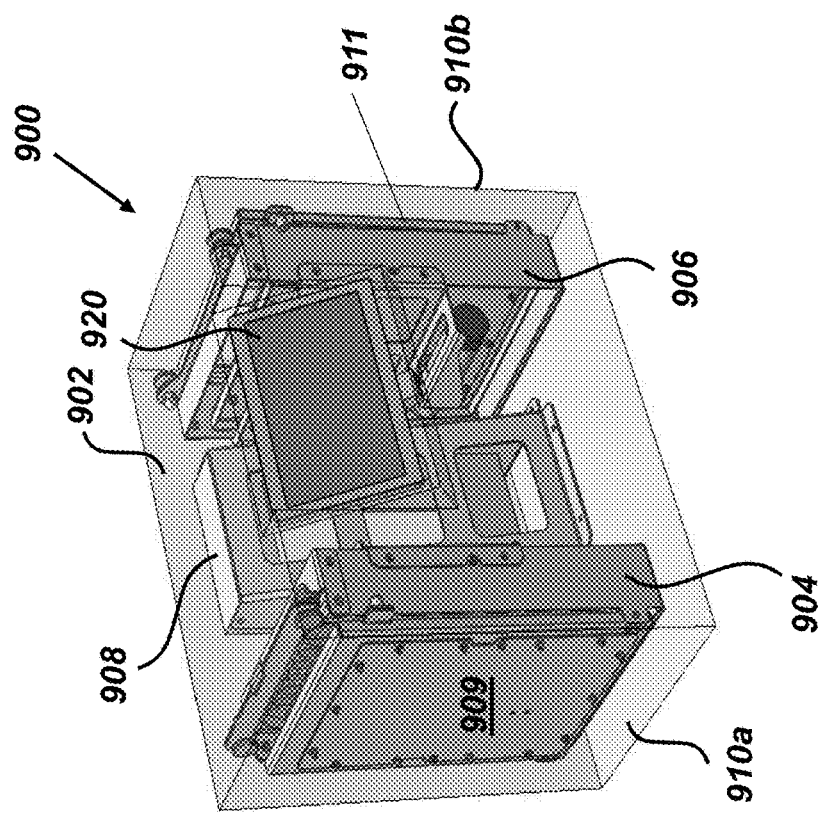
FIG. 10B is a partially transparent perspective view of the dry thawing system of FIG. 10A.
Figure 10A:
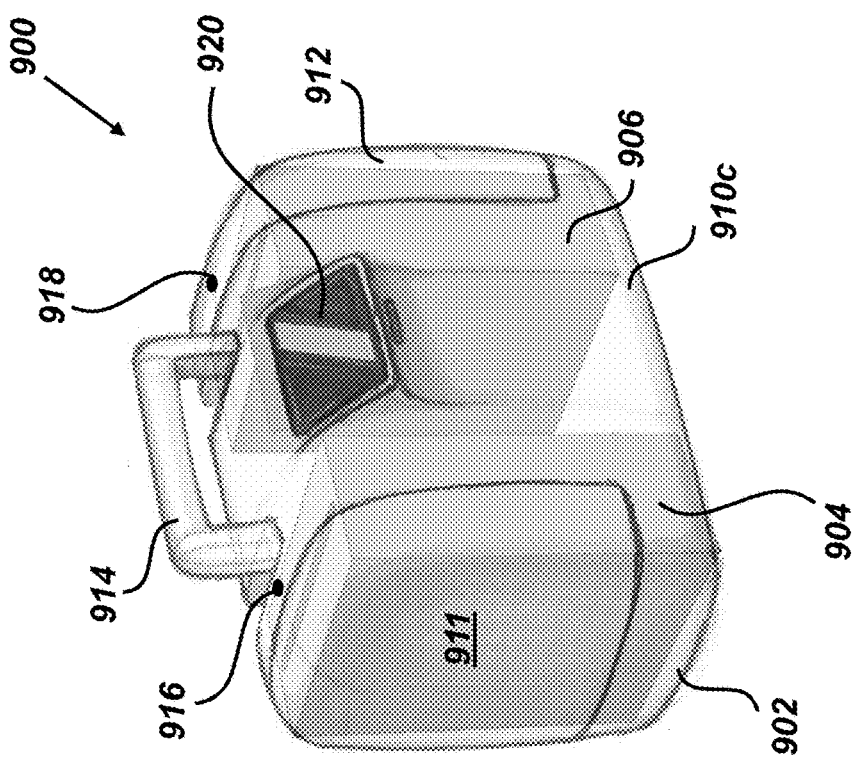
FIG. 10A is a perspective view of another embodiment of a dry thawing system including two dry thawing chambers facing opposed sides.

FIGS. 10A-10B illustrate a second exemplary embodiment of a dry thawing system 900 including a chassis 902 containing two dry thawing chambers 904, 906 in communication with a power supply 908. Each of the dry thawing chambers 904, 906 are arranged with chamber doors 909, 911 facing opposed sides of the chassis (e.g., left and right sides 910a, 910b). First and second doors 911, 912 of the chassis 902 can be coupled to the first and second chamber doors 909, 911, respectively, allowing an operator to insert or remove a bag assembly, like bag assembly 600 shown in FIGS. 1A-1B and FIGS. 5A-5B, from respective dry thawing chambers. The user interface 920 (e.g., a touch-screen display) can also be mounted to another side of the chassis 902 (e.g., a front side 910*c*), in between the two dry thawing chambers. The second dry thawing system embodiment can also include a handle 914, indicator lights 916, 918, a user interface 920, a controller similar to the first dry thawing system 800 as shown in FIGS. 9A-9B.

In certain embodiments, the portable dry thawing systems 800, 900 of FIGS. 9A-9B and 10A-10B can include dry thawing chambers that are removable from their respective housings. As an example, each dry thawing chamber can be received within a socket (not shown) formed within its housing. A wiring harness or electrical contacts can be positioned within the sockets and configured to reversibly mate with a corresponding wiring harness or electrical contacts of the dry thawing chamber. Power, command signals, and measured temperatures can be transmitted between the power supply, controller, and dry thawing chamber via the wiring harnesses and/or electrical contacts. So configured, dry thawing chambers can be removed from the housing for sterilization, disinfection, repair, and/or replacement.

Figure 11B:
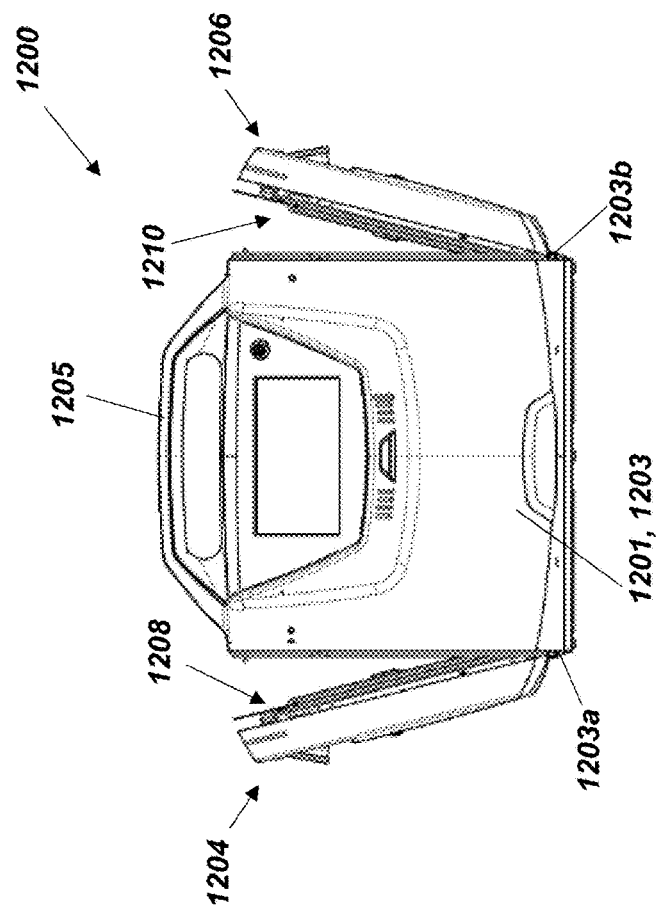
FIG. 11B is a perspective of the dry thawing system of FIG. 11A, illustrating the dry thawing system in an open configuration.
Figure 11A:
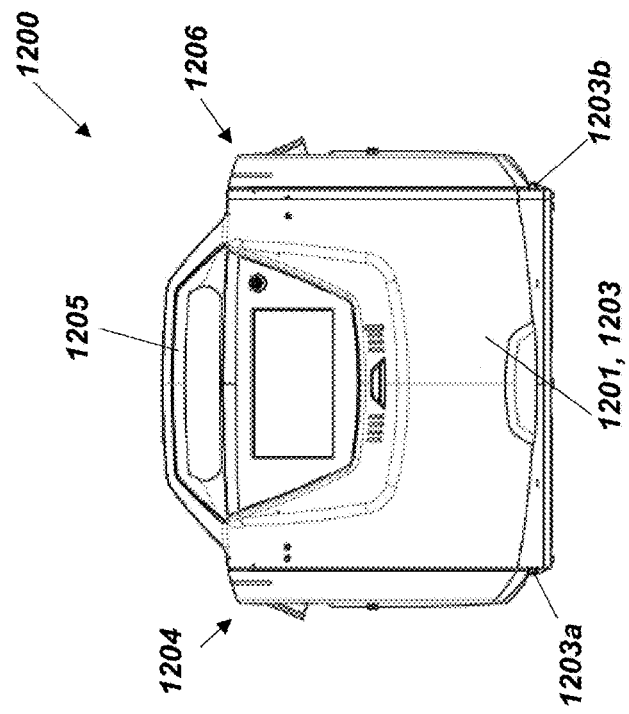
FIG. 11A is a perspective view of another embodiment of a dry thawing system including first and second dry thawing chambers, illustrating the dry thawing system in a closed configuration.
Figure 11C:
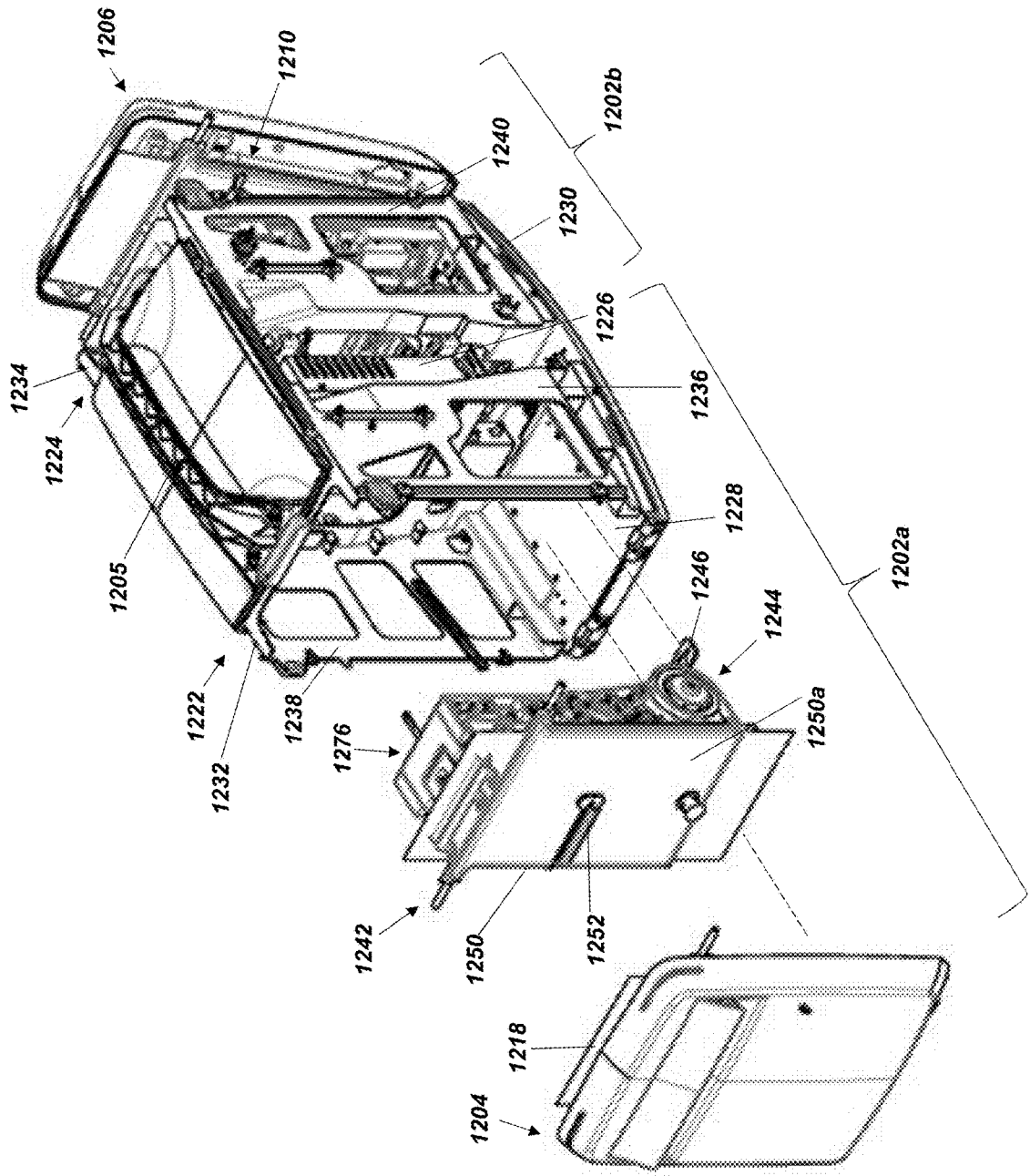
FIG. 11C is a partial exploded view of a portion of the dry thawing system of FIG. 11B, illustrating the first and second dry thawing chambers.

FIGS. 11A-11C illustrate another embodiment of a dry thawing system 1200 that includes a housing or chassis 1201 containing a first dry thawing chamber 1202*a* and a second dry thawing chamber 1202*b* in communication with a power supply 1226. The chassis 1201 has a main body 1203 with first and second opposing, doors 1204 and 1206 pivotally mounted at first and second ends 1203*a*, 1203*b* thereof. A handle 1205 is also coupled to the chassis 1201, allowing the dry thawing system 1200 to be easily carried.

The first and second doors 1204, 1206 serve as a chamber door of the first and second dry thawing chambers 1202*a*, 1202*b* 1203*b*, respectively, thereby allowing an operator to insert or remove an enclosed biological substance from respective dry thawing chambers. Each first and second doors 1204, 1206 has a first heating assembly 1208 and a second heating assembly 1210, respectively, coupled thereto. Each door 1204, 1206 is structurally similar and each first and second heating assemblies 1208, 1210 is structurally similar, and therefore, for the sake of simplicity, the following description is with respect to the first door 1204 and the first heating assembly 1208 coupled thereto. A person skilled in the art will understand, however, that the following discussion is also applicable to the second door 1206 and the second heating assembly 1210 coupled thereto.

Figure 12:
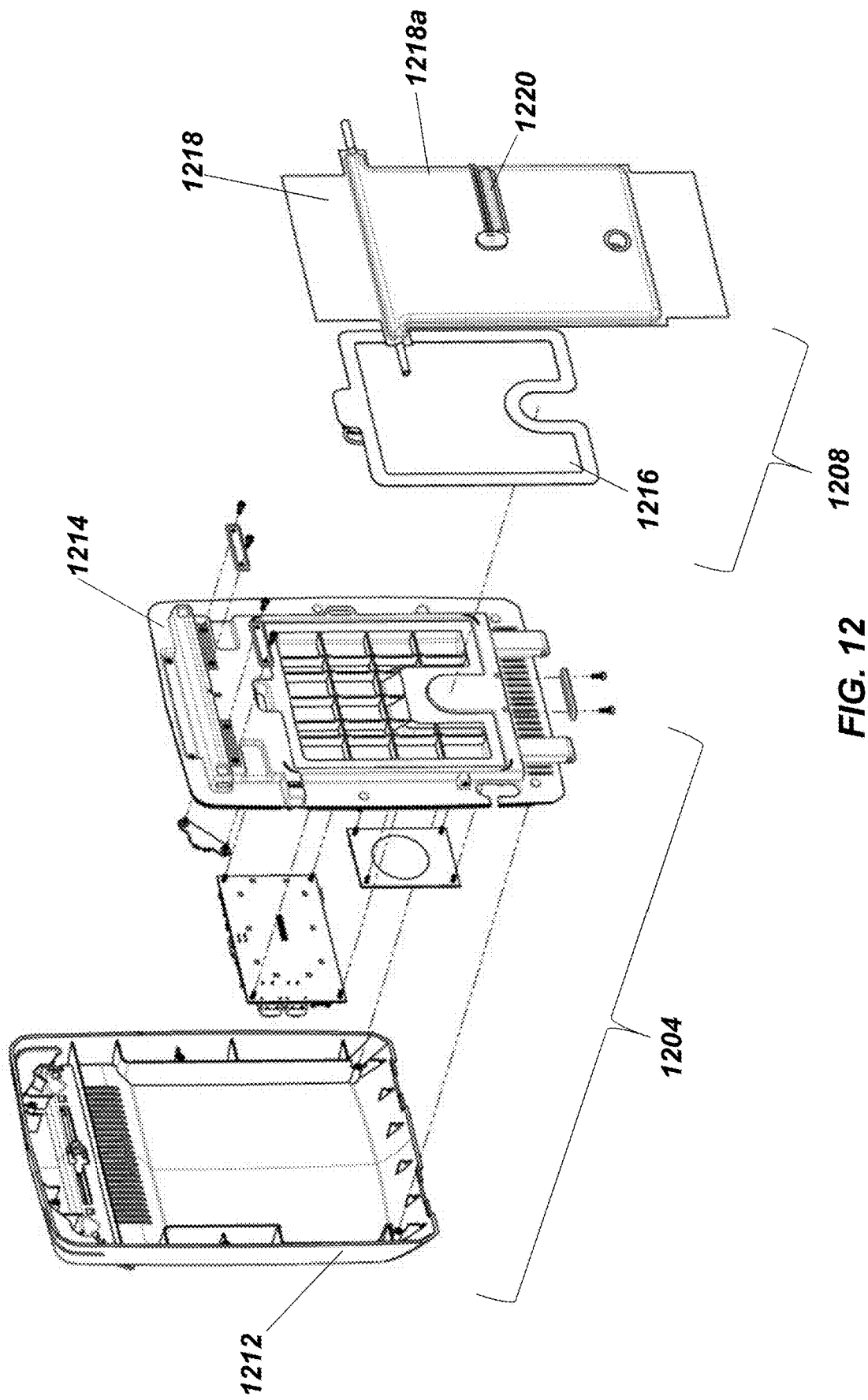
FIG. 12 is a partial exploded view of a first chamber door and a first heating assembly of the first dry thawing chamber of FIG. 11C.

As shown in more detail in FIG. 12, the first door 1204 includes an outer cover 1212 and inner cover 1214 The first heating assembly 1208 includes a heater 1216 and a heating cushion 1218 coupled thereto. While the heater 1216 can have a variety of configurations, as shown, the heater 1216 is in the form of a heater plate. At least one temperature sensor 1220 is coupled to an outer surface 1218*a* of the heating cushion 1218, and therefore in thermal communication therewith. As such, the illustrated at least one temperature sensor 1220 is configured to measure the temperature of the heating cushion 1218 during use. While the at least one temperature sensor 1220 can have a variety of configurations, in this illustrated embodiment, the at least one temperature sensor 1220 includes two temperature sensors, a thermistor, e.g., a NTC thermistor, and a thermocouple. In certain embodiments, one of the two temperature sensors can be in communication with the power supply 1226 that is configured to supply electrical power to the heater 1216. In such instances, when the measured temperature of the heating cushion 1218 exceeds a predetermined threshold temperature, the one of the two temperature sensors can transmit a failsafe signal to the power supply 1226 that is operative to cause the power supply 1226 upon receipt to terminate delivery of power to the heater 1216. In other embodiments, the at least one temperature sensor 1220 can include one temperature sensor or more than two temperature sensors.

Referring back to FIG. 11C, the first and second dry thawing chambers 1202*a*, 1202*b* contain first and second opposing chamber frames 1222, 1224, respectively, in which the power supply 1226 is positioned therebetween. As shown in FIG. 6C, the first and second chamber frames 1222, 1224 each have a base or bottom portion 1228, 1230 and a top portion 1232, 1234. The first chamber frame 1222 has first and second opposing sidewalls 1236, 1238, extending between its base or bottom portion 1228 and top portion 1232. The second chamber frame 1224 has a third sidewall 1240 and a fourth, opposing sidewall that is obscured in FIG. 11C, each extending between the base or bottom portion 1230 and top portion 1234. The first chamber frame 1222 has a third heating assembly 1242 that is pivotally mounted to a support frame 1244. The support frame 1244 is slidably mounted to a track 1246, which is shown in more detail in FIGS. 13A and 13B. While not shown, the track 1246 is fixedly mounted to the base or bottom portion 1228 of the first chamber frame 1222. As such, the support frame 1244 is configured to slidably move relative to the first chamber frame 1222.

Further, while obscured in FIG. 11C, the second chamber frame 1224 includes a fourth heating assembly, a second support frame, and a second track that are structurally similar to the third heating assembly 1242, the first support frame 1244, and the first track 1246 and together in a similar fashion. As such, for sake of simplicity, the following description is with respect to the third heating assembly 1242, the first support frame 1244, and the first track 1246, the first door 1204 and the first heating assembly 1208 coupled thereto. A person skilled in the art will understand, however, that the following discussion is also applicable to the fourth heating assembly, the second support frame, and the second track.

Figure 13A:
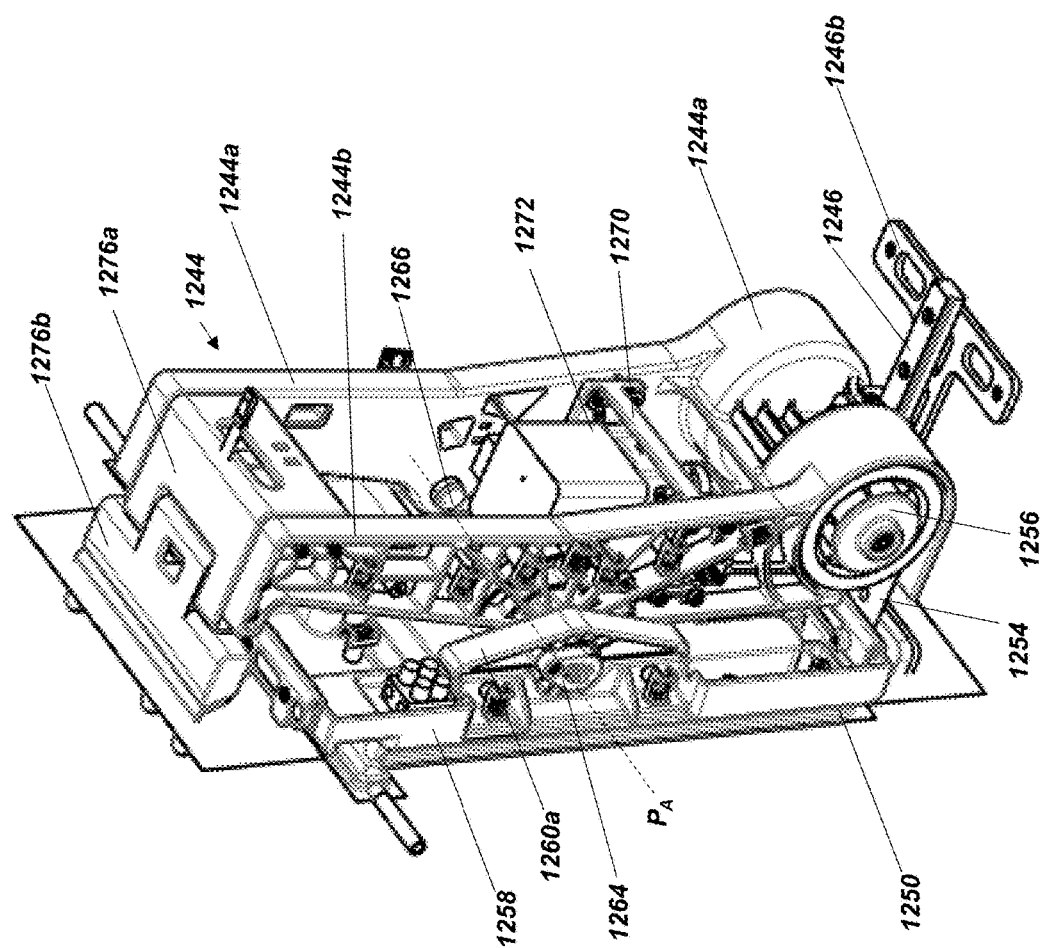
FIG. 13A is a isometric view of a third heating assembly and support member of the first dry thawing chamber of FIG. 11C.
Figure 13B:
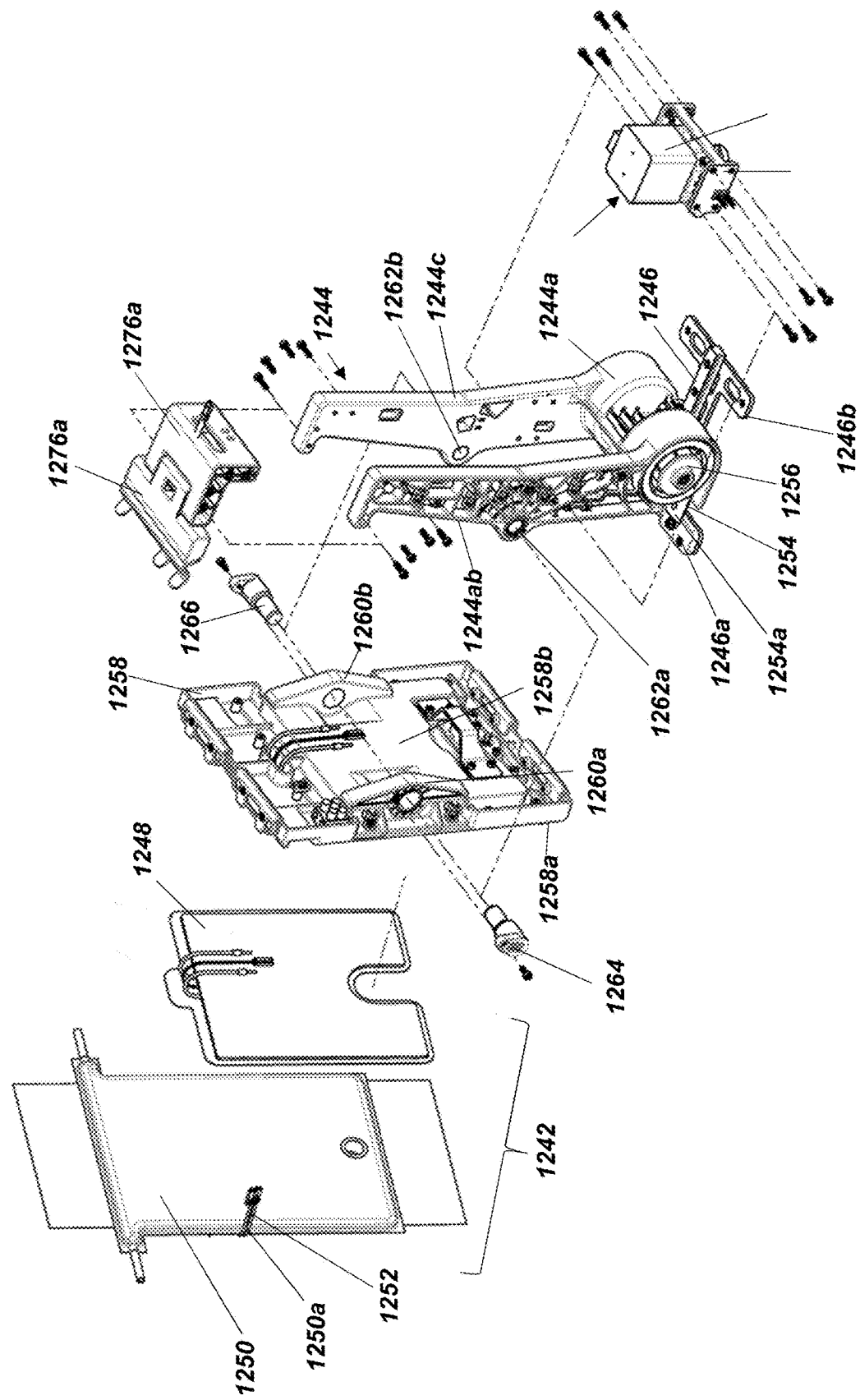
FIG. 13B is a partial exploded view of FIG. 13A.

As shown in FIG. 11C and in more detail in FIGS. 13A-13B, the third heating assembly 1242 includes a heater 1248 and a heating cushion 1250 coupled thereto. While the heater 1248 can have a variety of configurations, as shown, the heater 1248 is in the form of a heater plate. At least one temperature sensor 1252 is coupled to an outer surface 1250*a* of the heating cushion 1250, and therefore in thermal communication therewith. The illustrated at least one temperature sensor 1252 is configured to measure the temperature of the heating cushion 1250 during use. While the at least one temperature sensor 1252 can have a variety of configurations, in this illustrated embodiment, the at least one temperature sensor 1252 includes two temperature sensors, a thermistor, e.g., a NTC thermistor, and a thermocouple. In certain embodiments, one of the two temperature sensors can be in communication with the power supply 1226 that is configured to supply electrical power to the heater 1248. In such instances, when the measured temperature of the heating cushion 1250 exceeds a predetermined threshold temperature, the one of the two temperature sensors can transmit a failsafe signal to the power supply 1226 that is operative to cause the power supply 1226 upon receipt to terminate delivery of power to the heater 1248. In other embodiments, the at least one temperature sensor 1252 can include one temperature sensor or more than two temperature sensors.

While the support frame 1244 can have a variety of configurations, as shown, the support frame 1244 includes a base 1244*a* and two support arms 1244*b*, 1244*c* extending therefrom. As shown, the support frame 1244 is mounted to the first track 1246. While the support frame 1244 is biased in a first direction towards a first end 1246*a* of the first track 1246, the support frame 1244 is configured to slide along the first track 1246. That is, the support frame 1244 can slide in a second direction towards the between the first and second ends 1246*a*, 1246*b* of the first track 1246 so as to allow the first chamber frame 1222 to accommodate for different volumes of an enclosed biological substance that is to be thawed. Further, the sliding of the support frame 1244 can also allow for and maintain an effective thermal communication between the enclosed biological substance disposed between the first and third heating assemblies 1208, 1242.

While the support frame 1244 is biased in a first direction towards the first end of the first track 1246, This sliding of the support frame 1244 between the first and second ends 1246*a*, 1246*b* of the first track 1246 can be accomplished in a variety of ways. For example, in this illustrated embodiment, a first biasing element 1254 and a second biasing element, obscured in FIGS. 11C and 13A-13B, are coupled between the base 1244*a* of the support frame 1244 and the first end 1246*a* of the first track 1246. In this illustrated embodiment, the first biasing element 1254 and the second biasing element are structurally similar, and therefore for sake of simplicity, the following description is with respect to the first biasing element 1254. A person skilled in the art will understand, however, that the following discussion is also applicable to the second biasing element.

While the first biasing element 1254 can have a variety of configurations, as shown in FIGS. 13A and 13B, the first biasing element 1254 is a bi-stable spring band that is wound about a drum 1256 that is housed within and connected to the base 1244*a* of the support frame 1244. The bi-stable spring band 1254 has a first end 1254*a* that is coupled to the first end 1246*a* of the first track 1246 and a second end (obscured in FIGS. 11C and 13A-13B) that is coupled to the drum 1256. In this way, the support frame 1244 can linearly slide along the first track 1246 between its first and second ends 1246*a*, 1246*b*, and thus relative to the first chamber frame 1222.

Figure 16B:
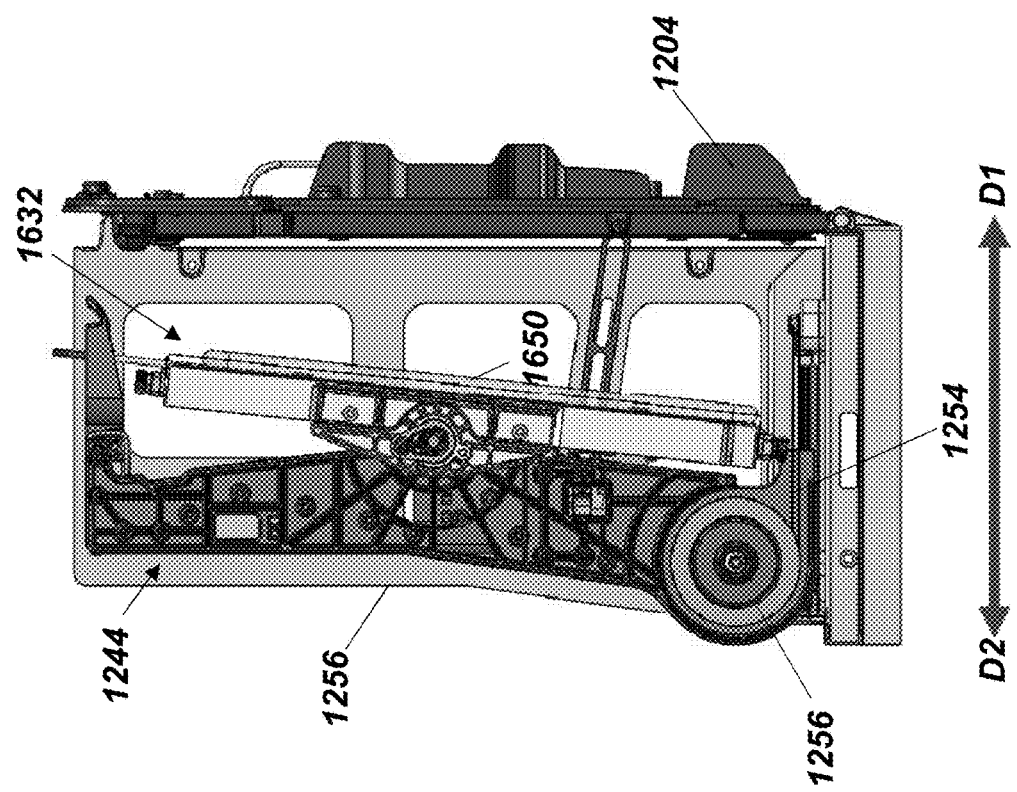
FIG. 16B is a side view of the portion of the dry thawing chamber of FIG. 16A, illustrating the support frame in a second position.
Figure 16A:
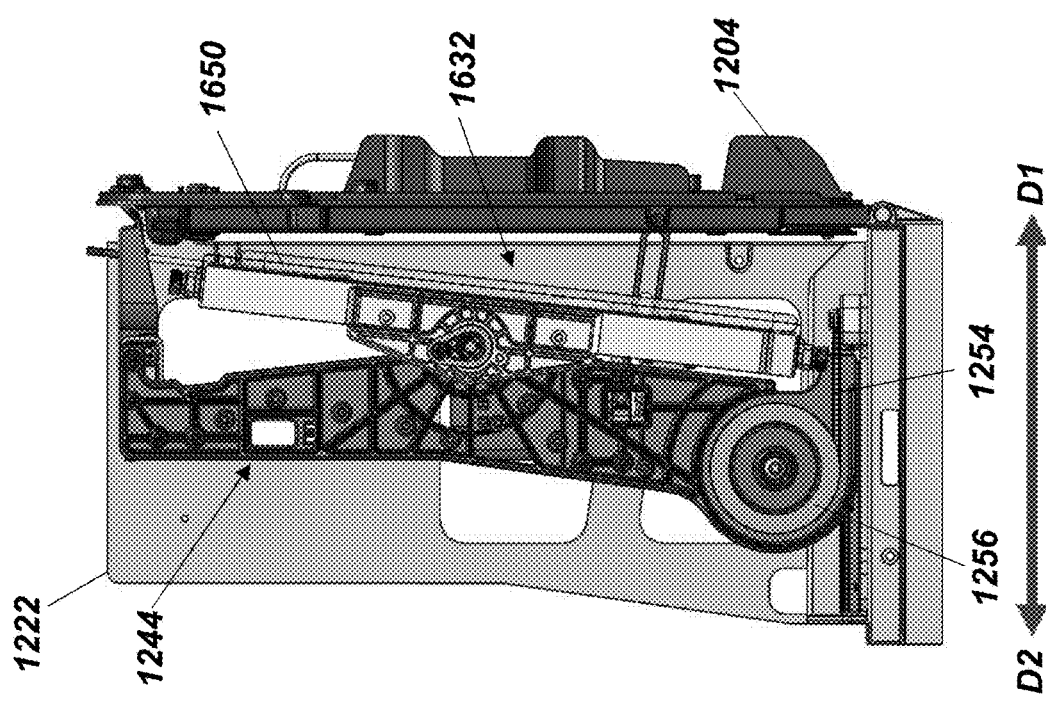
FIG. 16A is side view of a portion of another embodiment of a dry thawing chamber including a support frame, illustrating the support frame in a first position.

FIGS. 16A and 16B illustrate the linear translation of the support frame 1244 relative to the first chamber frame 1222 during use. While the heating cushion 1650 in FIGS. 16A and 16B is different than the heating cushion 1250 shown in FIGS. 11C and 13A-13B, a person skilled in the art will appreciate that the linear sliding movement of the support frame 1244 is the same. For purposes of simplicity only, certain components are not illustrated in FIGS. 16A and 16B.

In use, an enclosed biological substance (not shown) is inserted into the first chamber frame 1222 between the first heating assembly 1208 (not shown) and the third heating assembly 1632, which is similar to the third heating assembly 1242 except for the structural configuration of the heating cushion 1650. As the chamber door 1204 is moved from an open configuration to a closed configuration, the support frame 1244 can move in a second direction (D2) that is opposite the first direction (D1) in which the support frame 1244 is biased via the bi-stable spring band 1254. For example, the support frame 1244 can move in the second direction (D2) from a first position as shown in FIG. 16A to a second position in FIG. 16B or any other position therebetween. As such, the force being applied to the support frame 1244, e.g., by the enclosed biological substance, the first and third heating assemblies 1208, 1632, and the chamber door 1204, is sufficient to overcome the biasing force of the bi-stable spring band 1254. This causes the bi-stable spring band 1254 to partially unwind from the drum 1256, thereby allowing the support frame 1244 to move. As a result, the enclosed biological substance is compressed between the first and third heating assemblies 1208, 1632. This compression can help increase the surface contact area between the enclosed biological substance and the first and third heating assemblies 1208, 1632, thereby increasing the heating efficiency. In certain instances, depending on the volume of the enclosed biological substance, the insertion of the enclosed biological substance alone can cause the support frame 1244 to slide in the second direction (D2).

Further, during heating, as the enclosed biological substance thaws, the position of the support frame 1244 can be adjusted. That is, during heating, as the force being applied to the support frame 1244 changes, the support frame 1244 can retract towards its first position (FIG. 16A) via the partial rewinding of the bi-stable spring band 1254 about the drum 1256. Once the enclosed biological substance is removed from the first chamber frame 1222, the support frame 1244 can return to its first position as shown in FIG. 16A.

Referring back to FIGS. 13A and 13B, the third heating assembly 1242 is mounted to a first surface 1258*a* (e.g., front surface) of an agitator plate 1258. The agitator plate 1258 is pivotally coupled to the support frame 1244. While the agitator plate 1258 can be pivotally coupled to the support frame 1244 using a variety of mechanisms, in this illustrated embodiment, a first set of pivot mounts 1260*a*, 1260*b* of the agitator plate 1258 and a second set of pivot mounts 1262*a*, 1262*b* of the support frame 1244 are coupled together via pivot pins 1264, 1266. As a result, this pivoting engagement defines a pivot axis (PA) in which the agitator plate 1258, and thus the third heating assembly, can pivot relative to the first chamber frame to agitate an enclosed biological substance that is contact therewith.

The pivotal motion of the agitator plate 1258, and thus the third heating assembly 1242, can be effected by an agitation device. For example, as shown in FIGS. 13A and 13B, an agitation device 1268 is coupled to the support frame 1244 and configured to selectively contact the second surface 1258*b* of the agitator plate 1258 to cause pivotal movement thereof. In this illustrated embodiment, the agitation device 1268 is coupled to a chassis 1270 that is mounted between the two support arms 1244*b*, 1244*c* of the support frame 1244.

As shown in FIG. 14, the agitation device 1268 includes a motor 1272 and a cam 1274. The motor 1272 includes a rotary motor shaft 1272*a* that is coupled to the cam 1274 such that, upon actuation, the motor 1272 can cause the cam 1274 to rotate. While the cam 1274 can have a variety of configurations, in this illustrated embodiment, the cam 1274 is oblong shaped. As a result, during rotation, the cam 1274 pushes on the second surface 1258*b* of the agitator plate 1258 to causes the agitator plate 1258 to pivot about the pivot axis (PA). This pivotal motion alternates application of a compressive force against an enclosed biological substance and agitates the enclosed biological substance, e.g., during heating. As a result, substantially even heating throughout the enclosed biological substance can be effected.

Figure 17B:
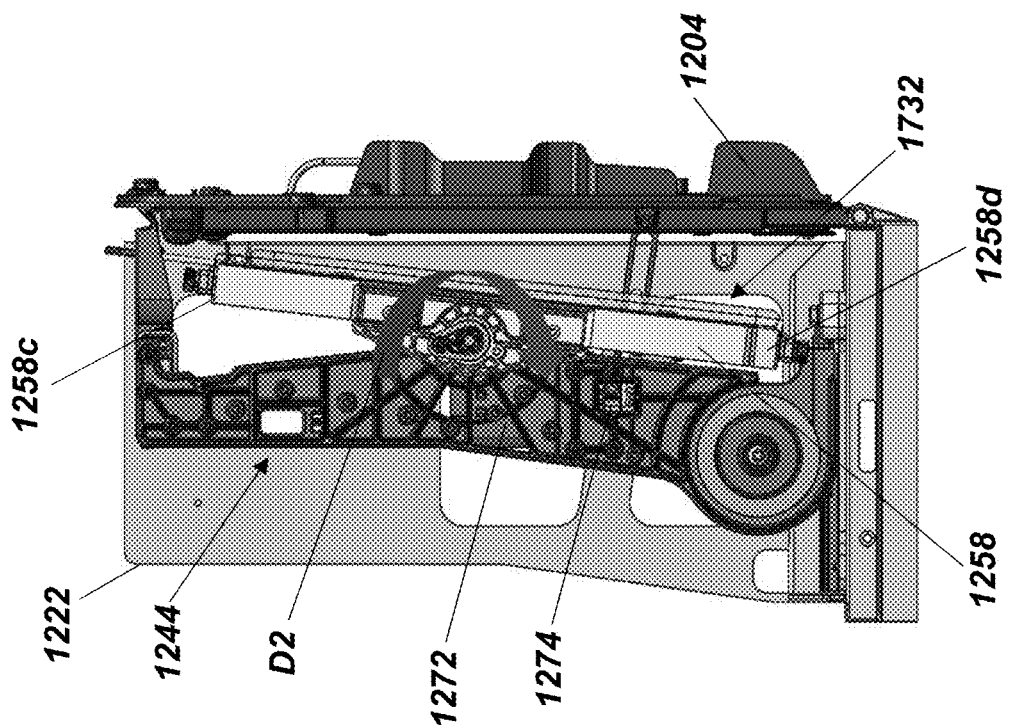
FIG. 17B is a side view of the portion of the dry thawing chamber of FIG. 17A, illustrating the agitator plate in a second position.
Figure 17A:
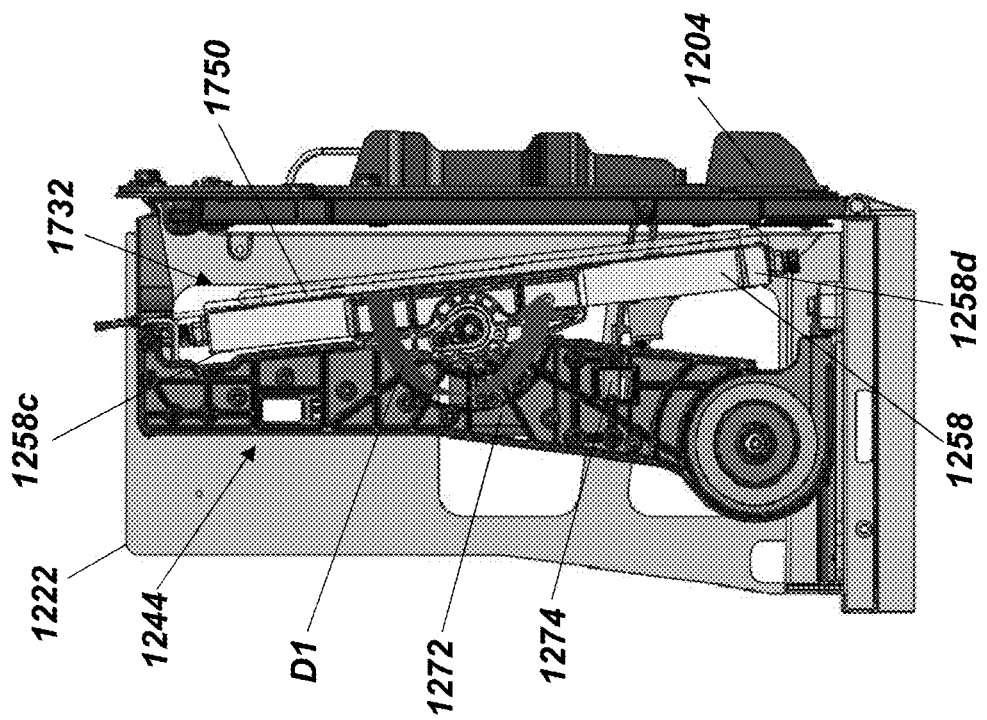
FIG. 17A is side view of a portion of another embodiment of a dry thawing chamber including an agitator plate, illustrating the agitator plate in a first position.

FIGS. 17A and 17B illustrate the pivotal motion of the agitator plate 1258 relative to the first chamber frame 1222 during use. While the heating cushion 1750 in FIGS. 17A and 17B is different than the heating cushion 1250 shown in FIGS. 11C and 13A-13B, a person skilled in the art will appreciate that the pivotal motion of the agitator plate 1258 is the same. For purposes of simplicity only, certain components are not illustrated in FIGS. 17A and 17B.

In use, an enclosed biological substance (not shown) is inserted into the first chamber frame 1222 between the first heating assembly 1208 (not shown) and the third heating assembly 1732, which is similar to the third heating assembly 1242 except for the structural configuration of the heating cushion 1750. Once the motor 1272 is activated, the cam 1274 can rotate and come into contact with the agitator plate 1258, thereby causing the agitator plate 1258 to pivot in a first direction, denoted by arrow D1, to a first pivotal position, as shown in FIG. 17A. This causes the top end 1258c of the agitator plate 1258 to move towards the support frame 1244 and the bottom end 1258d of the agitator plate 1258 to move away from the support frame 1244. Since the first heating assembly 1208 is fixed in place when the chamber door 1204 is closed, pivotal motion of the agitator plate 1258 in the first direction D1 urges the enclosed biological substance upwards towards the top portion 1232 (not shown) of the first chamber frame 1222. In some instances, this pivotal motion can also urge fluid (not shown) within the heating cushion 1750 of the third heating assembly 1732 towards a top end 1258c of the agitator plate 1258. As further shown in FIG. 17B, the agitator plate 1258 can pivot in a second direction, denoted by arrow D2, from the first pivotal position to a second pivotal position. Since the first heating assembly 1208 (not shown) is fixed and the cam 1274 rotates away from the agitator plate 1258, pivotal motion of the agitator plate 1258 in the second direction D2 is effected by downward movement of the enclosed biological substance, and in some instances, also the heating cushion fluid, under the force of gravity. As such, the pivotal motion of the agitator plate 1258 can agitate the enclosed biological substance positioned between the first and third heating assemblies 1208, 1732.

Figure 15:
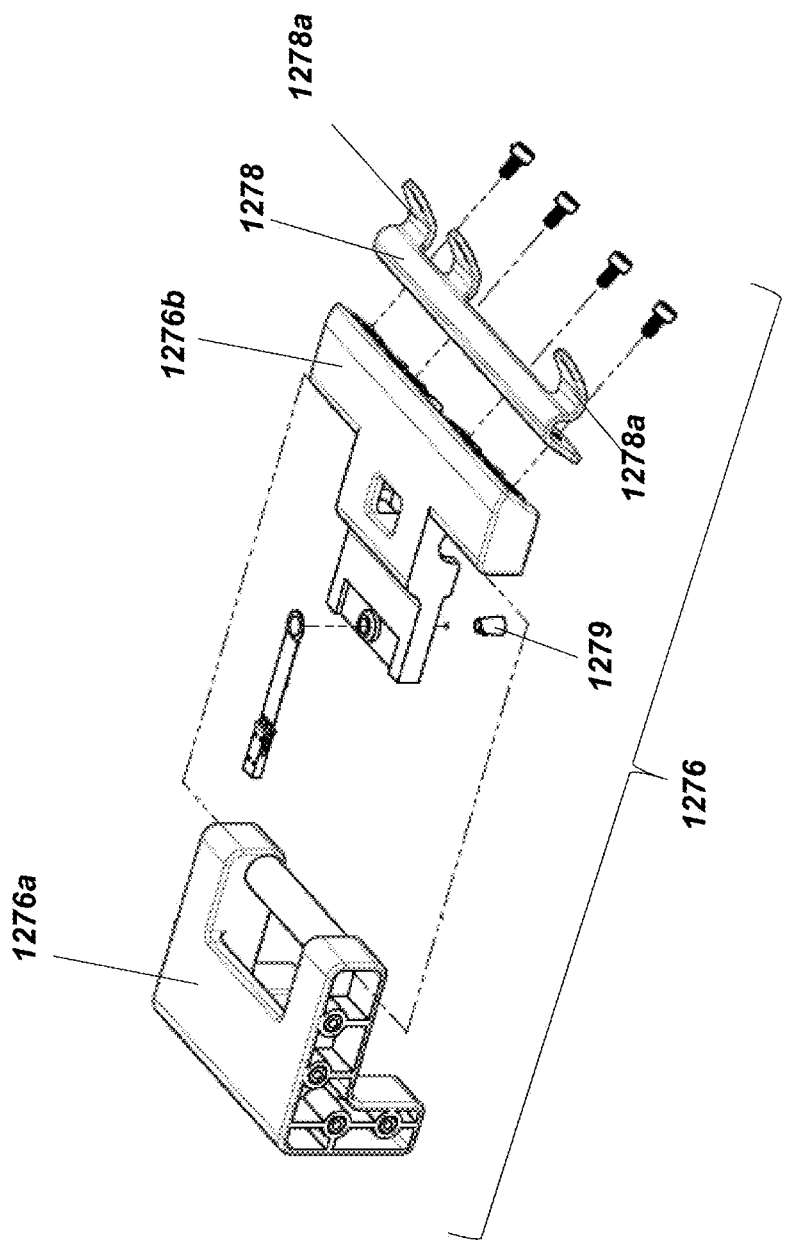
FIG. 15 is an exploded view of a mounting bracket of the first dry thawing chamber of FIG. 11C.

Referring back to FIGS. 13A-13B, a mounting bracket 1276, which is shown in more detail in FIG. 15, having a first portion 1276a and a second portion 1276b extending therefrom. The first portion 1276a of the mounting bracket 1276 is coupled to and extends between the two support arms 1244b. The second portion 1276b includes a hooking mount 1278 having at least one hook 1278a that is configured to engage and mount an enclosed biological substance, e.g., an enclosed biological substance disposed within a bag assembly, like bag assembly 600, within the first chamber frame 1222 and between the first and third heating assemblies 1208, 1242. Further, the second portion 1276b includes a weight sensor 1279 that is configured to measure a weight of an enclosed biological substance, e.g., an enclosed biological substance disposed within a bag assembly, like bag assembly 600, that is engaged to the mounting bracket 1276.

Temperature Sensors

Figure 19A:
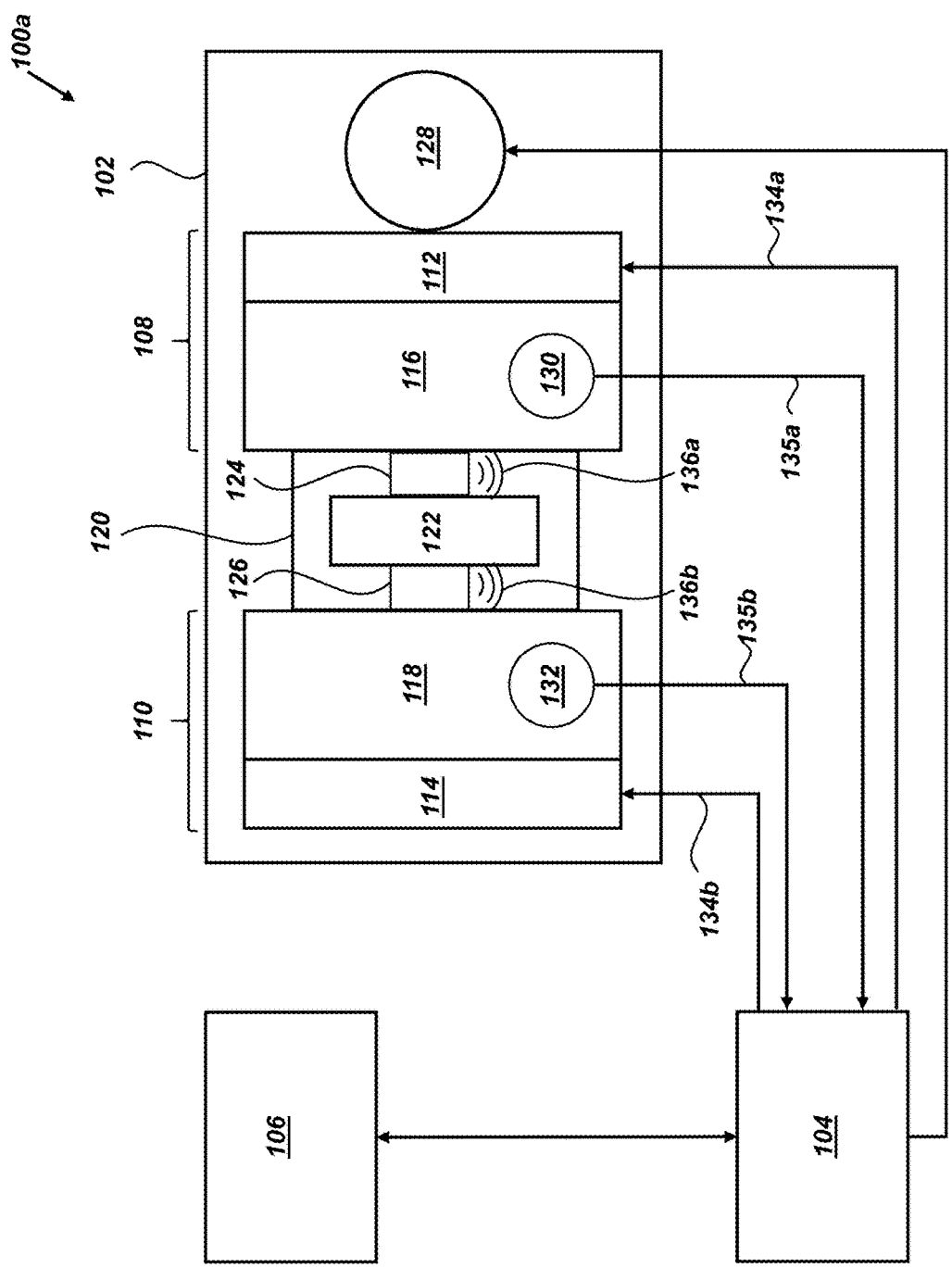
FIG. 19A is a schematic block diagram illustrating one exemplary embodiment of a dry thawing system including a dry thawing chamber configured to thaw a biological substance based upon temperature measurements acquired from one or more temperature sensors in a first configuration.
Figure 19B:
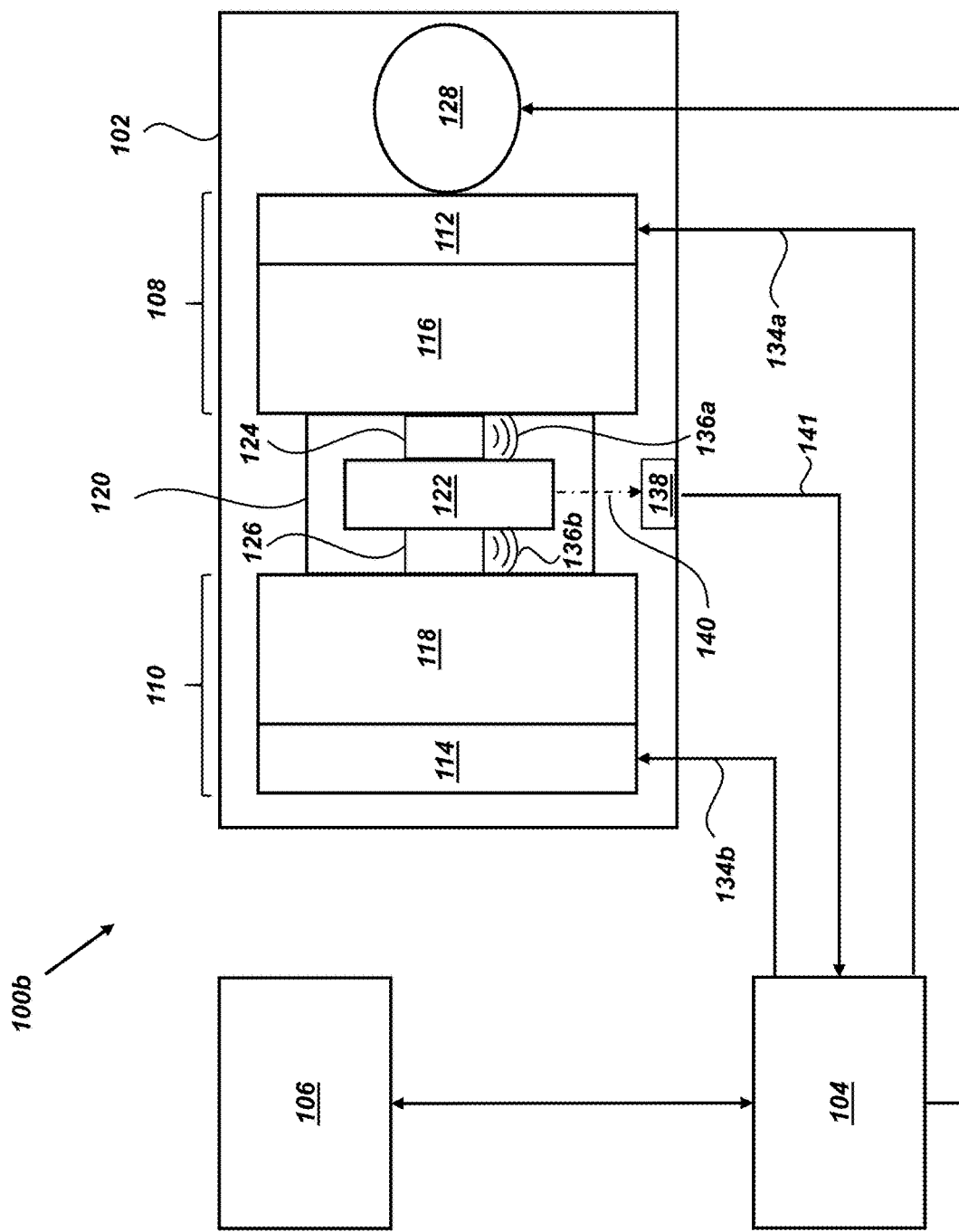
FIG. 19B is a schematic block diagram illustrating another exemplary embodiment of a dry thawing system including a dry thawing chamber configured to thaw a biological substance based upon temperature measurements acquired from one or more temperature sensors in a second configuration.
Figure 19C:
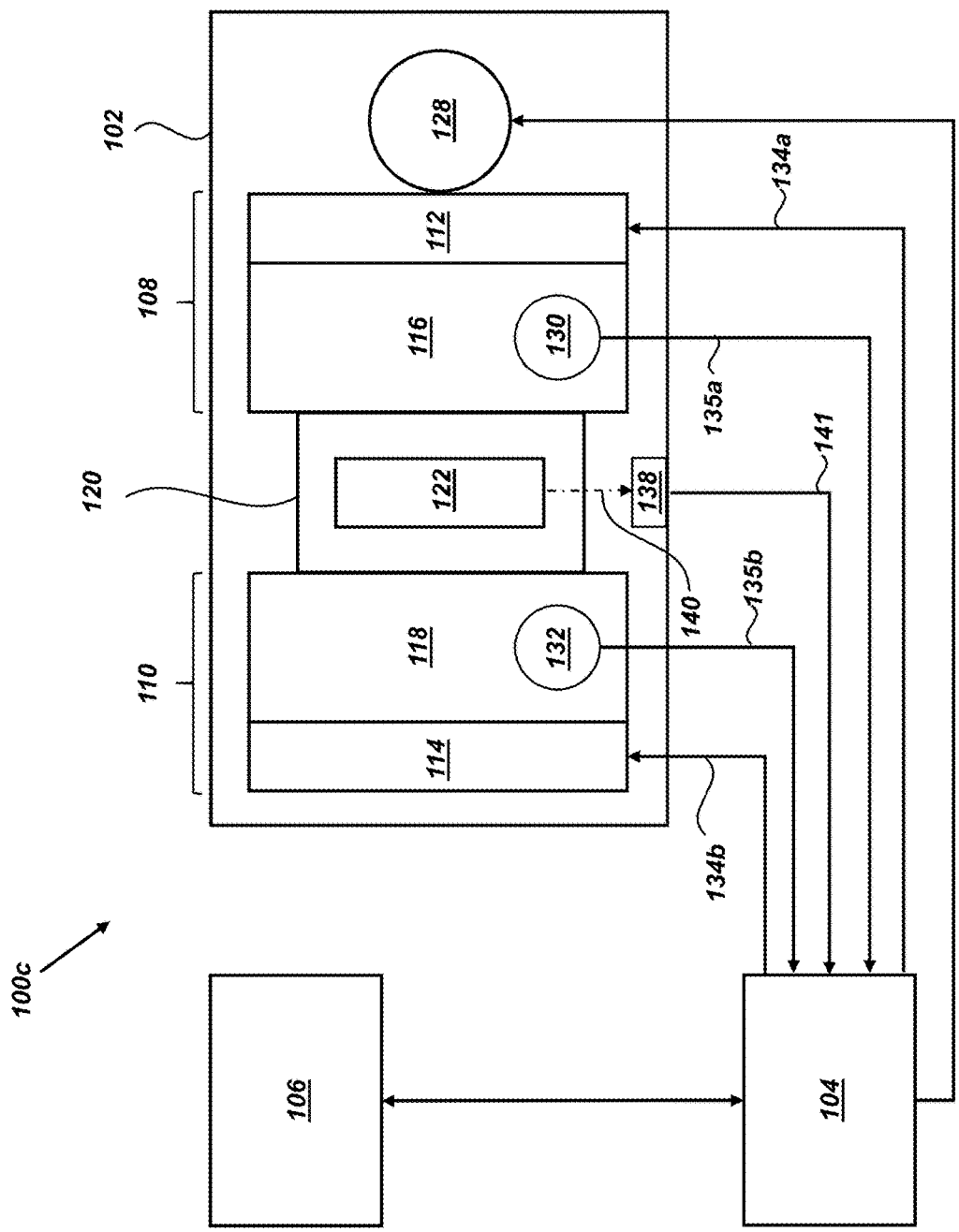
FIG. 19C is a schematic block diagram illustrating a further exemplary embodiment of a dry thawing system including a dry thawing chamber configured to thaw a biological substance based upon temperature measurements acquired from one or more temperature sensors in a third configuration.
Figure 19D:
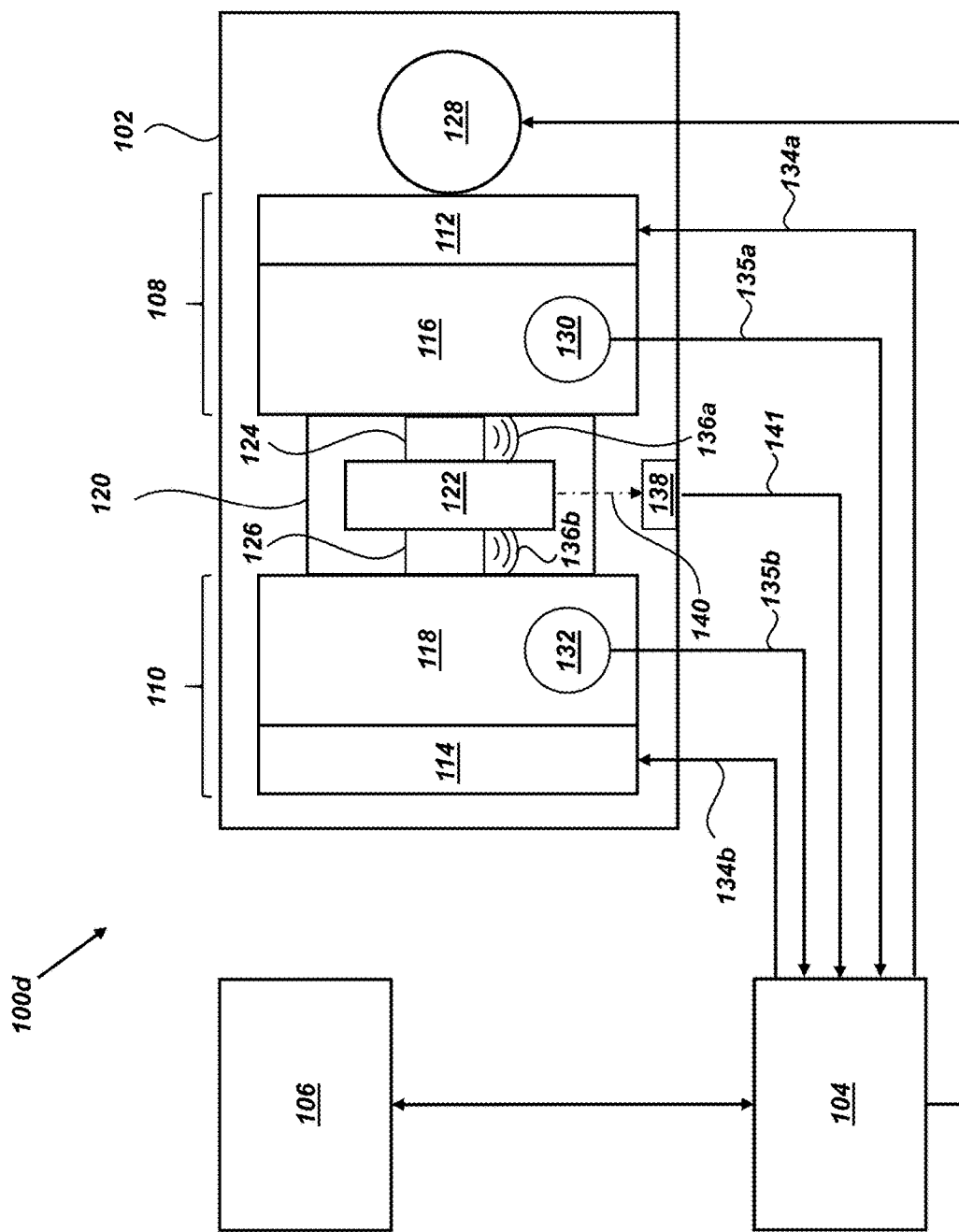
FIG. 19D is a schematic block diagram illustrating a further exemplary embodiment of a dry thawing system including a dry thawing chamber configured to thaw a biological substance based upon temperature measurements acquired from one or more temperature sensors in a fourth configuration.
Figure 19E:
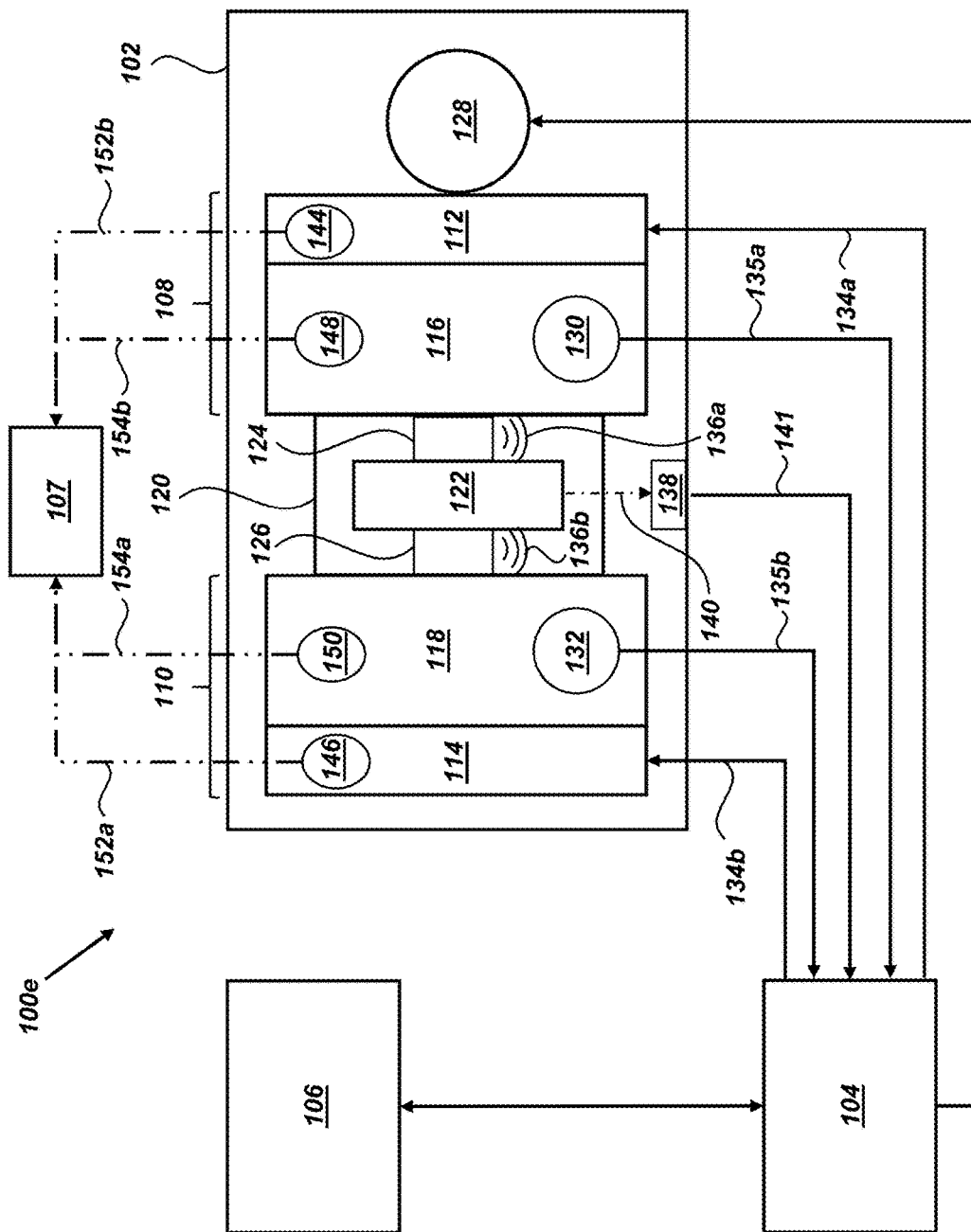
FIG. 19E is a schematic block diagram illustrating a further exemplary embodiment of a dry thawing system including a dry thawing chamber configured to thaw a biological substance based upon temperature measurements acquired from one or more temperature sensors in a fifth configuration.

The one or more temperature sensors can adopt a variety of configurations. In certain embodiments, as will be discussed in greater detail below, the temperature sensors can be contact temperature sensors, such as a first contact temperature sensor 124, a second contact temperature sensor 126, a third contact temperature sensor 130, and a fourth contact temperature sensor 132, as shown in FIG. 19A, and non-contact temperature sensors, such as a first non-contact sensor 138, as shown in FIGS. 19B-19D, and combinations thereof. In one aspect, contact temperature sensors 124, 126 can be integrated with, or secured to, the enclosed biological substance (e.g., via an inner or outer surface of an overwrap bag, discussed below) for measurement of the temperature of the enclosed biological substance. As an example, one or more contact temperature sensors 124, 126 can be positioned on an inner surface of the overwrap bag for contact with the enclosed biological substance. In another aspect, contact temperature sensors 130, 132 can be integrated with, or secured to, heating cushions (e.g., an inner or outer surface) for measurement of the temperature of heating cushions. In a further aspect, non-contact temperature sensors 138 can be distanced from a target (e.g., the enclosed biological substance, the overwrap bag, the heating cushion, etc.) and configured to measure temperature of at least one target. As an example, non-contact temperature sensors can measure electromagnetic radiation emitted from the enclosed biological substance (e.g., infrared radiation, dash-dot arrows).

In certain embodiments, the temperature sensors can communicate with the controller via communication links that are wired and/or wireless. As an example, one or more of the contact temperature sensors (e.g., contact temperature sensors 124, 126, 130, 132 shown in FIGS. 19A and 19D) can be in integrated with a radiofrequency identification (RFID) tag mounted to the overwrap bag and/or the heating cushion. Mounting can include being printed on a surface, adhered to a surface by an adhesive, and the like. In further embodiments, respective temperature sensors can be a sensor of a smart label, as discussed in International Patent Application No. WO 2016/023034, filed Aug. 10, 2015, entitled "Smart Bag Used In Sensing Physiological And/Or Physical Parameters Of Bags Containing Biological Substance," the entirety of which is hereby incorporated by reference. The RFID tag can be configured to wirelessly transmit temperature measurements to a receiver in communication with the controller. While not shown, embodiments of the non-contact sensors can also be configured to communicate wirelessly with the controller.

In further embodiments, the dry thawing chamber can include at least one contact temperature sensor (e.g., contact temperature sensors 124, 126, 130, 132 shown in FIGS. 19A and 19D) and at least one non-contact temperature sensor (e.g., non-contact temperature sensor 138 shown in FIGS. 19B and 19D). This configuration can improve the accuracy of temperature measurements and provide redundancy. In one example, faulty temperature sensors can be identified. For instance, temperature measurements of the enclosed biological substance acquired by the contact temperature sensors and non-contact temperature sensors can be compared to one another. If a deviation is observed between these measurements, the controller can annunciate an alarm (e.g., an audio and/or visual signal) for replacement of the faulty temperature sensor. The alarm can also include a signal transmitted to the controller that is operative to cause the controller to cease to employ the faulty temperature sensor for control of dry thawing processes. Redundancy can be further provided by having the controller employ a non-faulty temperature sensor in place of the faulty temperature sensor for control of dry thawing processes. In this manner, faulty temperature sensors can be identified and replaced, while avoiding use of inaccurate temperature measurements for control of dry thawing processes.

Dry Thawing Systems

FIGS. 19A-19D illustrate exemplary embodiments of a dry thawing system 100a, 100b, 100c, 100d for thawing biological substances. Each illustrated dry thawing system 100a, 100b, 100c, 100d includes a dry thawing chamber 102, a controller 104, and a user interface 106. The dry thawing chamber 102 can include one or more heating assemblies 108, 110, each having a heater 112, 114 that is in thermal communication with a heating cushion 116, 118. One or more heating cushions 116, 118 can be configured to be positioned in contact with an overwrap bag 120 surrounding an enclosed biological substance 122 to thereby heat the substance. The dry thawing chamber 102 can also include one or more temperature sensors for monitoring temperature of the enclosed biological substance 122, one or more temperature sensors for monitoring temperature of the one or more heating cushions 116, 118, and an agitation device 128 in mechanical communication with the overwrap bag 120 (e.g., via heating assembly 108). The controller 104 can be placed in communication with the one or more heating assemblies 108, 110 and the one or more temperature sensors by wired communication links and/or wireless communication links and it can be configured to employ one or more of the temperature measurements for control of a dry thawing process. In this illustrated embodiment, the one or more heating assemblies 108, 110 are in communication with the controller 104 via wired communication links 134a, 134b.

The one or more temperature sensors can adopt a variety of configurations. FIG. 19A illustrates a first configuration of the one or more temperature sensors including one or more first temperature contact sensors 124, 126 and one or more second contact temperature sensors 130, 132. In one aspect, one or more first contact temperature sensors 124, 126 can be integrated with, or secured to, the overwrap bag 120 (e.g., secured to an inner or outer surface of the overwrap bag 120) for measurement of the temperature of the enclosed biological substance 122. As shown, respective ones of the one or more first contact temperature sensors 124, 126 are positioned on opposed, inner surfaces of the overwrap bag 120 for contact with the enclosed biological substance 122. However, in alternative embodiments, the location and number of the one or more first contact temperature sensors 124, 126 can be varied. In one aspect, each of the one or more first contact temperature sensors 124, 126 can be positioned on outer surfaces of the overwrap bag 120. In another aspect, one of the one or more first contact temperature sensors 124, 126 can be positioned on an inner surface of the overwrap bag 120 and the other of the one or more first contact temperature sensors 124, 126 can be positioned on an outer surface of the overwrap bag 120. In a further aspect, the one or more first contact temperature sensors 124, 126 can be positioned on the same side of the overwrap bag 120. In an additional aspect, fewer (e.g., 1) or greater (e.g., three or more) first contact temperature sensors can be employed without limit.

As further shown in FIG. 19A, the one or more second contact temperature sensors 130, 132 can be integrated with, or secured to, heating cushions 116, 118 (e.g., an inner or outer surface) for measurement of the temperature of thereof. As shown, respective ones of the one or more second contact temperature sensors 130, 132 are positioned on outer surfaces of each heating cushion 116, 118. However, in alternative embodiments, the location and number of the one or more second contact temperature sensors 130, 132 can be varied. In one aspect, each of the one or more second temperature sensors 130, 132 can be positioned on inner surfaces of their corresponding heating cushions 116, 118 for contact with the overwrap bag 120, and thus the enclosed biological substance 122. In another aspect, one of the one or more second contact temperature sensors 130, 132 can be positioned on an inner surface of its corresponding heating cushion 116, 118 and the other of the one or more second contact temperature sensors 130, 132 can be positioned on an outer surface of its corresponding heating cushion 116, 118. In a further aspect, the one or more second contact temperature sensors 130, 132 can be positioned on the same heating cushion, e.g., either heating 116 or heating cushion 118. In a further aspect fewer (e.g., 1) or greater (e.g., three or more) second contact temperature sensors can be employed without limit. In another aspect, the one or more second contact temperature sensors can be distributed between the heating cushions in any combination.

In further aspects, the dry thawing system can include one or more non-contact temperature sensors. The non-contact temperature sensors can be distanced from a target (e.g., the enclosed biological substance, the overwrap bag, the heating cushion, etc.) and configured to measure temperature of at least one target. As an example, non-contact temperature sensors can measure electromagnetic radiation emitted from the enclosure (e.g., infrared radiation 140).

In certain embodiments, the one or more non-contact temperature sensors can be employed in combination with one or more contact temperature sensors, as shown in FIGS. 19B-19D. In some embodiments, as shown in FIG. 19B, the dry thawing system 100b includes a non-contact temperature sensor 138 employed in combination with the one or more first contact temperature sensors 126, 124. In other embodiments, as shown in FIG. 19C, the dry thawing system 100c includes a non-contact temperature sensor 138 employed in combination with the one or more second contact temperature sensors 130, 132. In yet other embodiments, as shown in FIG. 19D, the dry thawing system 100d includes a non-contact temperature sensor 138 employed in combination with the one or more first contact temperature sensors 124, 126 and the one or more second contact temperature sensors 130, 132. In further alternative embodiments, not shown, the contact temperature sensors (e.g., one or more first contact temperature sensors 124, 126, and/or one or more second contact temperature sensors 130, 132) can be omitted and one or more non-contact temperature sensors can be employed for measuring the temperature of the enclosed biological substance, the overwrap bag, and/or the heating cushion.

In certain embodiments, the contact temperature sensors (e.g., one or more first contact temperature sensors 124, 126 as shown in FIGS. 19A, 19B, and 19D, and one or more second contact temperature sensors 130, 132 as shown in FIGS. 19A, 19C, and 19D) and the non-contact temperature sensors (e.g., non-contact temperature sensor 138 shown in FIGS. 19B-19D) can communicate with the controller 104 via communication links that are wired and/or wireless. For example, as illustrated in FIGS. 19A, 19B, and 19D, the one or more first contact temperature sensors 124, 126 are in communication with the controller 104 via wireless communication links 136a, 136b; as illustrated in FIGS. 19A, 19C, and 19D, the one or more second contact temperature sensors 130, 132 are in communication with the controller 104 via wired communication links 135a, 135b; and as illustrated in FIGS. 19B-19D, the non-contact temperature sensor 138 is in communication with the controller 104 via wired communication links 141.

In some embodiments, one or more of the contact temperature sensors can be in integrated with a radiofrequency identification (RFID) tag mounted to the overwrap bag and/or the heating cushion. Mounting can include being printed on a surface, adhered to a surface by an adhesive, and the like. In further embodiments, respective temperature sensors can be a sensor of a smart label, as discussed in International Patent Application No. WO 2016/023034, filed Aug. 10, 2015, entitled "Smart Bag Used In Sensing Physiological And/Or Physical Parameters Of Bags Containing Biological Substance," the entirety of which is hereby incorporated by reference. The RFID tag can be configured to wirelessly transmit temperature measurements to a receiver in communication with the controller. While not shown, embodiments of the non-contact temperature sensors can also be configured to communicate wirelessly with the controller.

Beneficially, use of two or more temperature sensors selected from contact temperature sensors or non-contact temperature sensors improves the accuracy of temperature measurements and provides redundancy. In one example, faulty temperature sensors can be identified. For instance, temperature measurements of the enclosed biological substance 122 acquired by two different temperature sensors (e.g., a pair of temperature sensors selected from $T_1$, $T_2$, and T') can be compared to one another. If a deviation is observed between these measurements, the controller 104 can annunciate an alarm (e.g., an audio and/or visual signal) for replacement of the faulty temperature sensor. The alarm can also include a signal transmitted to the controller 104 that is operative to cause the controller 104 to cease to employ the faulty temperature sensor for control of dry thawing processes. Redundancy can be further provided by having the controller 104 employ a non-faulty temperature sensor in place of the faulty temperature sensor for control of dry thawing processes. In this manner, faulty temperature sensors can be identified and replaced, while avoiding use of inaccurate temperature measurements for control of dry thawing processes.

Embodiments of the dry thawing system can also be configured to provide a failsafe functionality in which one or both of the heaters 112, 114 stop generation of heat when the temperature measured by selected ones of the one or more of the heaters 112, 114 and the heating cushions 116, 118 exceeds predetermined threshold temperatures. As shown in the embodiment of FIG. 1E, a dry thawing system 100e can include one or more first failsafe temperature sensors 144, 146 that are configured to measure the temperature of the one or more heaters 112, 114 during use and one or more second failsafe temperature sensors 148, 150 that are configured to measure the temperature of the one or more heating cushions 116, 118 during use. The one or more first failsafe temperature sensors 144, 146 and the one or more second failsafe temperature sensors 148, 150 can be similar to the one or more first contact temperature sensors 126, 124 and the one or more second contact temperature sensors 130, 132 except that the one or more first failsafe temperature sensors 144, 146 and the one or more second failsafe temperature sensors 148, 150 are directly coupled to a power supply 107 that supplies electrical power to the one or more heaters 112, 114. That is, in certain embodiments, the one or more first failsafe temperature sensors 144, 146 and the one or more second failsafe temperature sensors 148, 150 are not in communication with the controller 104.

As such, the one or more first failsafe temperature sensors 144, 146 and the one or more second failsafe temperature sensors 148, 150 can communicate with the power supply 107 via communication links 152a, 152b, 154a, 154b that are wired and/or wireless. In this illustrated embodiment, the one or more first failsafe temperature sensors 144, 146 and the one or more second failsafe temperature sensors 148, 150 are in communication with the power supply 107 via wired communication links 152a, 152b, 154a, 154b.

During use, the one or more first failsafe temperature sensors 144, 146 and the one or more second failsafe temperature sensors 148, 150 can be configured to produce measurement signals (e.g., voltage, current, etc.) representative of their respective temperature measurements. The measurement signals can be compared to a threshold value representing the corresponding predetermined threshold temperature. If the measured temperature represented by the measurement signal is greater than the predetermined threshold temperature represented by the threshold value, a failsafe signal can be transmitted to the power supply 107.

The failsafe signal is operative to cause the power supply 107 to terminate delivery of electrical power independently to heaters 112, 114. As an example, if a first failsafe signal is transmitted to the power supply 107 in response to a temperature measurement made by either one of the first failsafe temperature sensor 144 or the second failsafe temperature sensor 148, delivery of electrical power can be terminated to heater 112. Alternatively, if a second failsafe signal is transmitted to the power supply 107 in response to a temperature measurement made by either one of the first failsafe temperature sensor 146 or the second failsafe temperature sensor 150, delivery of electrical power can be terminated to heater 114.

In certain embodiments, comparison of the measurement signal to the predetermined threshold value can be performed by a logic circuit (not shown). The measurement signal represents the input to the logic circuit and the failsafe signal represents the corresponding output of the logic circuit. In an embodiment, the logic circuit can integrated with each of the one or more first failsafe temperature sensors 144, 146 and the one or more second failsafe temperature sensors 148, 150.

In an exemplary embodiment, the predetermined threshold temperature value can be different for the heaters 112, 114 and the heating cushions 116, 118. In one aspect, the predetermined threshold temperature for the heaters 112, 114 can be about 105° C. In another aspect, the predetermined threshold temperature for the heating cushions 116, 118 can be about 40° C. for embodiments of the one or more second failsafe temperature sensors 148, 150 in the form of a thermocouple and about 40° C. to about 60° C. for embodiments of the one or more second failsafe temperature sensors 148, 150 in the form of a thermistor (e.g., negative temperature coefficient (NTC) thermistors and positive temperature coefficient (PTC) thermistors).

Thus, the one or more first failsafe temperature sensors 144, 146 and the one or more second failsafe temperature sensors 148, 150 can prevent damage to the enclosed biological substance 122, overwrap bag 120, and/or other components of the dry thawing system 100e. A person skilled in the art will appreciate that, while not shown, any of the dry thawing systems 100a, 100b, 100c, 100d described above can also include one or more first failsafe temperature sensors 144, 146 and the one or more second failsafe temperature sensors 148, 150.

In use, the overwrap bag 120 containing the enclosed biological substance 122 is positioned in contact with the one or more heating assemblies 108, 110 inside the dry thawing chamber 102. The one or more heating cushions 116, 118 can be deformable to accommodate the shape and volume of the overwrap bag 120 and the enclosed biological substance 122. In this manner, contact between the overwrap bag 120 and the one or more heating cushions 116, 118 can be ensured, promoting heat transfer from the one or more heating cushion 116, 118 to the overwrap bag 120 and the enclosed biological substance 122 contained therein.

The controller 104 can transmit first command signals to the first heating assembly 108 and the second heating assembly 110 to cause the first heater 112 and the second heater 114, respectively, to generate heat, at least a portion of which is conducted through the first heating cushion 116 and the second heating cushion 118, respectively, to the overwrap bag 120, and consequently to the enclosed biological substance 122. The temperature of a target can be measured by one or more contact temperature sensors (e.g., first contact temperature sensors 124, 126 and/or second contact temperature sensors 130, 132) and/or one or more non-contact temperature sensors (e.g., non-contact temperature sensor 138) and transmitted to the controller 104 via additional communication links. The target can be at least one of the heating cushions 116, 118, the overwrap bag 120, and the enclosed biological substance 122.

It can be appreciated that, in certain embodiments, the temperature of the overwrap bag 120 can be approximately equal to the temperature of the enclosed biological substance 122. Accordingly, the temperature of the enclosed biological substance 122 can be referred to herein interchangeably with the temperature of the overwrap bag 120.

The controller 104 can employ the measured temperatures as feedback for closed-loop control of the heater 112, 114 of each of the one or more heating assemblies 108, 110 and achievement of the predetermined temperature-time response. In certain embodiments, the controller 104 can employ the temperature of the heating cushions 116, 118 of each of the one or more heating assemblies 108, 110 for closed-loop feedback control of the respective heaters 112, 114. In alternative embodiments, the controller 104 can employ the temperature of the enclosed biological substance 122 for closed-loop feedback control of the heaters 112, 114. Thus, regardless of the geometry or volume of the enclosed biological substance 122, heat applied for thawing the enclosed biological substance 122 can be controlled to avoid over-heating or underheating the enclosed biological substance 122.

Substantially uniform heating can be achieved by use of the agitation device 128. The controller 104 can also transmit second command signals to the agitation device 128 to agitate the enclosed biological substance 122. As discussed in greater detail below, the agitation device 128 can include a motor configured to drive a rotating cam. The cam can be positioned for contact with one of the heating assemblies, which is pivotably mounted within a frame. Reciprocating motion of the cam can cause one of the heating assemblies (e.g., first heating assembly 108 shown in FIGS. 19A-19D) to reversibly pivot and apply compressive forces against the overwrap bag 120 and enclosed biological substance 122. In this manner, the enclosed biological substance 122 can be urged to move during the thawing process, facilitating substantially even heating throughout the enclosed biological substance 122.

Substantially uniform heating can include its ordinary and customary meaning understood by one of skill in the art. Substantially uniform heating can further include achieving a difference between a maximum and minimum temperature of the enclosed biological substance that is less than or equal to a predetermined temperature difference. Examples of the predetermined temperature difference can be from the range of about 0.5° C. to about 2° C.

Heating Algorithm

Embodiments of the dry thawing system 100a, 100b, 100c, 100d, 800, 900 can be configured to heat the enclosed biological substance 602 in four different stages: a pre-heating stage, an ice stage, a liquid stage, and a standby stage. Embodiments of flow diagrams illustrating each of the stages are illustrated in FIGS. 20-23. Embodiments of interfaces generated by the user interface 822 during one or more of these stages are further presented in FIGS. 24-29. Exemplary temperature set points and temperatures measured by the one or more temperature sensors 124, 126, 130, 132, 138 during the different stages are further discussed in the context of FIG. 30.

Figure 20:
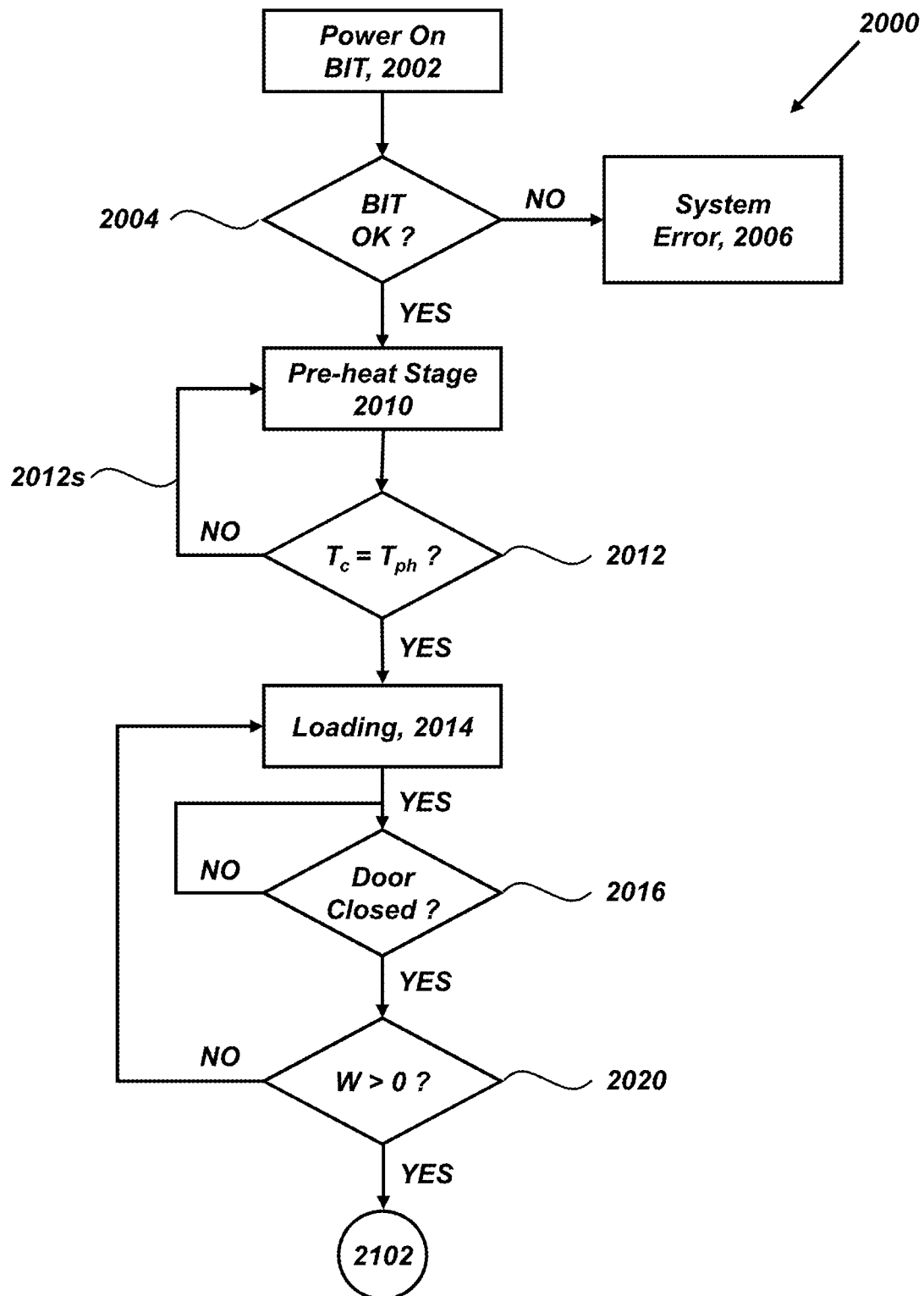
FIG. 20 is a flow diagram illustrating one exemplary embodiment of a method for pre-heating one or more selected dry thawing chambers.

FIG. 20 is a flow diagram illustrating one exemplary embodiment of a method 2000, including operations 2002-2020, for pre-heating one or more dry thawing chambers 200, 804, 806, 904, 906. Pre-heating can be performed prior to commencement of the ice stage. Pre-heating can allow the selected dry thawing chamber(s) to be maintained at a predetermined idle temperature when not in use, as long as the dry thawing 100a, 100b, 100c, 100d, 800, 900 is powered on. Beneficially, the pre-heating stage can reduce a total time required for thawing of the enclosed biological substance 602.

Under circumstances where the dry heating system 100a, 100b, 100c, 100d, 800, 900 is unpowered prior to the pre-heating stage, a power-up process can be performed prior to commencement of the pre-heating stage. Alternatively, under circumstances where the dry heating system 100a, 100b, 100c, 100d, 800, 900 is powered prior to the pre-heating stage, the power-up process can be omitted. In further embodiments, the pre-heating stage can be omitted and the ice stage can begin following the power-up process.

Figure 24:
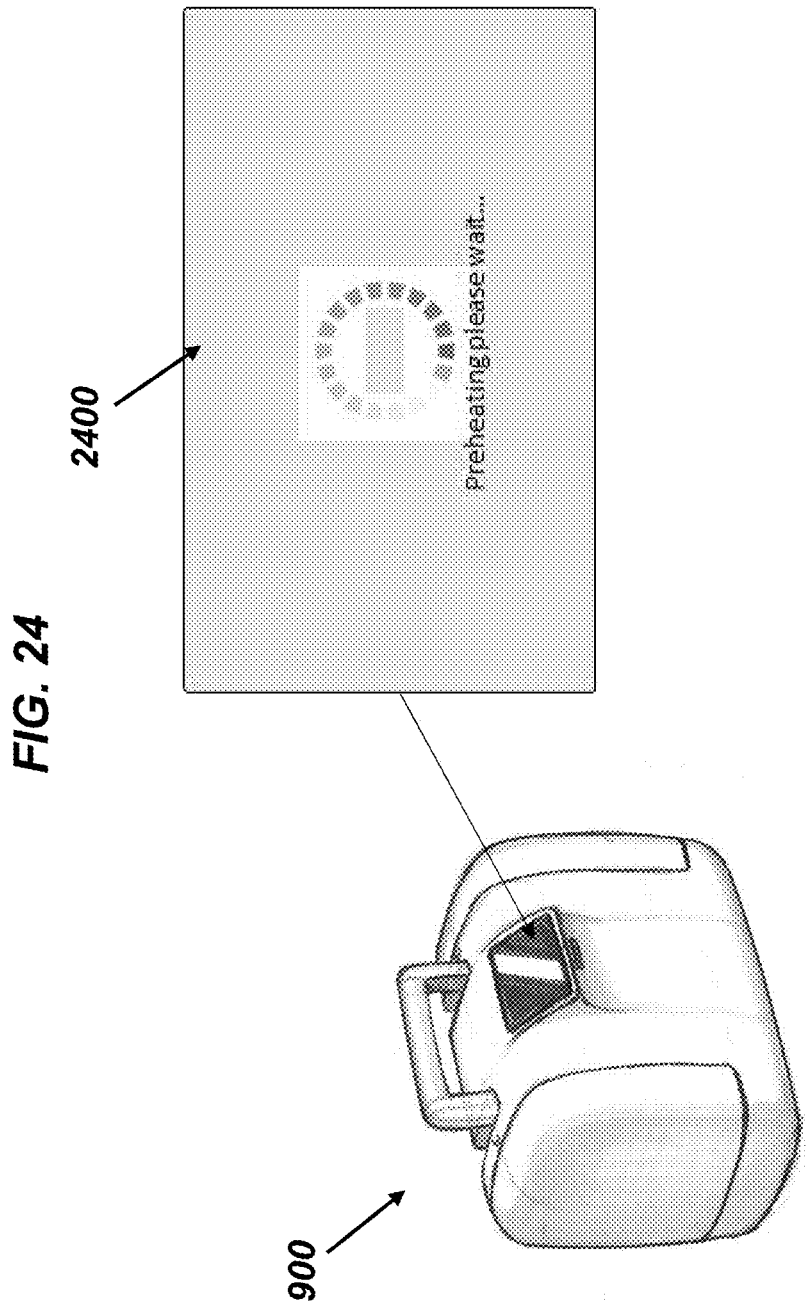
FIG. 24 is a diagram illustrating an exemplary embodiment of an interface for use by embodiments of the disclosed dry thawing systems during the pre-heating stage.

As shown in FIG. 24, a user can employ an interface 2400 displayed by the user interface 822 to initiate power up and pre-heating of one or more selected dry thawing chambers 200, 804, 800, 904, 906. In operation 2002 of FIG. 20, turning on power to the dry thawing system 100a, 100b, 100c, 100d, 800, 900 can activate a built in self-test (BIT) of one or more components of the dry thawing system 100a, 100b, 100c, 100d, 800, 900. As an example, the BIT can include power on self-test (POST) of computing components, such as the controller 104, as well as communication links 134a, 134b, 135a, 135b, 136a, 136b, 141, 146a, 146b and respective self-test routines of one or more of the heating assemblies 108, 110, 400, 500, 1208, 1242, 1732, agitation devices 224, 1268, temperature sensors 124, 126, 130, 132, 138, weight sensor 1279. In operation 2004, the controller 104 determines if any component (including itself) returns a signal indicating failure of its self-test (BIT OK?). If any component returns a signal indicating failure of its self-test, BIT OK is NO, the method 2000 moves to operation 2006 and an error message is displayed by the user interface 822. If no component returns a signal indicating failure of its self-test, BIT OK is YES, the method 2000 moves to operation 2010 to commence the pre-heat stage.

Figure 25:
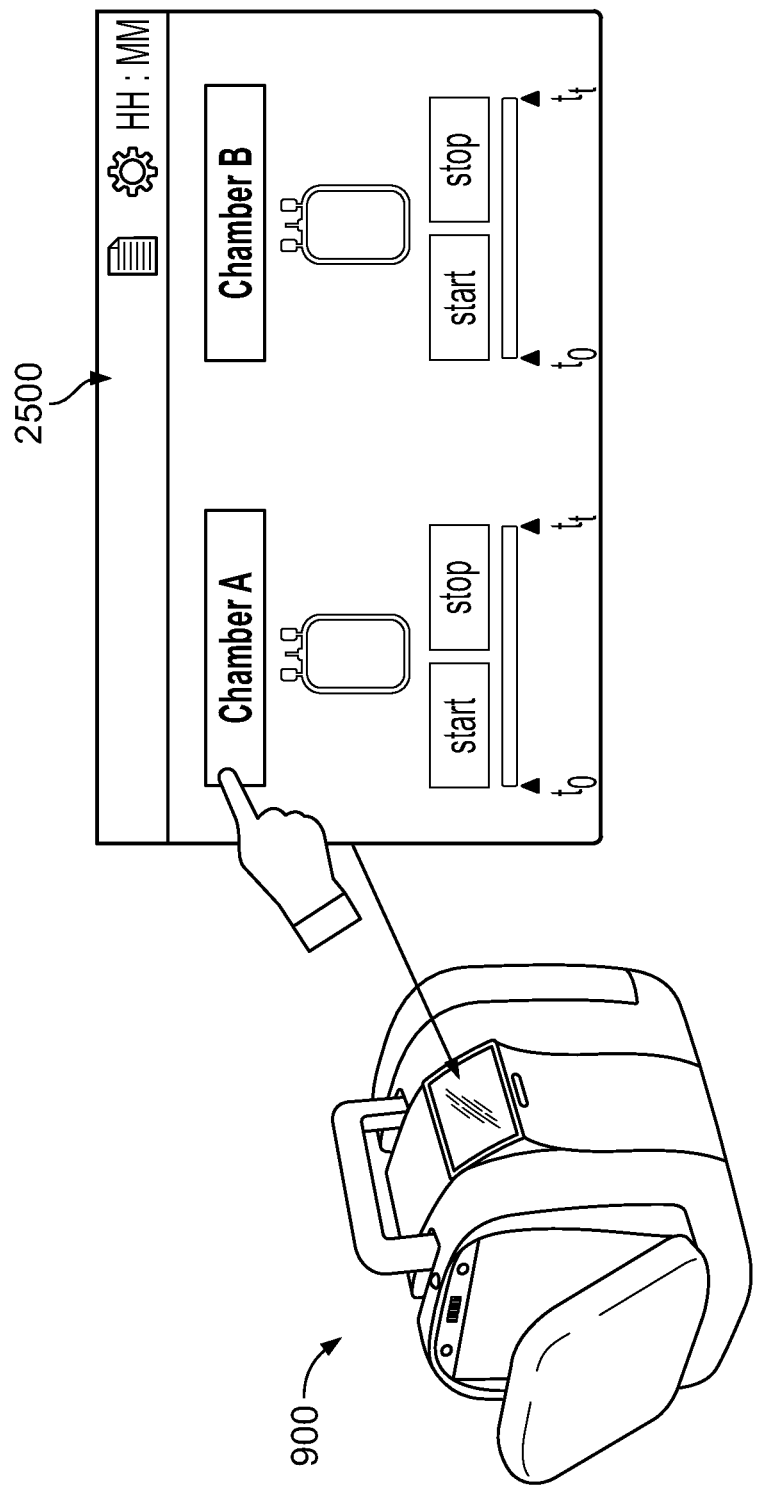
FIG. 25 is a diagram illustrating an exemplary embodiment of an interface for use by embodiments of the disclosed dry thawing systems to select the one or more dry thawing chambers.

In operation 2010, an available dry thawing chamber 200, 804, 800, 904, 906 is selected. As an example, FIG. 25 illustrates an interface 2500 displayed by the user interface 822 allowing an operator to select one or more of the dry thawing chambers 200, 804, 800, 904, 906 (e.g., chamber A and/or chamber B) for pre-heating. After input of the selected dry thawing chamber 200, 804, 800, 904, 906 is received, the method 2000 moves to operation 2012.

In operation 2012, the controller 104 generates one or more command signals 2012s operative to control power delivered to the one or more heating assemblies 108, 110, 400, 500, 1208, 1242, 1732 in thermal communication with the selected dry thawing chamber 200, 804, 800, 904, 906 (e.g., the chamber frame 202, 1222, 1224) to effect the temperature of respective heating cushions 116, 118, 1250, 1650, 1750 of the one or more heating assemblies 108, 110,

400, 500, 1208, 1242, 1732. As an example, the controller 104 is configured to perform closed-loop control of the heating cushion temperature. In one aspect, the controller 104 receives control parameters including a measured cushion temperature $T_c$ for at least one of the heating cushions 116, 118, 1250, 1650, 1750 (e.g., from the one or more temperature sensors 124, 126, 130, 132, 138), a pre-heating temperature set point temperature $T_{ph}$, and pre-heating settings $PID_{ph}$ (proportional-integral-derivative).

In order to generate the command signals 2012s, the controller 104 determines if there is a difference between each received measured cushion temperature $T_c$ and the pre-heating set point temperature $T_{ph}$ ($T_c=T_{ph}$?). If the controller 104 determines that there is a difference between the measured cushion temperature $T_c$ and the pre-heating set point temperature $T_{ph}$ ($T_c=T_{ph}$ is NO), a correction is calculated based upon this difference and $PID_{ph}$. The correction is transmitted from the controller 104 to respective ones of the heating assemblies 108, 110, 400, 500, 1208, 1242, 1732 as the command signal(s) 2012s and the method 2100 returns to operation 2010. In operation 2010, the one or more heating assemblies 108, 110, 400, 500, 1208, 1242, 1732 generate heat in response to receipt of the command signal(s) 2012s. Subsequently, the method 2000 moves to operation 2012 to again determine if there is a difference between each measured cushion temperature $T_c$ and the pre-heating set point temperature $T_{ph}$. The operations 2010 and 2012 are repeated in sequence until the measured cushion temperature $T_c$ is about equal to the pre-heating set point temperature $T_{ph}$ ($T_c=T_{ph}$ is YES). Subsequently, the method 2100 can move to operation 2014.

The pre-heating parameters $T_{ph}$ and the $PID_{ph}$ can be independently received by the controller 104 in in a variety of ways. In one aspect, these pre-heating parameters can be input by the operator via the user interface 822. In another aspect, these pre-heating parameters can be retrieved from a memory. In a further aspect, these pre-heating parameters can be hard-coded. In an embodiment, pre-heating set point temperature $T_{ph}$ can range from about 35° C. to about 40° C. $PID_{ph}$. In further alternative embodiments, at least one of the pre-heating set point temperature $T_{ph}$ and $PID_{ph}$ can be manually adjusted in real-time by the operator during the pre-heating stage.

Figure 30:
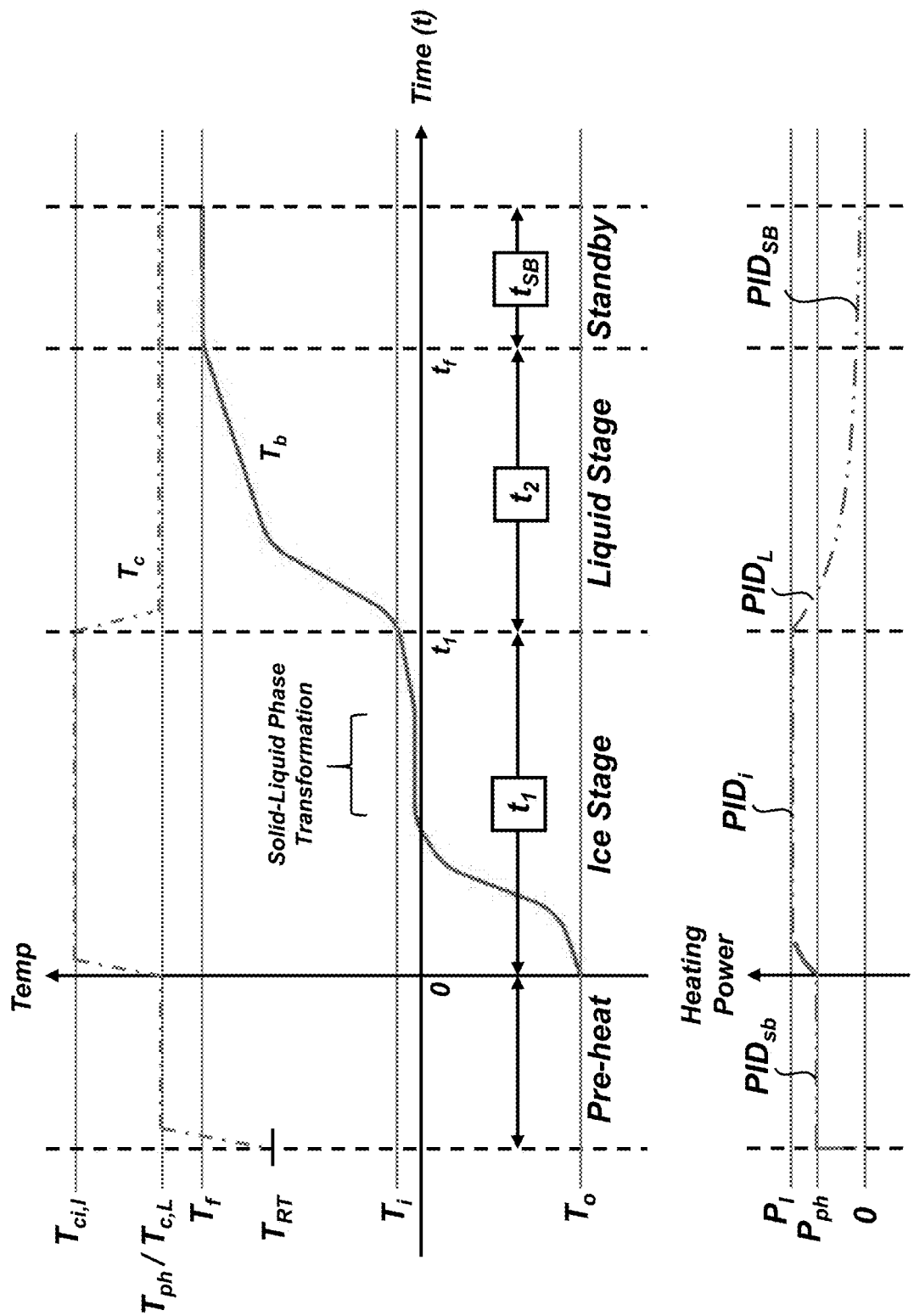
FIG. 30 is a plot illustrating exemplary embodiments of measured temperatures and heating cushion power as a function of time during a pre-heating stage, an ice stage, a liquid stage, and a standby stage.

FIG. 30 illustrates one exemplary embodiment of the measured cushion temperature $T_c$ (dot-dash-dot line) and power P delivered to the one or more heating cushions 116, 118, 1250, 1650, 1750 (dot-dot-dash line) with time during the pre-heating stage. Discussed above, the pre-heating stage commences in operation 2010. Assuming that the pre-heating stage follows the self-test operation preformed in method 2000, the measured heating cushion temperature is about equal to room temperature $T_{RT}$. That is, no heat is output by the one or more heating assemblies 108, 110, 400, 500, 1208, 1242, 1732 and the heating power P is zero. As shown, room temperature $T_{RT}$ is less than the pre-heating set point temperature $T_{ph}$. Thus, $T_c=T_{ph}$ is NO and the controller 104 transmits command signal(s) 2012s operative to cause the heating power P to increase and the one or more heating assemblies 108, 110, 400, 500, 1208, 1242, 1732 generate heat. As shown, the heating power P can rise from zero to a constant value. In response to the heat generation, the measured cushion temperature $T_c$ rises. Once the measured cushion temperature $T_c$ reaches the pre-heating set point temperature $T_{ph}$, $T_c=T_{ph}$ is YES, and the controller 104 further generates command signal(s) operative to maintain the cushion temperature $T_c$ about equal to the pre-heating set point temperature $T_{ph}$. As shown, the heating power can remain constant during the pre-heating stage. However, in alternative embodiments, the heating power can increase or decrease as commanded by the controller 104 to achieve the pre-heating set point temperature $T_{ph}$.

In operation 2014, the enclosed biological substance 602 is received within the selected dry thawing chamber 200. As an example, the chamber door 302, 809, 811, 909, 911, 1204 is opened to allow placement of the enclosed biological substance 602 within the chamber frame 202, 1222, 1224. In certain embodiments, the enclosed biological substance 602 can be within the overwrap bag 120, 606, 1000, 1100 and the overwrap bag 120, 606, 1000, 1100 can be placed within the chamber frame 202, 1222, 1224.

Figure 26:
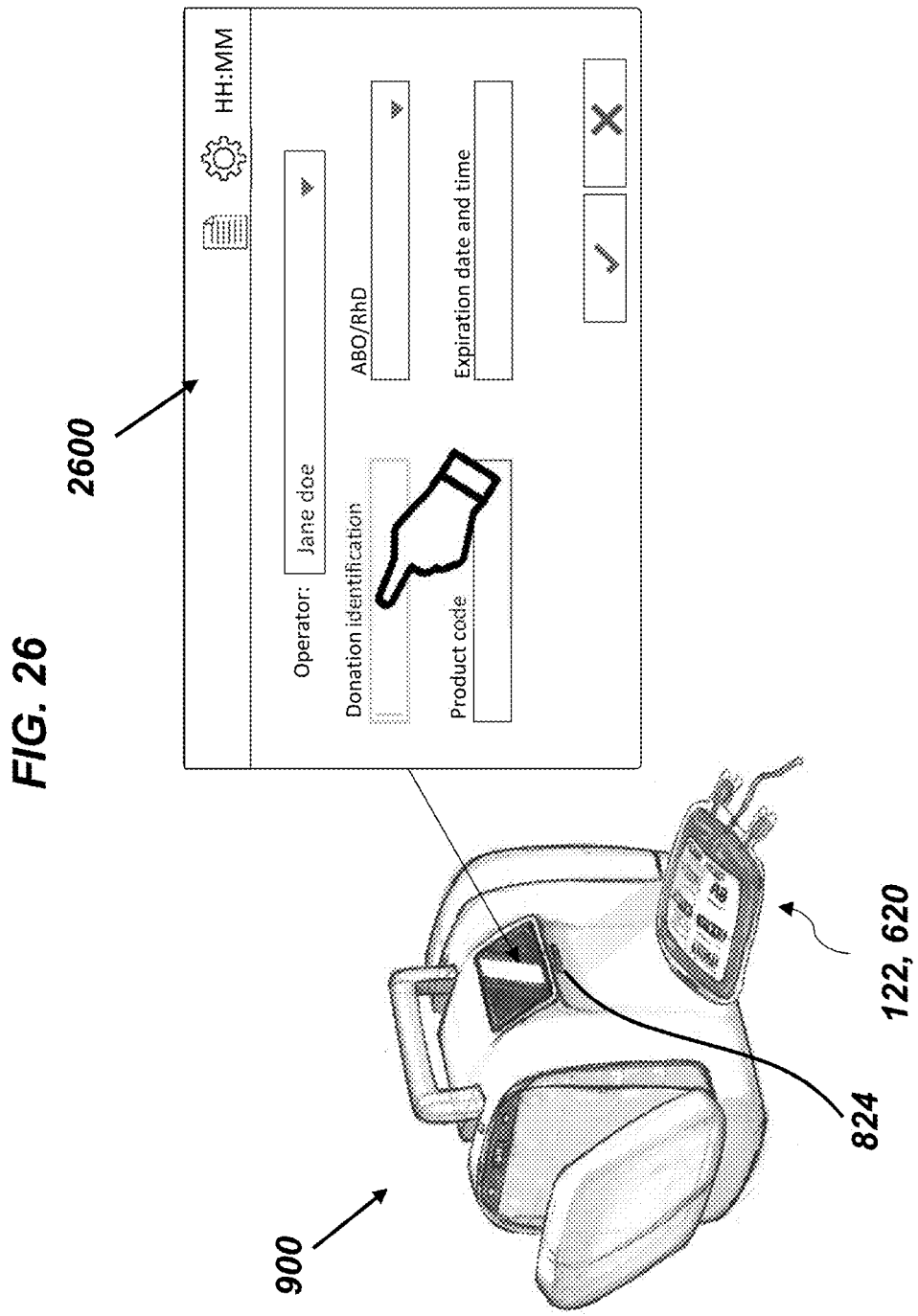
FIG. 26 is a diagram illustrating an interface for use by embodiments of the disclosed dry thawing systems to input information regarding the enclosed biological substance.

As shown in FIG. 26, the user interface 822 can be configured to display an interface 2600 configured to allow input of selected information regarding the enclosed biological substance 602. Alternatively or additionally, an operator can employ the input device 824 (e.g., a barcode reader configured to read a barcode on the enclosed biological substance 122, 602, an RFID reader configured to receive information stored by the RFID tag 1001, etc.) to automatically enter this information. Examples of information regarding the enclosed biological substance 122, 602 can include information according to the ISBT 128 standard. Examples include donation identification, product code, and classification of the enclosed biological substance 122, 602 under the ABO and/or RhD blood group system (ABO/RhD). The donation identification can be a unique identifier for the enclosed biological substance 122, 602. The product code can specify physical parameters of the enclosed biological substance 122, 602, such as volume. Further information can include an operator name and an expiration date/time.

In operation 2016, the controller 104 determines whether the chamber door 302, 809, 811, 909, 911, 1204 is closed (Door Closed?). In certain embodiments, the chamber door 302, 809, 811, 909, 911, 1204 can be in communication with a door sensor (not shown) configured to output a signal in response to opening and closing of the chamber door 302, 809, 811, 909, 911, 1204. Examples of the sensor can include mechanical sensors (e.g., buttons), electromagnetic sensors (e.g., proximity sensors), and the like. The controller 104 can be in signal communication with the door sensor. Upon receipt of an open door signal, the controller 104 can command the user interface 822 to provide an annunciation (e.g., a sound, visual cue, prompt, etc.) to remind the operator to confirm that the chamber door 302, 809, 811, 909, 911, 1204 is closed. Alternatively, the controller 104 can refrain from displaying such a prompt under circumstances where a closed door signal is received within a predetermined time after receipt of the open door signal.

An affirmative input by the operator to the annunciation and/or subsequent receipt of the closed door signal can be interpreted by the controller 104 as Door Closed=YES. A negative input or the absence of input to the annunciation can be interpreted by the controller 104 as Door Closed=NO. Once the controller 104 determines that Door Closed=YES, the method 2000 moves to operation 2020.

In operation 2020, the controller 104 receives a measurement of the weight W of the enclosed biological substance 122, 602 from the weight sensor 1279 or a memory. If the controller 104 determines W>0 is NO, the method 2000 returns to the loading operation of operation 2014. If the controller 104 determines that W>0 is YES, the method 2000 moves to operation 2102 of method 2100.

Beneficially, the sequence of operations 2014-2020 confirms that an enclosed biological substance 122, 602 is received within the chamber frame 202, 1222, 1224 and that the chamber door 302, 809, 811, 909, 911, 1204 is closed. In one aspect, if no enclosed biological substance 122, 602 is present within the chamber frame 202, there is no purpose to exiting the pre-heating stage (moving to operation 2102 of method 2100). In another aspect, if the chamber door 302, 809, 811, 909, 911, 1204 is not closed, significant heat may escape from the dry thawing system 100a, 100b, 100c, 100d, 800, 900, inhibiting the achievement of substantially uniform heating of the enclosed biological substance 122, 602 and the pre-heating set point temperature $T_{ph}$.

Figure 21:
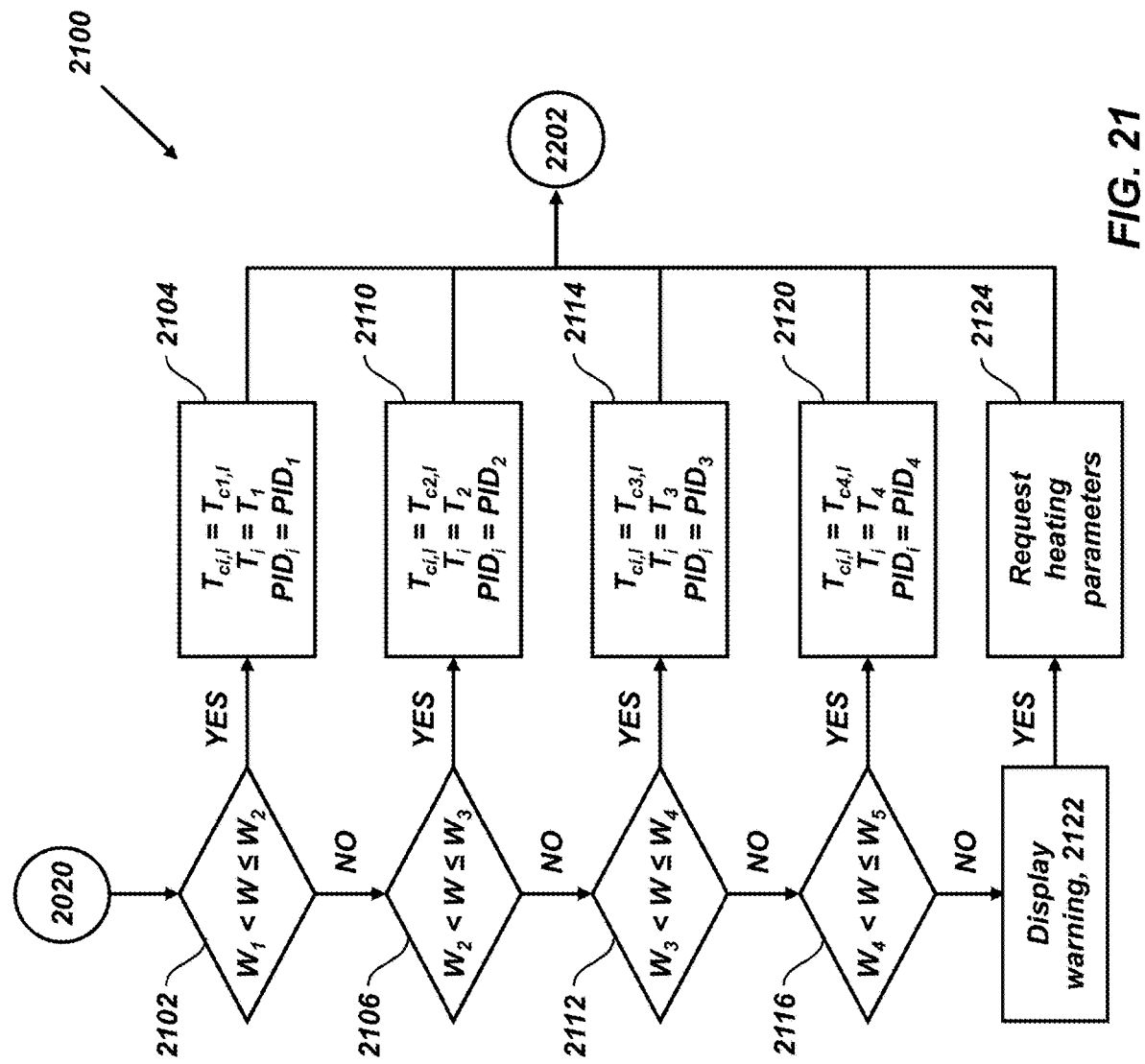
FIG. 21 is a flow diagram illustrating one exemplary embodiment of a method for determining parameters for closed-loop feedback control of heating the selected dry thawing chambers based upon a weight of the enclosed biological substance.

FIG. 21 is a flow diagram illustrating one exemplary embodiment of a method 2100, including operations 2102-2124, for determining heating parameters for the enclosed biological substance 122, 602 during the ice stage based upon measured weight. As discussed above, embodiments of the dry thawing system 100a, 100b, 100c, 100d, 800, 900 can be configured to receive enclosed biological substances 122, 602 having different volume. It can be appreciated that, if the same heating parameters are employed for significantly different volumes of the enclosed biological substance 122, 602, the amount of time required to complete the thawing process (e.g., the ice stage and the liquid stage) can vary significantly. Thus, it can be beneficial to employ different heating parameters based upon the weight of the enclosed biological substance 122, 602. Examples of the heating parameters can include a first cushion set point temperature $T_{ci,1}$ within the ice stage, PID settings within the ice stage, and a transition set point temperature $T_i$ between the ice stage and the liquid stage. In this context, the index i ranges from 1 to 4, representing four predefined weight ranges. However, alternative embodiments of the method can include greater or fewer weight ranges and the endpoints of the ranges can be varied as necessary. For example, the weights can be selected between any two desired endpoints (e.g., between about 0 g and about 500 g).

In operation 2102, the controller 104 determines if the weight W of the enclosed biological substance 122, 602 is greater than about a predetermined first weight $W_1$ and less than or equal to about a predetermined second weight $W_2$ ($W_1 < W \leq W_2$ ?). If $W_1 < W \leq W_2$ is YES, the method 2100 moves to operation 2104, where the heating parameters $T_{ci,1} = T_{c1,1}$, $T_i = T_1$, and $PID_i = PID_1$ are retrieved from memory by the controller 104. If $W_1 < W \leq W_2$ is NO, the method 2100 moves to operation 2106.

In operation 2106, the controller 104 determines if the weight W of the enclosed biological substance 122, 602 is greater than about the predetermined second weight $W_2$ and less than or equal to about a predetermined third weight $W_3$ ($W_2 < W \leq W_3$ ?). If $W_2 < W \leq W_3$ is YES, the method 2100 moves to operation 2110, where the heating parameters $T_{ci,1} = T_{c2,1}$, $T_i = T_2$, and $PID_i = PID_2$ are retrieved from memory by the controller 104. If $W_2 < W \leq W_3$ is NO, the method 2100 moves to operation 2112.

In operation 2112, the controller 104 determines if the weight W of the enclosed biological substance 122, 602 is greater than the third predetermined weight $W_3$ and less than or equal to about a predetermined fourth weight $W_4$ ($W_3 < W \leq W_4$ ?). If $W_3 < W \leq W_4$ is YES, the method 2100 moves to operation 2114, where the heating parameters $T_{ci,1} = T_{c3,1}$, $T_i = T_3$, and $PID_i = PID_3$ are retrieved from memory by the controller 104. If $W_3 < W \leq W_4$ is NO, the method 2100 moves to operation 2116.

In operation 2116, the controller 104 determines if the weight W of the enclosed biological substance 122, 602 is greater than the fourth predetermined weight $W_4$ and less than or equal to about a predetermined fifth weight $W_5$ ($W_4 < W \leq W_5$ ?). If $W_4 < W \leq W_5$ is YES, the method 2100 moves to operation 2120, where the heating parameters $T_{ci,1} = T_{c4,1}$, $T_i = T_4$, and $PID_i = PID_4$ are retrieved from memory by the controller 104. If $W_4 < W \leq W_5$ is NO, the method 2100 moves to operation 2122.

In operation 2122, the user interface 822 displays a warning. Display of the warning in operation 2122 can reflect an enclosed biological substance 122, 602 having a weight that does not fall within the ranges outlined above. Following display of the warning in operation 2122, the method 2100 can move to operation 2124, where the user interface 822 displays the measured weight W of the enclosed biological substance 122, 602 and requests operator input of the parameters $T_{ci,1}$, $T_i$, and $PID_i$.

Exemplary embodiments of weight ranges are outlined in Table 1.

TABLE 1

| Weight ranges | |
|---|---|
| Index, i | Weight range |
| 1 | 100 g < W ≤ 200 g |
| 2 | 200 g < W ≤ 300 g |
| 3 | 300 g < W ≤ 400 g |
| 4 | 400 g < W ≤ 500 g |

Figure 22:
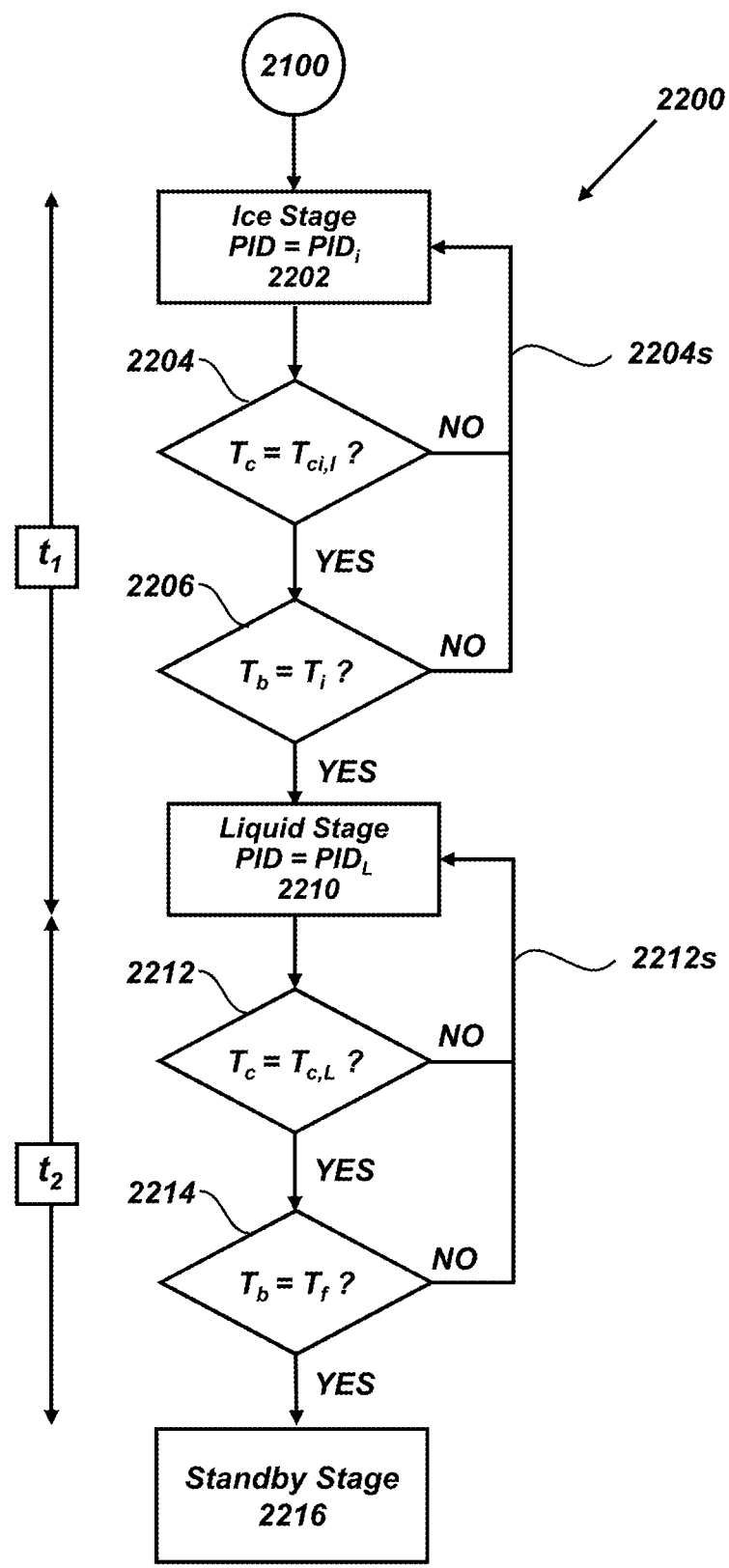
FIG. 22 is a flow diagram illustrating one exemplary embodiment of a method for thawing the enclosed biological substance.

FIG. 22 is a flow diagram illustrating one exemplary embodiment of a method 2200, including operations 2202-2216 for heating the enclosed biological substance 122, 602 during the ice stage and liquid stage. The ice stage commences in operation 2202 and ends after completion of operation 2210, while the liquid stage commences in operation 2212 and ends after completion of operation 2214. In general, the ice stage represents a condition of the enclosed biological substance 122, 602 in which a predetermined fraction of the enclosed biological substance 122, 602 is solid (e.g., frozen). The liquid stage represents a condition of the enclosed biological substance 122, 602 in which a predetermined fraction of the enclosed biological substance 122, 602 is liquid (e.g., thawed).

In operation 2202, the controller 104 obtains the ice stage parameters $T_{ci,1}$, $T_i$, and $PID_i$. As an example, Table 1 can be a lookup table stored in memory and the ice stage parameters can be determined by the controller 104 from this lookup table based upon the weight of the enclosed biological substance 122, 602.

In operation 2204, the controller 104 generates one or more command signals 2204s operative to control power delivered to the one or more heating assemblies 108, 110, 400, 500, 1208, 1242, 1732 to effect the temperature of respective heating cushions 116, 118, 1250, 1650, 1750. As discussed above, the controller 104 is configured to perform closed-loop control of the heating cushion temperature.

In order to generate the command signals 2204s, the controller 104 determines if there is a difference between each measured cushion temperature $T_c$ and the first cushion set point temperature $T_{ci,1}$ ($T_c = T_{ci,1}$?). As illustrated in Table 1, the first cushion set point temperature $T_{ci,1}$ can range from about 37° C. to about 42° C., based upon the weight W of the enclosed biological substance 122, 602. If the controller 104 determines that there is a difference between the measured cushion temperature $T_c$ and the first cushion set point temperature $T_{ci,1}$ ($T_c = T_{ci,1}$ is NO), a correction is calculated based upon this difference and $PID_i$. The correction is transmitted from the controller 104 to respective ones of the heating assemblies 108, 110, 400, 500, 1208, 1242, 1732 as the command signals 2204s and the method 2200 returns to operation 2202. In operation 2202, the one or more heating assemblies 108, 110, 400, 500, 1208, 1242, 1732 generate heat in response to receipt of the command signal(s) 2204s. Subsequently, the method 2200 moves to operation 2204 to again determine if there is a difference between each measured cushion temperature $T_c$ and the first cushion set point temperature $T_{ci,1}$. The operations 2202 and 2204 are repeated in sequence until the measured cushion temperature $T_c$ is about equal to the first cushion set point temperature $T_{ci,1}$ ($T_c=T_{ci,1}$ is YES). Subsequently, the method 2200 can move to operation 2206.

In operation 2206, the controller 104 determines whether the measured temperature $T_b$ of the enclosed biological substance 122, 602 is equal to the transition set point temperature $T_i$ ($T_b=T_i$ ?). In an embodiment, the transition set point temperature $T_i$ can be a temperature above 0° C. at which most or all of the enclosed biological substance 122, 602 is melted into liquid. As illustrated in Table 1, the transition set point temperature $T_i$ can range from about 5° C. to about 8° C. If $T_b=T_i$ is NO in operation 2206, the method 2200 returns to operation 2202. Alternatively, when $T_b=T_i$ is YES in operation 2206, the method 2200 moves to operation 2210, which ends the ice stage and begins the liquid stage.

FIG. 30 illustrates one exemplary embodiment of the measured cushion temperature $T_c$ (dot-dash-dot line), the measured temperature $T_b$, of the enclosed biological substance 122, 602 and power P delivered to the one or more heating cushions 116, 118, 1250, 1650, 1750 (dot-dot-dash line) as a function of time during the ice stage. Assuming that the ice stage follows the pre-heating stage, at thawing time t=0, the measured cushion temperature $T_c$ is about the pre-heating set point temperature $T_{ph}$ and the measured temperature $T_b$ of the enclosed biological substance 122, 602 is at an initial temperature $T_o$. The initial temperature $T_o$ can be a temperature at which the enclosed biological substance 122, 602 is stored in its frozen state.

When transitioning from the pre-heating stage to the ice stage, the set point temperature for the heating cushion changes from the pre-heating set point temperature $T_{ph}$ to the first cushion set point temperature $T_{ci,1}$. As shown in FIG. 30, the first cushion set point temperature $T_{ci,1}$ is greater than the pre-heating set point temperature $T_{ph}$. Thus, $T_c=T_{ci,1}$ is NO in operation 2204 and the controller 104 transmits command signal(s) 2204s operative to cause the heating power P to increase and the one or more heating assemblies 108, 110, 400, 500, 1208, 1242, 1732 generate more heat. As shown, the heating power P can rise from the pre-heating stage power $P_{ph}$ at thawing time t=0 to an ice stage power level $P_1$.

In response to the increased heat generation during the ice stage, the measured cushion temperature $T_c$ rises. Once the measured cushion temperature $T_c$ reaches the first cushion set point temperature $T_{ci,1}$ ($T_c=T_{ci,1}$ is YES in operation 2204), the controller 104 further generates command signal(s) operative to maintain the cushion temperature $T_c$ about equal to the first cushion set point temperature $T_{ci,1}$. As shown, the heating power can remain about constant during the ice stage. However, in alternative embodiments, the heating power P can increase or decrease as commanded by the controller to achieve the first cushion set point temperature $T_{ci,1}$.

Concurrently, the measured temperature $T_b$ of the enclosed biological substance 122, 602 initially rises from $T_o$ at thawing time t=0. With increasing time, the measured temperature $T_b$ of the enclosed biological substance 122, 602 increases until it reaches its melting point. Subsequently, the heat generated by the one or more heating assemblies 108, 110, 400, 500, 1208, 1242, 1732 is employed for melting, that is, a solid to liquid phase transition. While this phase transition occurs, the measured temperature $T_b$ of the enclosed biological substance 122, 602 remains approximately constant. Once at least a portion of the enclosed biological substance 122, 602 becomes liquid, the measured temperature $T_b$ of the enclosed biological substance 122, 602 begins to increase again. The ice stage continues until the measured temperature $T_b$ of the enclosed biological substance 122, 602 is about equal to the transition set point temperature $T_i$ ($T_b=T_i$ is YES in operation 2206).

The liquid stage begins in operation 2210 of method 2200. In operation 2210, the controller 104 obtains the following liquid stage parameters: a second cushion set point temperature $T_{c,L}$, a final set point temperature $T_f$, and liquid stage PID settings $PID_L$. The liquid stage parameters $T_{c,L}$, $T_f$ and $PID_L$ can be independently received by the controller 104 in a variety of ways. In one aspect, these parameters can be input by the operator via the user interface 822. In another aspect, these liquid stage parameters can be retrieved from a memory. In a further aspect, these liquid stage parameters can be hard-coded. In certain embodiments, $T_{c,L}$ can be selected from about 35° C. to about 36° C. (e.g., about 36° C.).

In operation 2212, the controller 104 generates one or more command signals 2212s operative to control power delivered to the one or more heating assemblies 108, 110, 400, 500, 1208, 1242, 1732 to effect the temperature of respective heating cushions 116, 118, 1250, 1650, 1750. As discussed above, the controller 104 is configured to perform closed-loop control of the heating cushion temperature.

In order to generate the command signals 2212s, the controller 104 determines if there is a difference between each measured cushion temperature $T_c$ and the second cushion set point temperature $T_{c,L}$ ($T_c=T_{c,L}$?). If the controller 104 determines that there is a difference between the measured cushion temperature $T_c$ and the second cushion set point temperature $T_{c,L}$ ($T_c=T_{c,L}$ is NO), a correction is calculated based upon this difference and $PID_L$. The correction is transmitted from the controller 104 to respective ones of the heating assemblies 108, 110, 400, 500, 1208, 1242, 1732 as the command signals 2212s and the method 2200 returns to operation 2202. In operation 2210, the one or more heating assemblies 108, 110, 400, 500, 1208, 1242, 1732 generate heat in response to receipt of the command signal(s) 2212s. Subsequently, the method 2200 moves to operation 2012 to again determine if there is a difference between each measured cushion temperature $T_c$ and the first cushion set point temperature $T_{c,L}$. The operations 2210 and 2212 are repeated in sequence until the measured cushion temperature $T_c$ is about equal to the second cushion set point temperature $T_{c,L}$ ($T_c=T_{c,L}$ is YES). Subsequently, the method 2200 can move to operation 2214.

In operation 2214, the controller 104 determines whether the measured temperature $T_b$ of the enclosed biological substance 122, 602 is equal to the predetermined final set point temperature $T_f$ ($T_b=T_f$ ?). The final set point temperature $T_f$ can represent a target temperature for the liquid stage. That is, a temperature sufficiently high to ensure that all of the enclosed biological substance 122, 602 is thawed (e.g., in the liquid phase) but not so high that the enclosed biological substance 122, 602 is thermally damaged. If $T_b=T_f$ is NO in operation 2214, the method 2200 returns to operation 2210, where the controller 104 continues to command the one or more heating assemblies 108, 110, 400, 500,

1208, 1242, 1732 to generate heat. If $T_b=T_f$ is YES in operation 2214, the method 2200 moves to operation 2216, which ends the liquid stage and begins the standby stage.

In general, the final set point temperature $T_f$ can range from about 0° C. to about 37° C. the exact value of the final set point temperature $T_f$ can be dependent upon the type of enclosed biological substance and/or the weight of the enclosed biological substance. In an embodiment where the enclosed biological substance is a blood plasma, the final set point temperature $T_f$ can range from about 30° C. to about 37° C. (e.g., about 33.5° C.). In an embodiment, the enclosed biological substance 122, 602 can be a blood component and the value of the final set point temperature $T_f$ can be based upon the blood component according to standards set by regional, national, and/or international standard bodies. In one embodiment, $T_f$ can be determined pursuant to the "Circular of Information for the Use of Human Blood and Blood Components," published by AABB, November 2017.

Referring again to FIG. 30, the measured temperature of the heating cushion $T_c$, the measured temperature $T_b$ of the enclosed biological substance 122, 602, and power P delivered to the one or more heating cushions 116, 118, 1250, 1650, 1750 (dot-dot-dash line) as a function of time are also illustrated in the liquid stage. As shown, the liquid stage follows the ice stage. At thawing time $t=t_1$, the measured cushion temperature $T_c$ is about equal to the first cushion set point temperature $T_{ci,1}$ and the measured temperature $T_b$ of the enclosed biological substance 122, 602 is about equal to the transition set point temperature $T_i$.

When transitioning from the ice stage to the liquid stage, the set point temperature for the heating cushion changes from the first set point temperature $T_{ci,1}$ to the second cushion set point temperature $T_{c,L}$. As shown in FIG. 30, the second cushion set point temperature $T_{c,L}$ is less than the first cushion set point temperature $T_{ci,1}$. Thus, $T_c=T_{c,L}$ is NO in operation 2212 and the controller 104 transmits command signal(s) 2204s operative to cause the heating power P to decrease. That is, the one or more heating assemblies 108, 110, 400, 500, 1208, 1242, 1732 generate less heat at the start of the liquid stage, as compared to the end of the ice stage, in order to decrease the measured heating cushion temperature $T_c$. As shown, the heating power P can decrease from the ice stage power $P_1$ at thawing time $t=t_1$.

In response to the reduction in heat generated by the heating assemblies 108, 110, 400, 500, 1208, 1242, 1732, the measured cushion temperature $T_c$ decreases. Once the measured cushion temperature $T_c$ reaches the second cushion set point temperature $T_{c,L}$ ($T_c=T_{c,L}$ is YES in operation 2212), the controller 104 further generates command signal(s) operative to maintain the cushion temperature $T_c$ about equal to the second cushion set point temperature $T_{c,L}$. As shown, the heating power P can decrease throughout the duration of the liquid stage. However, in alternative embodiments, the heating power P can increase or decrease as commanded by the controller 104 to achieve the second cushion set point temperature $T_{c,L}$.

Concurrently, the measured temperature $T_b$ of the enclosed biological substance 122, 602 rises relatively rapidly from $T_i$ at thawing time $t=t_1$. However, with increasing time, the slope of the temperature-time response the measured temperature $T_b$ of the enclosed biological substance 122, 602 decreases. The liquid stage continues until the measured temperature $T_b$ of the enclosed biological substance 122, 602 is about equal to the final set point temperature $T_f$ ($T_b=T_f$ is YES in operation 2214).

With the conclusion of the liquid stage in operation 2214, the method 2200 enters the standby stage when moving to operation 2216. In operation 2216, the controller 104 obtains the following standby stage parameters: a third cushion set point temperature $T_{c,SB}$ and standby stage PID settings $PID_{SB}$. The standby stage parameters $T_{c,SB}$ and $PID_{SB}$ can be independently received by the controller 104 in a variety of ways. In one aspect, the standby stage parameters can be input by the operator via the user interface 822. In another aspect, the standby stage parameters can be retrieved from a memory. In a further aspect, the standby stage parameters can be hard-coded. In certain embodiments, the third cushion set point temperature $T_{c,SB}$ can be selected from about 35° C. to about 37° C. (e.g., about 35° C.)

During the standby stage of operation 2216, the controller 104 is further configured to maintain the temperature of the one or more heating cushions 116, 118, 1250, 1650, 1750 to be about equal to the third cushion set point temperature $T_{c,SB}$. Similar to the discussion above, in operation 2216, the controller 104 can generate standby command signals operative to control power delivered to the one or more heating assemblies 108, 110, 400, 500, 1208, 1242, 1732 in order to maintain the cushion temperature about equal to the standby set point temperature $T_{c,SB}$. The standby command signals can be based upon the $PID_{SB}$ and the difference between the measured cushion temperature $T_c$ and the fourth cushion set point temperature $T_{c,SB}$.

When transitioning from the liquid stage, the set point temperature for the heating cushion changes from the second set point temperature $T_{c,L}$ to the third cushion set point temperature $T_{c,SB}$. However, as shown in FIG. 30, the third cushion set point temperature $T_{c,SB}$ can be about equal to the second cushion set point temperature $T_{c,L}$. Furthermore, the heating power P can continue to decrease during the standby stage. Concurrently, the measured temperature of the enclosed biological substance 122, 602 can be about constant during the standby stage.

Embodiments of the controller 104 can also be configured to record the elapsed time of the ice stage, the liquid stage, and the standby stage. As discussed below, in certain embodiments, the controller 104 can also be configured to halt the thawing process during the method 2200 based upon measurements of elapsed time.

Figure 23:
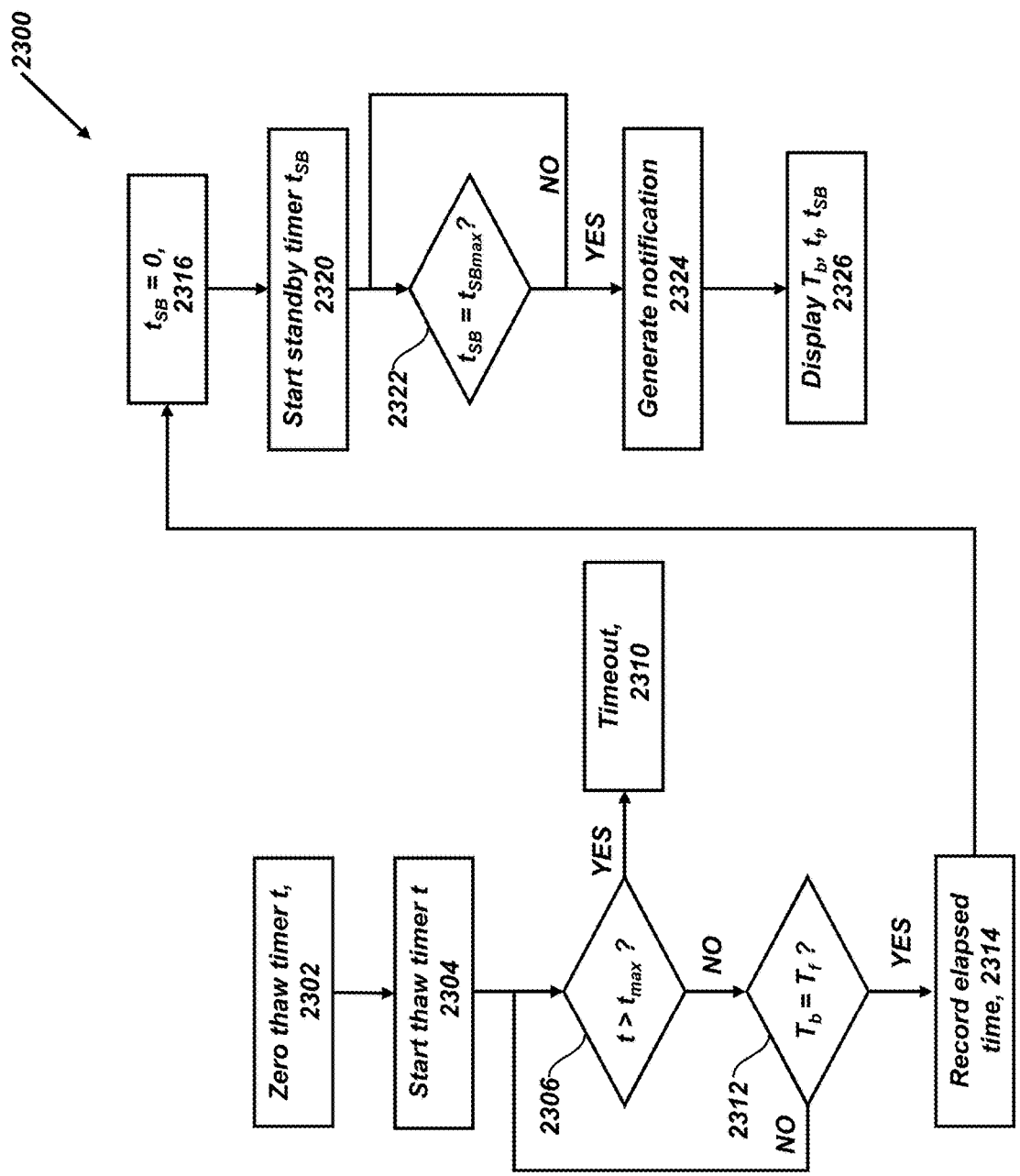
FIG. 23 is a flow diagram illustrating one exemplary embodiment of a method for monitoring a thawing time and a standby time.

As illustrated in FIG. 23, in operation 2302, the controller 104 zeros a thawing time t maintained by a thawing timer after the pre-heating is completed and prior to the ice stage. In operation 2304, when the ice stage commences at operation 2202, the thawing timer is started.

In operation 2306, while the thawing timer is running, the controller 104 determines if the thawing time t exceeds a maximum thawing time $t_{max}$ ($t>t_{max}$ ?). In general, the maximum thawing time $t_{max}$ represents a predetermined safe time duration for thawing of the enclosed biological substance 122, 602. Therefore, if $t>t_{max}$ is YES, the method 2300 moves to operation 2310, entering a timeout condition. In the timeout condition, the controller 104 commands the one or more heating assemblies 108, 110, 400, 500, 1208, 1242, 1732 to stop generating heat and generates a message for display by the user interface 822 indicating the timeout condition and prompting the operator to remove the enclosed biological substance 122, 602 from the dry thawing 100a, 100b, 100c, 100d, 800, 900 for disposal. Alternatively, if $t>t_{max}$ is NO, the method 2300 moves to operation 2312.

In operation 2312, the controller 104 determines when the liquid stage has ended. Similar to operation 2214, the controller 104 determines the end of the liquid stage when the measured temperature $T_b$ of the enclosed biological substance 122, 602 is equal to a the final set point temperature $T_f$ ($T_b=T_f$?). If $T_b=T_f$ is NO, the method 2300 returns to operation 2306. If $T_b=T_f$ is YES, the method 2300 moves to operation 2214.

In operation 2314, the controller 104 records a first thawing time $t_1$ elapsed for the ice stage, a second thawing time $t_2$ elapsed for the liquid stage, and a total thawing time $t_t$ given by the sum of the first and second thawing times $t_1$, $t_2$. The thawing time $t_1$ is determined from the start of operation 2202 to when $T_b=T_i$ is YES in operation 2206. The thawing time $t_2$ is determined from the ice stage time $t_1$ to when $T_b=T_f$ is YES in operation 2214. Subsequently, the method 2300 moves to operation 2316.

In operations 2316-2324, the controller 104 monitors an amount of standby time $t_{sb}$ elapsed during the standby stage. In general, it can be desirable for the enclosed biological substance 122, 602 to be removed from the dry thawing 100a, 100b, 100c, 100d, 800, 900 shortly after the liquid stage is complete. Accordingly, the controller 104 can alert the operator when the standby time $t_{sb}$ exceeds a predetermined maximum standby time $t_{sb, max}$. In operation 2316, the controller 104 zeros the standby timer $t_{sb}$. In operation 2320, the controller 104 starts a standby timer to record the standby time $t_{sb}$.

In operation 2322, the controller 104 determines whether the standby time $t_{sb}$ equals the maximum standby time $t_{sb, max}$ ($t_{sb}=t_{sb, max}$?). If $t_{sb}=t_{sb, max}$ is NO, the method 2300 returns to 2322 and the standby timer $t_{sb}$ continues running. If $t_{sb}=t_{sb, max}$ is YES, the method 2300 moves to operation 2324.

In operation 2324, the controller 104 generates a notification to alert the operator that the maximum standby time $t_{sb, max}$ has been reached. The notification can include any audio and/or visual signal. Examples can include audible alarms, lights, and messages displayed by the user interface 822.

Subsequently, in operation 2326, the user interface 822 can display the current temperature $T_b$ of the enclosed biological substance 122, 602, the total thawing time $t_t$ ($t_1+t_2$), and the standby time $t_{sb}$. The controller 104 can further return to the operation 2010 of method 2100 to prepare the selected dry thawing chamber 200, 804, 800, 904, 906 for receipt of another enclosed biological substance 122, 602.

Figure 27:
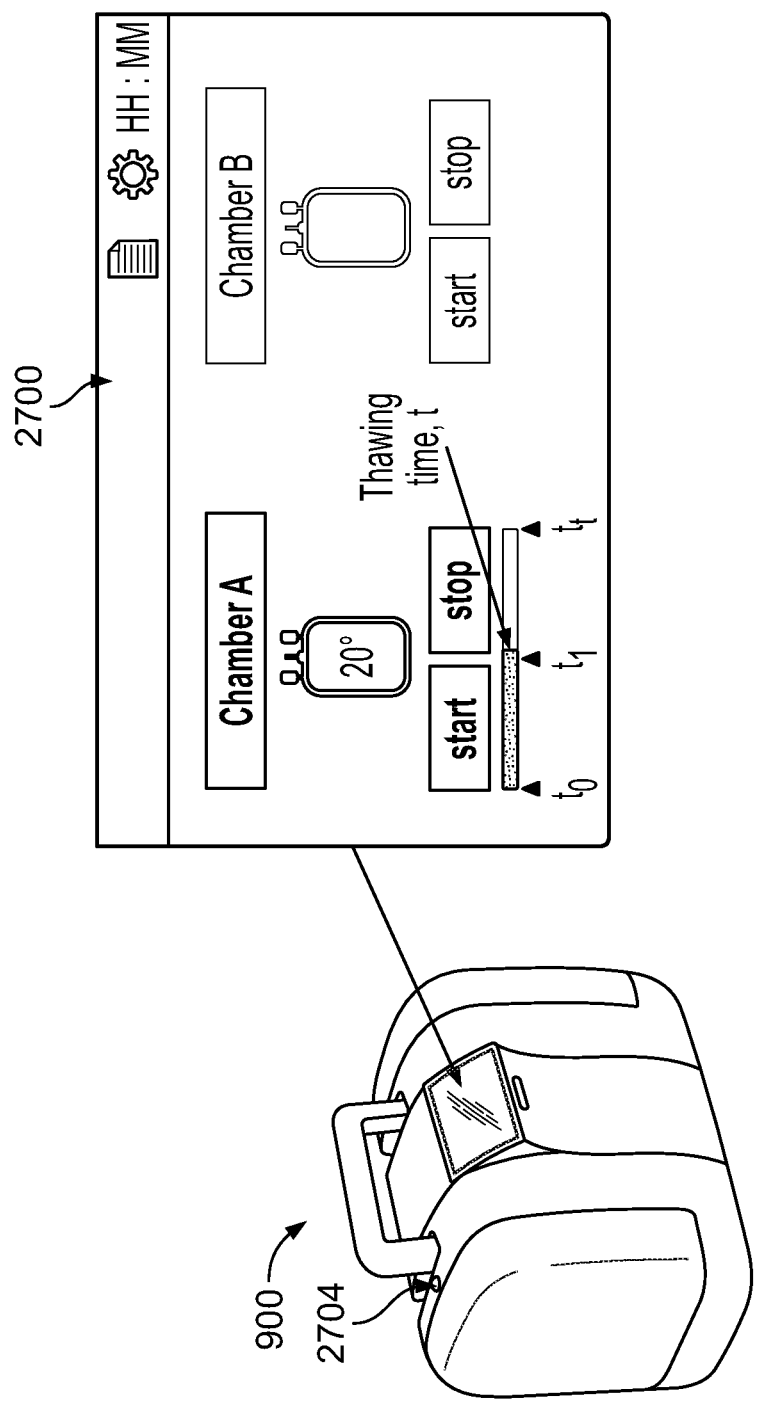
FIG. 27 is a diagram illustrating an interface for use by embodiments of the disclosed dry thawing systems for monitoring a dry thawing operation.

FIG. 27 illustrates an embodiment of an interface 2700 displayed by the user interface 822 during the ice stage and the liquid stage. As shown, the measured temperature $t_b$ of the enclosed biological substance 122, 602 (e.g., 20° C.) is displayed, as well as thawing time t elapsed from commencement of the ice stage at thawing time t=0. In certain embodiments, the first thawing time $t_1$ at which the transition between the ice stage and the liquid stage occurs. An indicator light 2704 of the selected dry thawing chamber 200, 804, 800, 904, 906 (e.g., Chamber A) can also display a first color representing the status of the selected dry thawing chamber 200, 804, 800, 904, 906 as in use (e.g., an orange color). Alternatively or additionally, in further embodiments, the first color can be displayed by the user interface 822.

Figure 28:
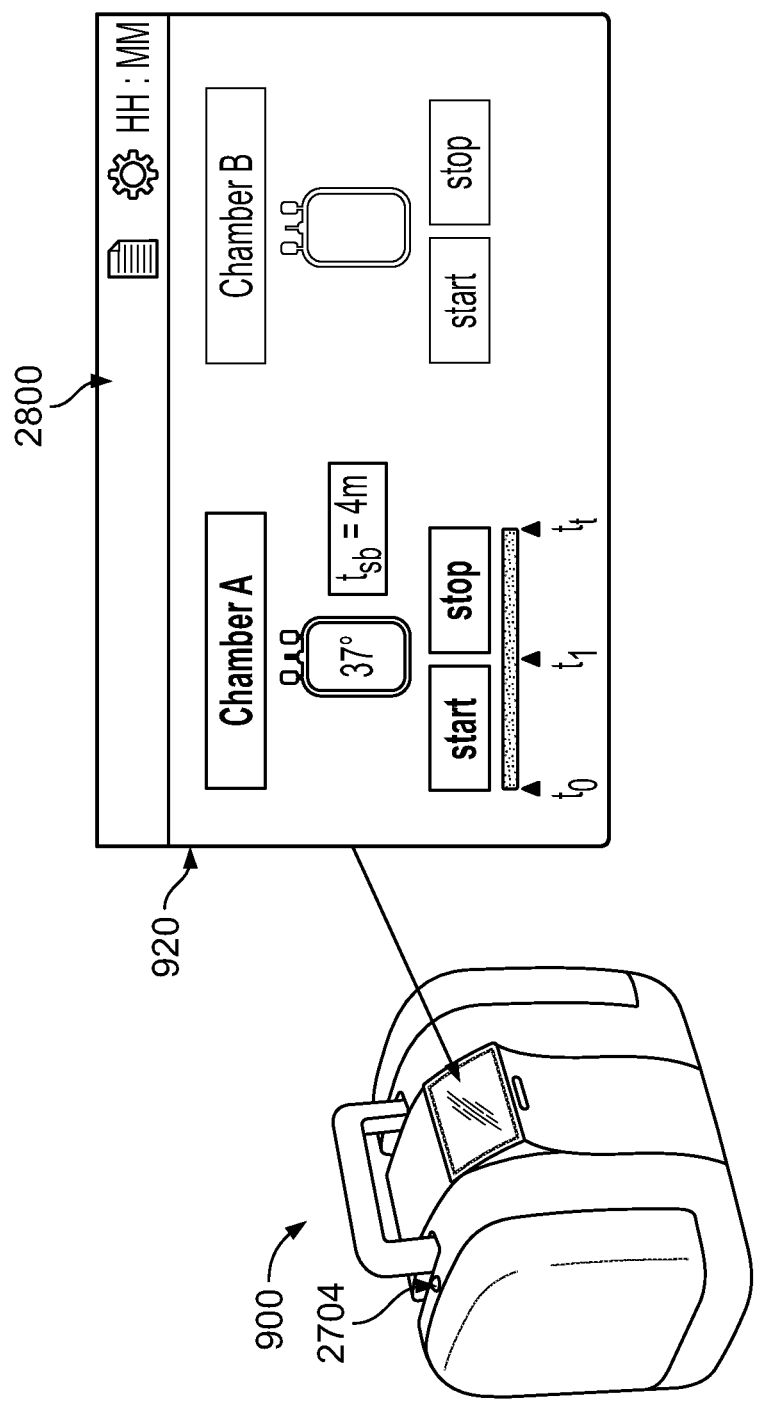
FIG. 28 is a diagram illustrating an interface for use by embodiments of the disclosed dry thawing systems to display information regarding a completed dry thawing operation.

FIG. 28 illustrates an interface 2800 displayed by the user interface 822 upon completion of the dry thawing process (e.g., operation 2326 of method 2300). As shown, the measured temperature $t_b$ of the enclosed biological substance 122, 602 is displayed (e.g., 37° C.), as well as the total time $t_t$ elapsed in the dry thawing process and the standby time $t_{sb}$. The indicator light 2704 of the selected dry thawing chamber 200, 804, 800, 904, 906 can also display a second color representing the status of the selected dry thawing chamber 200, 804, 800, 904, 906 as complete (e.g., a green color). Alternatively or additionally, in further embodiments, the second color can be displayed by the user interface 822.

Figure 29:
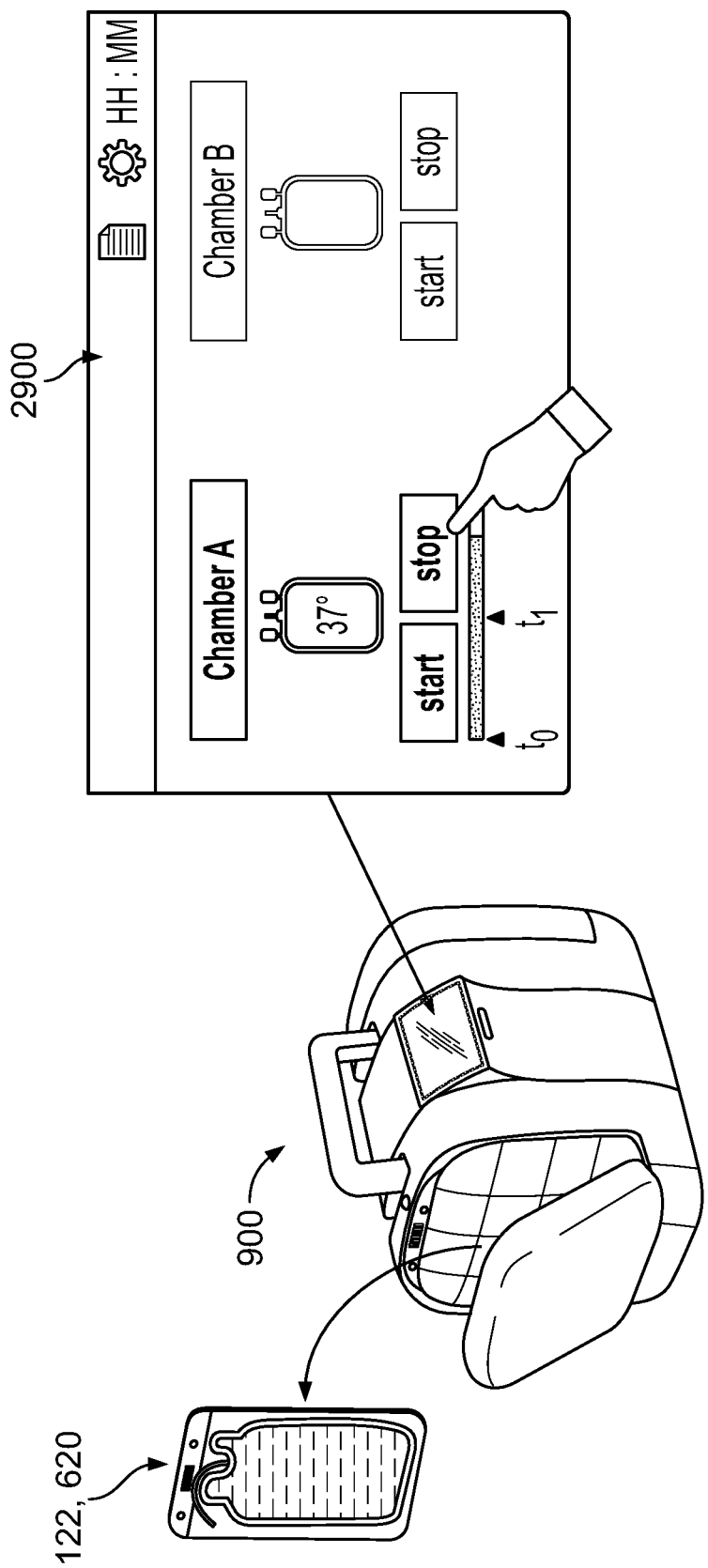
FIG. 29 is a diagram illustrating an interface for use by embodiments of the disclosed dry thawing systems to stop a dry thawing operation for removal of an enclosed biological substance.

As illustrated in FIG. 29 the operator can select a "stop" option from an interface 2900 displayed by the user interface 822. The "stop" option can be selected at any time during the pre-heating stage, the ice stage, the liquid stage, or the standby stage. Selection of the "stop" option during any of the pre-heating stage, the ice stage, the liquid stage, and the standby stage aborts the thawing and/or heating process and causes the controller 104 to cut power to the one or more heating assemblies 108, 110, 400, 500, 1208, 1242, 1732. Selection of the "stop" option during the standby stage indicates that the dry thawing process has been completed and the selected dry thawing chamber 200, 804, 800, 904, 906 is available to receive another frozen biological substance. Following selection of the "stop" option during the standby stage, the controller 104 can return to the operation 2010 of method 2100 to prepare the selected dry thawing chamber 200, 804, 800, 904, 906 for receipt of another enclosed biological substance 122, 602.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A dry thawing device, comprising:
a chamber frame configured to receive an enclosed biological substance;
a first heating assembly coupled to the chamber frame, the first heating assembly comprising a heater configured to be in thermal communication with an enclosed biological substance that is received within the chamber frame; and
an agitator mounted within the chamber frame and configured to cause the first heating assembly to pivot about a pivot axis relative to the chamber frame to agitate an enclosed biological substance received within the chamber frame, wherein the agitator comprises a cam, and wherein the cam is in contact with the first heating assembly.

2. The dry thawing device of claim 1, wherein the first heating assembly is linearly slidably movable relative to the chamber frame via a track.

3. The dry thawing device of claim 2, further comprising at least one biasing element that biases the first heating assembly into contact with an enclosed biological substance that is received within the chamber frame.

4. The dry thawing device of claim 1, wherein the first heating assembly is configured to be positioned adjacent to a first side of an enclosed biological substance that is received within the chamber frame and the second heating assembly is configured to be positioned adjacent to a second side of the enclosed biological substance that is opposite the first side.

5. The dry thawing device of claim 1, further comprising at least one temperature sensor configured to measure a temperature of at least one of the first heating assembly and an enclosed biological substance received within the chamber frame.

6. The dry thawing device of claim 1, further comprising a weight sensor configured to measure a weight of an enclosed biological substance that is received within the chamber frame.

7. The dry thawing device of claim 1, further comprising an overwrap bag disposed within the chamber frame, wherein the overwrap bag contains an enclosed biological substance.

8. The dry thawing device of claim 1, wherein the chamber frame comprises a top portion, a bottom portion, and a first end and a second end opposed to the first end, wherein each of the first end and second end is coupled to the top and bottom portions, and wherein the chamber door is mounted to the first end of the chamber frame.

9. The dry thawing device of claim 1, further comprising a second heating assembly mounted on a chamber door pivotally coupled to the chamber frame and moveable between an open position and a closed position, wherein the second heating assembly comprises a second heater configured to be in thermal communication with an enclosed biological substance that is received within the chamber frame when the chamber door is in a closed position.

10. A dry thawing device, comprising:
a chamber frame having a top portion, a bottom portion, and first and second opposed ends coupled to the top and bottom portions;
a support frame mounted to the bottom portion of the chamber frame and extending between the top and bottom portions of the chamber frame;
an agitator plate pivotally coupled to the support frame, the agitator plate configured to contact an enclosed biological substance disposed within the chamber frame; and
an agitator mounted to the support frame and configured to cause pivotal motion of the agitator plate to thereby agitate an enclosed biological substance disposed within the chamber frame.

11. The dry thawing device of claim 10, wherein the agitator includes a cam mechanism configured to cam the agitator plate to cause pivotal motion of the agitator plate.

12. The dry thawing device of claim 10, wherein the agitator plate extends between the top and bottom portions of the chamber frame and is pivotally mounted at a midportion thereof to the support frame.

13. The dry thawing device of claim 10, wherein the agitator plate comprises a plate and a first heating assembly mounted on the plate, and wherein the first heating assembly is configured to contact the enclosed biological substance and to selectively generate thermal energy to heat the enclosed biological substance.

14. The dry thawing device of claim 10, wherein the agitator plate includes a top end and a bottom end, and wherein pivotal motion of the agitator plate causes the top and bottom ends to move in opposite directions.

15. The dry thawing device of claim 10, further comprising a chamber door mounted to the first end of the chamber frame, the chamber door being moveable between open and closed positions, wherein, when the chamber door is in the closed position, the chamber door and the agitator plate define a cavity there between that is configured to receive an enclosed biological substance.

16. The dry thawing device of claim 13, further comprising:
a chamber door mounted to the first end of the chamber frame, the chamber door being moveable between open and closed positions, wherein, when the chamber door is in the closed position, the chamber door and the agitator plate define a cavity there between that is configured to receive an enclosed biological substance; and a second heating assembly mounted on the chamber door, wherein the second heating assembly comprises a heater that is configured to selectively generate heat to thaw an enclosed biological substance disposed within the cavity.

17. The dry thawing device of claim 13, wherein the first heating assembly comprises a heater and a cushion, wherein the cushion is configured to contact the enclosed biological substance.

18. The dry thawing device of claim 10, wherein the agitator comprises a cam, and wherein the cam is in contact with the agitator plate.

19. A dry thawing device, comprising:
   a chamber frame having a top portion, a bottom portion, and first and second opposed sidewalls coupled to the top and bottom portions;
   a support frame mounted to the bottom portion of the chamber frame and extending between the top and bottom portions of the chamber frame, wherein the support frame is slidably mounted to the bottom portion of the chamber frame;
   an agitator plate pivotally coupled to the support frame, the agitator plate configured to contact an enclosed biological substance disposed within the chamber frame; and
   an agitator mounted to the support frame and configured to cause pivotal motion of the agitator plate to thereby agitate an enclosed biological substance disposed within the chamber frame.

20. The dry thawing device of claim 19, wherein the support frame is biased toward an enclosed biological substance disposed within the chamber frame to thereby bias the agitator plate toward an enclosed biological substance disposed within the chamber frame.

21. The dry thawing device of claim 19, wherein the agitator plate comprises a plate and a heating assembly, wherein the heating assembly is configured to contact the enclosed biological substance disposed within the chamber frame.

22. A dry thawing device, comprising:
   a chamber frame having a top portion, a bottom portion, and first and second opposed ends coupled to the top and bottom portions;
   a support frame mounted to the bottom portion of the chamber frame and extending between the top and bottom portions of the chamber frame;
   a chamber door mounted to the first end of the chamber frame, the chamber door being moveable between open and closed positions, wherein, when the chamber door is in the closed position, the chamber door and the agitator plate define a cavity there between that is configured to receive an enclosed biological substance;
   an agitator plate pivotally coupled to the support frame, the agitator plate configured to contact an enclosed biological substance disposed within the chamber frame;
   an agitator mounted to the support frame and configured to cause pivotal motion of the agitator plate to thereby agitate an enclosed biological substance disposed within the chamber frame; and
   a heating assembly mounted on the chamber door, wherein the heating assembly comprises a heater that is configured to selectively generate heat to thaw an enclosed biological substance disposed within the cavity.

23. The dry thawing device of claim 22, wherein the heating assembly is a first heating assembly and the agitator plate comprises a plate and a second heating assembly, wherein the second heating assembly is configured to contact the enclosed biological substance disposed within the chamber frame.

24. The dry thawing device of claim 22, wherein the agitator comprises a cam, and wherein the cam is in contact with the agitator plate.

* * * * *